US008298531B2

(12) United States Patent
Mottl

(10) Patent No.: US 8,298,531 B2
(45) Date of Patent: Oct. 30, 2012

(54) TREATMENT WITH ANTI-ALPHA2 INTEGRIN ANTIBODIES

(75) Inventor: Harald Mottl, La Chaux-de-Fonds (CH)

(73) Assignee: Glenmark Pharmaceuticals, S.A., La Chaux-de-Fonds (CH)

( * ) Notice: Subject to any disclaimer, the term of this patent is extended or adjusted under 35 U.S.C. 154(b) by 269 days.

(21) Appl. No.: 12/614,178

(22) Filed: Nov. 6, 2009

(65) Prior Publication Data

US 2010/0158904 A1    Jun. 24, 2010

Related U.S. Application Data

(60) Provisional application No. 61/111,932, filed on Nov. 6, 2008.

(51) Int. Cl.
*A61K 39/00* (2006.01)
*A61K 39/395* (2006.01)

(52) U.S. Cl. ............... 424/133.1; 424/130.1; 424/141.1; 424/145.1

(58) Field of Classification Search ........................ None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,275,149 A | 6/1981 | Litman et al. |
| 4,301,144 A | 11/1981 | Iwashita et al. |
| RE30,985 E | 6/1982 | Cartaya |
| 4,419,446 A | 12/1983 | Howley et al. |
| 4,485,045 A | 11/1984 | Regen |
| 4,496,689 A | 1/1985 | Mitra |
| 4,544,545 A | 10/1985 | Ryan et al. |
| 4,560,655 A | 12/1985 | Baker |
| 4,601,978 A | 7/1986 | Karin |
| 4,640,835 A | 2/1987 | Shimizu et al. |
| 4,657,866 A | 4/1987 | Kumar |
| 4,670,417 A | 6/1987 | Iwasaki et al. |
| 4,675,187 A | 6/1987 | Konishi et al. |
| 4,676,980 A | 6/1987 | Segal et al. |
| 4,767,704 A | 8/1988 | Cleveland et al. |
| 4,791,192 A | 12/1988 | Nakagawa et al. |
| 4,816,567 A | 3/1989 | Cabilly et al. |
| 4,927,762 A | 5/1990 | Darfler |
| 4,965,199 A | 10/1990 | Capon et al. |
| 4,975,278 A | 12/1990 | Senter et al. |
| 5,013,556 A | 5/1991 | Woodle et al. |
| 5,122,469 A | 6/1992 | Mather et al. |
| 5,225,539 A | 7/1993 | Winter |
| 5,807,715 A | 9/1998 | Morrison et al. |
| 6,025,155 A | 2/2000 | Hadlaczky et al. |
| 6,077,677 A | 6/2000 | Hodgson et al. |
| 6,204,023 B1 | 3/2001 | Robinson et al. |
| 6,548,640 B1 | 4/2003 | Winter |
| 2002/0160970 A1 | 10/2002 | Hadlaczky et al. |
| 2003/0028071 A1 | 2/2003 | Handy et al. |
| 2003/0032995 A1 | 2/2003 | Handy et al. |
| 2003/0083293 A1 | 5/2003 | Hadlaczky et al. |

FOREIGN PATENT DOCUMENTS

| | | |
|---|---|---|
| EP | 73657 A1 | 3/1983 |
| EP | 244234 A2 | 11/1987 |
| EP | 402226 A1 | 12/1990 |
| EP | 183070 B1 | 10/1991 |
| EP | 404097 B1 | 9/1996 |
| WO | 8101145 A1 | 4/1981 |
| WO | 8700195 A1 | 1/1987 |
| WO | 8705330 A1 | 9/1987 |
| WO | 8807378 A1 | 10/1988 |
| WO | 9013646 A1 | 11/1990 |
| WO | 9311161 A1 | 6/1993 |
| WO | 9411026 A2 | 5/1994 |
| WO | 9411026 A3 | 8/1994 |
| WO | 9627011 A1 | 9/1996 |
| WO | 9632478 A1 | 10/1996 |
| WO | 2007056858 A1 | 5/2007 |

OTHER PUBLICATIONS

Rudikoff, Giusti, Cook, and Scharff. Single amino acid substitution altering antigen binding specificity. Proceedings of the National Academy of Sciences, 1982. vol. 79, pp. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of "abbreviated" complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti CD4 monoclonal antibody by rational design. Biochemical and Biophysical Research Communications, 2003. vol. 307, pp. 198-205.*

(Continued)

*Primary Examiner* — Anne M. Gussow
(74) *Attorney, Agent, or Firm* — K&L Gates LLP

(57) ABSTRACT

The invention relates to treatment of cancer. More specifically the invention relates to methods of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma and epidermoid carcinoma, by administering antibodies directed to α2β1 integrin.

43 Claims, 10 Drawing Sheets

OTHER PUBLICATIONS

Vajdos, Adams, Breece, Presta, De Vos, and Sidhu. Comprehensive functional maps of the antigen-binding site of an anti ErbB2 antibody obtained with shotgun scanning mutagenesis. Journal of Molecular Biology, 2002. vol. 320, pp. 415-428.*

Holm, Jafari, Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Gura. Systems for identifying new drugs are often faulty. Science, 1997. vol. 278, pp. 1041-1042.*

Bodey, Bodey, Siegel, and Kaiser. Failure of cancer vaccines: the significant limitations of this approach to immunotherapy. Anticancer Research, 2000. vol. 20, pp. 2665-2676.*

Forni, Lollini, Musiani, and Colombo. Immunoprevention of cancer: is the time ripe? Cancer Research, 2000. vol. 60, pp. 2571-2575.*

De Gruijl and Curiel. Cancer vaccine strategies get bigger and better. Nature Medicine, 1999. vol. 5, pp. 1124-1125.*

Chatterjee, Foon, and Kohler. Idiotypic antibody immunotherapy of cancer. Cancer Immunology and Immunotherapy, 1994. vol. 38, pp. 75-82.*

Al-Lazakani et al., J. Mol. Biol., Standard Conformations for the Canonical Structures of Immunoglobulins 273 (4):927-48 (1997).

Andreasen et al., J. Immunol., Expression and Functional Importance of Collagen-Binding Integrins, and on Virus-Activated T Cells 171:2804-2811 (2003).

Zutter et al., Am. J. Pathol., Collagen Receptor Control of Epithelial Morphogenesis and Cell Cycle Progression. 155(3):927-940 (1995).

Zapata et al., Protein Eng., Engineering linear F(ab')2 fragments for efficient production in Escherichia coli and enhanced antiproliferative activity. 8(10): 1057-1062 (1995).

Argraves, W.S, J. Cell. Biol., Amino Acid Sequence of the Human Fibronectin Receptor Sep 105(3):1183-90 (1987).

Avraamides et al., Nat Rev Cancer, Integrins in angiogenesis and lymphangiogenesis Aug. 2008;8(8):604-17.

Bahou et al., Blood, the VLA-2 (a2p1I) Domain Functions as a Ligand-Specific Recognition Sequence for Endothelial Cell Attachment and Spreading: Molecular and Functional Characterization 84 (11):3734-3741(1994).

Barnes et al., Anal. Biochem., Methods for growth of cultured cells in serum-free medium 102: 255 (1980).

Bergelson et al., Cell Adhes. Commun., The I domain is essential for Echovirus 1 interaction with VLA-2 2 (5):455-64 (1994).

Better et al., Science, Escherichia coli secretion of an active chimeric antibody fragment 240(4855):1041-1043 (1988).

Bhatt and Topol, Nat. Rev. Drug Discov., Scientific and Therapeutic Advances in Antiplatelet Therapy 2(1):15-28 (2003).

Brennan et al., Science, Preparation of bispecific antibodies by chemical recombination of monoclonal immunoglobulin G1 fragments 229:81 (1985).

Yaniv, Nature, Enhancing elements for activation of eukaryotic promoters. 297: 17-18 (1982).

Caron et al., J. Exp. Med., Engineered humanized dimeric forms of IgG are more effective antibodies 176:1191-1195 (1992).

Carter et al., Nature BioTechnology, High Level Escherichia coli Expression and Production of a Bivalent Humanized Antibody Fragment 10: 163-167 (1992).

Champe et al., J. Biol. Chem., Monoclonal antibodies that block the activity of leukocyte function-associated antigen 1 recognize three discrete epitopes in the inserted domain of CD11a 270:1388-1394 (1995).

Chan et. al., J. Immunol., T Cell Receptor-Dependent, Antigen-Specific Stimulation of a Murine T Cell Clone Induces a Transient, VLA Protein-Mediated Binding to Extracellular Matrix. 147:398-404 (1991).

Cheng and Prusoff, Biochem. Pharmacol., Relationship between the inhibition constant (Ki) and the concentration of inhibitor which causes 50 per cent inhibition (IC50) of an enzymatic reaction 22(23):3099-108(1973).

Chothia and Lesk J. Mol. Biol., Canonical structures for the hypervariable regions of immunoglobulins 196: 901-917 (1987).

Chothia et al., J. Mol. Biol., Domain association in immunoglobulin molecules. The packing of variable domains 186 (3):651-63 (1985).

Chothia et al., Nature, Conformations of immunoglobulin hypervariable regions 342(6252):877-83 (1989).

Clackson et al., Nature, Making antibody fragments using phase display libraries 352:624-628 (1991).

Cunningham and Wells; Science, High resolution epitope mapping of hGH-receptor interactions by alanine scanning mutagenesis 244: 1081-1085 (1989).

Wu and Santoro, Dev. Dyn., Differential expression of integrin alpha subunits supports distict roles during lung branching morphogenesis. 206:169-171 (1994).

de Fougerolles et. al., J. Clin. Invest., Regulation of inflammation by collagen binding integrins alpha1beta1 and alpha2beta1 in models of hypersensitivity and arthritis 105:721-720 (2000).

Dickeson et al, Cell Adhesion and Communication, Binding of the alpha2 integrin I domain to extracellular matrix ligands: structural and mechanistic differences between collagen and laminin binding 5: 273-281 (1998).

Dickeson et al, J Biol. Chem., Contributions of the I and EF hand domains to the divalent cation-dependent collagen binding activity of the alpha2beta1 integrin 272: 7661-7668 (1997).

Dustin and de Fougerolles, Curr Opin Immunol, Reprograming T cells: the role of extracellular matrix in coordination of T cell activation and migration 13:286-290 (2001).

Eble J.A., Curr. Phar. Des., Collagen-Binding Integrins as Pharmaceutical Targets 11(7):867-880 (2005).

Edelson et al., Blood, Novel collectin/C1q receptor mediates mast cell activation and innate immunity 107(1): 143-50 (2006).

Edelson et al., Blood, Mast cell mediated inflammatory responses require the alpha2beta1 integrin. 103: 2214-20 (2004).

Edge et al., Anal. Biochem., Deglycosylation of glycoproteins by trifluoromethanesulfonic acid 118: 131 (1981).

Emsley et al., J. Biol. Chem., Crystal Structure of the I Domain from Integrin alpha2beta1. 272:28512 (1997).

Emsley et al.,Cell, Structural Basis of Collagen Recognition by Integrin alpha2beta1. 101:47 (2000).

Epstein et al., Proc. Natl. Acad. Sci. USA, Biological activity of liposome-encapsulated murine interferon gamma is mediated by a cell membrane receptor. 82: 3688 (1985).

Evan et al., Mol. Cell. Biol., Isolation of monoclonal antibodies specific for human c-myc proto-oncogene product. 5 (12):3610-3616 (1985).

Field et al., Mol. Cell. Biol., Purification of a RAS-responsive adenylyl cyclase complex from Saccharomyces cerevisiae by use of an epitope addition method. 8: 2159-2165 (1988).

Fleer et al., Nature BioTechnology, Stable Multicopy Vectors for High-Level Secretion of Recombinant Human Serum Albumin by Kluyveromyces Yeasts. 9: 968-975 (1991).

Foote and Winter, J. Mol. Biol., Antibody framework residues affecting the conformation of the hypervariable loops. 224: 487 (1992).

Gabizon et al., J. National Cancer Inst., Pharmacokinetics and Tissue Distribution of Doxorubicin Encapsulated in Stable Liposomes With Long Circulation Times. 81(19): 1484 (1989).

Gadek et al., Science, Generation of an LFA-1 Antagonist by the Transfer of the ICAM-1 Immunoregulatory Epitope to a Small Molecule. 295(5557):1086-9 (2002).

Gendron, J. Biol. Chem., Integrin alpha2beta1 Inhibits Fas-mediated Apoptosis in T Lymphocytes by Protein Phosphatase 2A-dependent Activation of the MAPK/ERK Pathway. 278:48633-48643 (2003).

Giltay et al., Blood, Human vascular endothelial cells express a membrane protein complex immunochemically indistinguishable from the platelet VLA-2 (glycoprotein Ia-IIa) complex. 73(5):1235-41 (1989).

Wolff et al., Cancer Research, Monoclonal antibody homodimers: enhanced antitumor activity in nude mice. 53:2560-2565 (1993).

Graham et al., J. Gen Virol., Characteristics of a Human Cell Line Transformed by DNA from Human Adenovirus Type 5. 36: 59 (1977).

Gruber et al., J. Immunol., Efficient tumor cell lysis mediated by a bispecific single chain antibody expressed in Escherichia coli. 152:5368 (1994).
Gruner et al., Blood, Multiple integrin-ligand interactions synergize in shear-resistant platelet adhesion at sites of arterial injury in vivo. 102:4021-4027 (2003).
Guss et al, EMBO J., Structure of the IgG-binding regions of streptococcal protein G. 5: 1567-1575 (1986).
Hakimuddin, et al., Arch. Biochem. Biophys., A chemical method for the deglycosylation of proteins. 259: 52 (1987).
Ham et al., Meth. Enz., Media and growth requirements. 58: 44 (1979).
Shalaby et al., J. Exp. Med., Development of Humanized Bispecitic Antibodies Reactive with Cytotoxic Lymphocytes and Tumor Cells Overexpressing the HER2 Protooncogene. 175:217-225 (1992).
Shawler et al., J. Immunol., Human immune response to multiple injections of murine monoclonal IgG. 135(2):1530 (1985).
Shopes, B.J. Immunol., A genetically engineered human IgG mutant with enhanced cytolytic activity. 148:2918-2922 (1992).
Siljander et al., Blood, Platelet receptor interplay regulates collagen-induced thrombus formation in flowing human blood. 103(4):1333-1341 (2004).
Sircar et al., Bioorg. Med. Chem., Synthesis and SAR of N-Benzoyl-L-Biphenylalanine Derivatives: Discovery of TR-14035, A Dual alpha4beta7/alpha4beta1 Integrin Antagonisty. 10:2051-2066 (2002).
Verhoyen et al., Science, Reshaping human antibodies: Grafting an antilysozyme activity. 239(4847):1534-6 (1988).
Stevenson et al., Anti-Cancer Drug Design, A Chimeric antibody with dual Fc regions (bisFabFc) prepared by manipulations at the IgG hinge. 3:219-230 (1989).
Stinchcomb et al., Nature, Isolation and characterisation of a yeast chromosomal replicator. 282: 39 (1979).
Symington et al., J. Cell Biol., Interaction of Integrins and alpha2beta1: Potential Role in Keratinocyte Intercellular Adhesion. 120(2):523-35 (1993).
Urlaub et al., Proc. Natl. Acad. Sci. USA, Isolation of Chinese hamster cell mutants deficient in dihydrofolate reductase activity. 77: 4216 (1980).
Takada and Hemler J. Cell Biol., The Primary Structure of the VLA-2/Collagen Receptor alpha2 Subunit (Platelet GPIa): Homology to Other Integrins and the Presence of a Possible Collagen-binding Domain. 109(1):397-407 (1989).
Tempest et al., Biotechnology (NY), Reshaping a human monoclonal antibody to inhibit human respiratory syncytial virus infection in vivo. 9(3):266-71 (1991).
Thotakura et al., Meth. Enzymol., Enzymatic deglycosylation of glycoproteins. 138: 350 (1987).
Tutt et al., J. Immunol., Trispecific F(ab')3 Derivatives That Use Cooperative Signaling Via the TCR/CD3 Complex and CD2 to Activate and Redirect Resting Cytotoxic T Cells. 147:60 (1991).
Hangan et al. Cancer Res., Integrin VLA-2 (alpha2beta1) function in postextravasation movement of human Rhabdomyosarcoma RD cells in the liver. 56:3142-3149 (1996).
Hemler, Annu Rev Immunol., VLA proteins in the integrin family. Structures, functions and their role on leukocytes. 8:365:365-400 (1999).
Hollinger et al., Proc. Natl. Acad. Sci. USA, Diabodies: small bivalent and bispecific antibody fragments. 90: 6444-6448 (1993).
Hwang et al., Proc. Natl. Acad. Sci. USA, Hepatic uptake and degradation of unilamellar sphingomyelin/cholesterol liposomes: a kinetic study. 77: 4030 (1980).
Jackson et al., J. Med. Chem., Potent alpha4beta1 Peptide Antagonists as Potential Anti-Inflammatory Agents. 40:3359-3368 (1997).
Jones et al., Nature, Replacing complementarity determining regions in a human antibody with those from a mouse. 321(6069):522-5 (1986).
Jones, Genetics, Proteinase Mutants of Saccharomyces Cerevisiae. 85:23-33 (1977).
Kabat et al, J. Biol. Chem., Unusual Distributions of Amino Acics in Complementaritydetermining (Hypervariable) Segments of Heavy and Light Chains of Immunoglobulins and Their Possible Roles in Specificity of Antibody-combining Sites. 252:6609-6616 (1977).

Wilman, Biochemical Society Transactions, Prodrugs in Cancer Chemotherapy. 14, pp. 375-382 (1986).
Karat, Adv. Protein Chem., The structural basis of antibody complementarity. 32:1-75 (1978).
Kamata et al., J Biol. Chem., Identification of Putative Ligand Binding Sites within I Domain of Integrin a2pl (VLA-2, CD49b/CD29. 269:9659-9663(1994).
Keely et. al., J. Cell Sci., Alteration of collagen-dependent adhesion, motility, and morphogenesis by the expression of antisense alpha2 integrin mRNA in mammary cells. 108:595-607 (1995).
Kohler et al., Nature, Continuous cultures of fused cells secreting antibody of predefined specificity. 256:495 (1975).
Kostgelny et al., J. Immunol., Formation of a bispecific antibody by the use of leucine zippers. 148(5):1547-1553 (1992).
Kozbor, J. Immunol., A human hybrid myeloma for production of human monoclonal antibodies. 133: 3001 (1984).
Kriegelstein et al., J. Clin. Invest., Collagen-binding integrin $\alpha 1\beta 1$ regulates intestinal inflammation in experimental colitis. 110(12):1773-82 (2002).
Languino et al., J Cell Bio., Endothelial Cells Use alpha2beta1 Integrin as a Laminin Receptor. 109:2455-2462 (1989).
Vanhoorelbeke et al., Curr. Drug Targets Cardiovasc. Haernatol. Disord., Inhibition of Platelet Adhesion to Collagen as a New Target for Antithrombotic Drugs. 3(2):123-40 (2003).
Lindenbaum, et al., Nucleic Acids Research, A mammalian artificial chromosome engineering system (ACE System) applicable to biopharmaceutical protein production, transgenesis and gene-based cell therapy. 32 (21): e172 (2004).
Lindmark et al., J. Immunol. Meth., Binding of immunoglobulins to protein A and immunoglobulin levels in mammalian sera. 62:1-13 (1983).
Marks et al., J. Mol. Biol., By-passing immunization : Human antibodies from V-gene libraries displayed on phage. 222:581-597 (1991).
Martin et al., J. Biol. Chem., Irreversible coupling of immunoglopulin fragments to preformed vesicles. An improved method for liposome targeting. 257: 286-288 (1982).
Martin et al., Methods Enzymol., Molecular modeling of antibody combining sites. 203, 121-153 (1991).
Martin et al., Proc. Natl Acad. Sci. USA, Modeling Antibody Hypervariable Loops: A Combined Algorithm. 86, 9268-9272 (1989).
Massey, Nature, Catalytic antibodies catching on. 328: 457-458 (1987).
Mather et al., Annals N.Y Acad. Sci., Culture of testicular cells in hormone-supplemented serum-free medium. 383: 44-68 (1982).
Mather, Biol. Reprod., Establishment and characterization of two distinct mouse testicular epithelial cell lines. 23: 243-252 (1980).
Mazurov et al., Thromb. Haemost., A monoclonal antibody, VM64, reacts with a 130 kDa glycoprotein common to platelets and endothelial cells: heterogeneity in antibody binding to human aortic endothelial cells. 66(4):494-9 (1991).
Mendrick and Kelly, Lab Invest., Temporal expression of VLA-2 and modulation of its ligand specificity by rat glomerular epithelial cells in vitro. 69(6):690-702 (1993).
Merlini et al., Circulation, Thrombocytopenia Caused by Abciximab or Tirofiban and Its Association With Clinical Outcome in Patients Undergoing Coronary Stenting. 109:2203-2206 (2004).
Morimoto et al., Journal of Biochemical and Biophysical Methods, Single-step purification of F(ab')2 fragments of mouse monoclonal antibodies (immunoglobulins G1) by hydrophobic interaction high performance liquid chromatography using TSKgel Phenyl-5PW. 24: 107-117 (1992).
Morrison et al, Proc. Natl. Acad. Sci. USA, Chimeric human antibody molecules: mouse antigen-binding domains with human constant region domains. 81:6851-6855 (1984).
Munson et al., Anal. Biochem., LIGAND: A versatile computerized approach for characterization of ligand-binding systems. 107: 220 (1980).
Neuberger et al., Nature, Recombinant antibodies possessing novel effector functions. 312: 604-608 (1984).
Nieswandt and Watson, Blood, Platelet-collagen interaction: is GPVI the central receptor? 102(2):449-461 (2003).

Paborsky et al., Protein Engineering, Mammalian cell transient expression of tissue factor for the production of antigen. 3(6): 547-553 (1990).

Pascual and Capra Adv. Immunol., Human immunoglobulin heavy-chain variable region genes: Organization, polymorphism and expression. 49:1-74 (1991).

Pedersen et al., Immunomethods, Antibody Modeling: Beyond Homology. 1, 126 (1992).

Werr et al., Blood, Integrin alpha2beta1 (VLA-2) is a principal receptor used by neutrophils for locomotion in extravascular tissue. 95:1804-1809 (2000).

Pilcher et. al., J. Biol. Chem., Cell Type-specific Inhibition of Keratinocyte Collagenase-1 Expression by Basic Fibroblast Growth Factor and Keratinocyte Growth Factor: A Common Receptor Pathway. 272:18147-54 (1997).

Wayner et al., J. Cell Biol., The function of multiple extracellular matrix receptors in mediating cell adhesion to extracellular matrix: preparation of monoclonal antibodies to the fibronectin receptor that specifically inhibit cell adhesion to fibronectin and react with platelet glycoproteins Ic-IIa. 107(5):1881-91 (1988).

Queen et al., Proc. Natl. Acad. Sci. USA, A humanized antibody that binds to the interleukin-2 receptor. 86:10029 (1989).

Rao et al., J. Immunol., Potent Costimulation of Effector T Lymphocytes by Human Collagen Type I. 165(9):4935-40 (2000).

Reichman et al., Nature, Reshaping human antibodies for therapy. 332(6162):323-7 (1988).

Vitetta et al., Science, Redesigning nature's poisons to create anti-tumor reagents. 238:1098 (1987).

Reyes et al., Nature, Expression of human beta-interferon cDNA under the control of a thymidine kinase promoter from herpes simplex virus. 297: 598-601 (1982).

Santoro et al., Thromb. Haemost., The alpha2beta1 integrin: A collagen receptor on platelets and other cells. 74:813-821 (1995).

Schell et al., Ann. Hematol., Thrombocytopenia associated will c7E3 Fab (abciximab). 81:76-79 (2002).

Senger et al., Am. J. Pathol., The alpha1beta1 and alpha2beta1 Integrins Provide Critical Support for Vascular Endothelial Growth Factor Signaling, Endothelial Cell Migration, and Tumor Angiogenesis. 160(1):195-204 (2002).

Senger et al., PNAS, Angiogenesis promoted by vascular endothelial growth factor: Regulation through aipha1beta1 and alpha2beta1 integrins. 94(25): 13612-7 (1997).

* cited by examiner

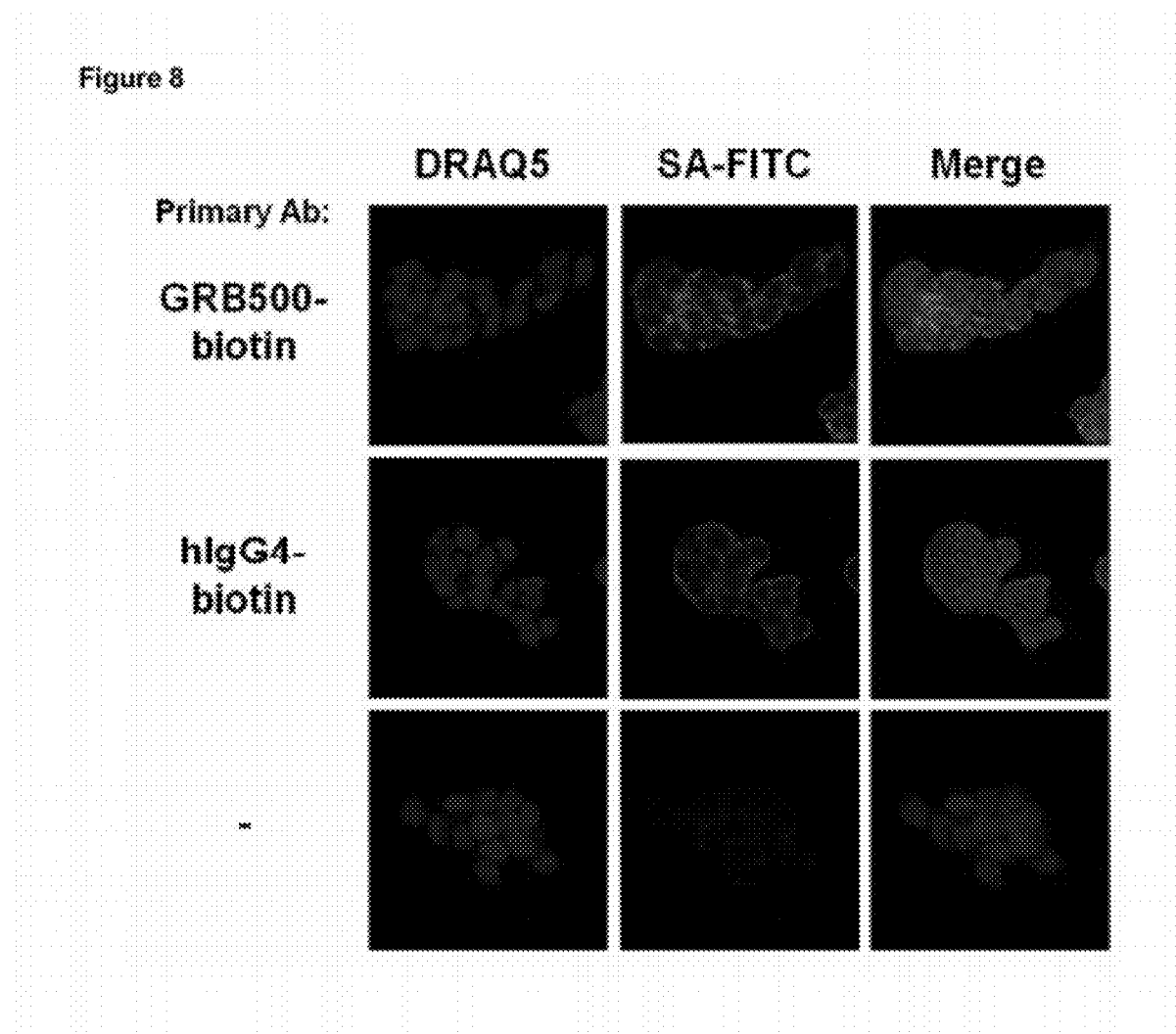

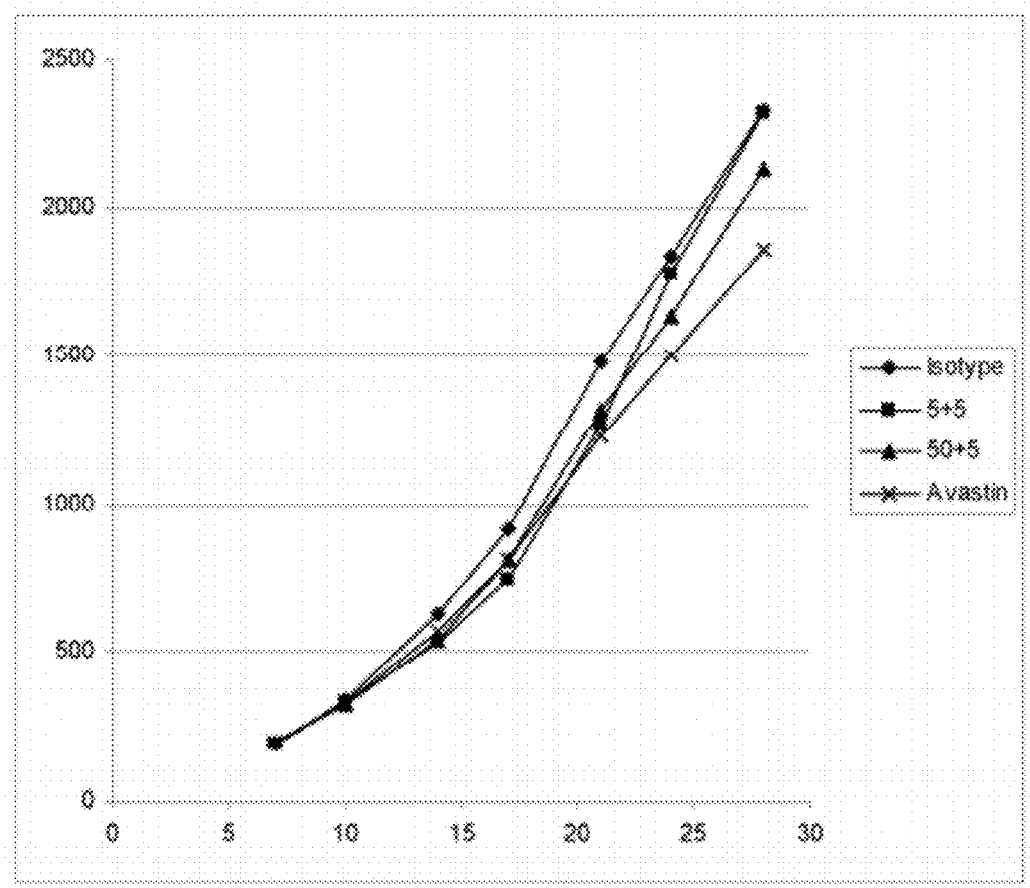

TREATMENT WITH ANTI-ALPHA2 INTEGRIN ANTIBODIES

TECHNICAL FIELD

The present invention relates to treatment of cancer. More specifically the invention relates to methods of treating cancer by administering antibodies directed to α2β1 integrin.

BACKGROUND OF THE INVENTION

The integrin α2β1 (Very late antigen 2; VLA-2) is expressed on a variety of cell types including platelets, vascular endothelial cells, epithelial cells, activated monocytes/macrophages, fibroblasts, leukocytes, lymphocytes, activated neutrophils and mast cells. (Hemler, Annu Rev Immunol 8:365:365-400 (1999); Wu and Santoro, Dev. Dyn. 206:169-171 (1994); Edelson et. al., Blood. 103(6):2214-20 (2004); Dickeson et al, Cell Adhesion and Communication. 5: 273-281 (1998)). The most typical ligands for α2β1 include collagen and laminin, both of which are found in extracellular matrix. Typically the I-domain of the α2 integrin binds to collagen in a divalent-cation dependent manner whereas the same domain binds to laminin through both divalent-cation dependent and independent mechanisms. (Dickeson et al, Cell Adhesion and Communication. 5: 273-281 (1998)) The specificity of the α2β1 integrin varies with cell type and serves as a collagen and/or laminin receptor for particular cell types, for example α2β1 integrin is known as a collagen receptor for platelets and a laminin receptor for endothelial cells. (Dickeson et al, J. Biol. Chem. 272: 7661-7668 (1997)) Echovirus-1, decorin, E-cadherin, matrix metalloproteinase I (MMP-I), endorepellin and multiple collectins and the C1q complement protein are also ligands for α2β1 integrin. (Edelson et al., Blood 107(1): 143-50 (2006)) The α2β1 integrin has been implicated in several biological and pathological processes including collagen-induced platelet aggregation, cell migration on collagen, cell-dependent reorganization of collagen fibers as well as collagen-dependent cellular responses that result in increases in cytokine expression and proliferation, (Gendron, J. Biol. Chem. 278:48633-48643 (2003); Andreasen et al., J. Immunol. 171:2804-2811 (2003); Rao et al., J. Immunol. 165(9):4935-40 (2000)), aspects of T-cell, mast cell, and neutrophil function (Chan et. al., J. Immunol. 147:398-404 (1991); Dustin and de Fougerolles, Curr Opin Immunol 13:286-290 (2001), Edelson et. al., Blood. 103(6):2214-20 (2004), Werr et al., Blood 95:1804-1809 (2000), aspects of delayed type hypersensitivity contact hypersensitivity and collagen-induced arthritis (de Fougerolles et. al., J. Clin. Invest. 105:721-720 (2000); Kriegelstein et al., J. Clin. Invest. 110(12):1773-82 (2002)), mammary gland ductal morphogenesis (Keely et. al., J. Cell Sci. 108:595-607 (1995); Zutter et al., Am. J. Pathol. 155(3):927-940 (1995)), epidermal wound healing (Pilcher et. al., J. Biol. Chem. 272:181457-54 (1997)), and processes associated with VEGF-induced angiogenesis (Senger et al., Am. J. Pathol. 160(1):195-204 (2002)).

Integrin/ligand interactions can facilitate leukocyte extravasation into inflamed tissues (Jackson et al., J. Med. Chem. 40:3359-3368 (1997); Gadek et al., Science 295(5557):1086-9 (2002), Sircar at al., Bioorg. Med. Chem. 10:2051-2066 (2002)), and play a role in downstream events following the initial extravasation of leukocytes from the circulation into tissues in response to inflammatory stimuli, including migration, recruitment and activation of pro-inflammatory cells at the site of inflammation (Eble J. A., Curr. Phar. Des. 11(7):867-880 (2005)). Some antibodies that block α2β1 integrin were reported to show impact on delayed hypersensitivity responses and efficacy in a murine model of rheumatoid arthritis and a model of inflammatory bowel disease (Kriegelstein et al., J. Clin. Invest. 110(12):1773-82 (2002); de Fougerolles et. al., J. Clin. Invest. 105:721-720 (2000) and were reported to attenuate endothelial cell proliferation and migration in vitro (Senger et al., Am. J. Pathol. 160(1):195-204 (2002), suggesting that the blocking of α2β1 integrin might prevent/inhibit abnormal or higher than normal angiogenesis, as observed in various cancers.

α2β1 integrin is the only collagen-binding integrin expressed on platelets and has been implicated to play some role in platelet adhesion to collagen and hemostasis (Gruner et al., Blood 102:4021-4027 (2003); Nieswandt and Watson, Blood 102(2):449-461 (2003); Santoro et al., Thromb. Haemost. 74:813-821 (1995); Siljander et al., Blood 15:1333-1341 (2004); Vanhoorelbeke at al., Curr. Drug Targets Cardiovasc. Haematol. Disord. 3(2):125-40 (2003)). In addition, platelet α2β1 may play a role in the regulation of the size of the platelet aggregate (Siljander et al., Blood 103(4):1333-1341 (2004)).

α2β1 integrin has also been shown as a laminin-binding integrin expressed on endothelial cells (Languino et al., J Cell Bio. 109:2455-2462 (1989)). Endothelial cells are thought to attach to laminin through an integrin-mediated mechanism, however it has been suggested that the α2 I domain may function as a ligand-specific sequence involved in mediating endothelial cell interactions (Bahou et al., Blood. 84(11): 3734-3741 (1994)).

It is anticipated that a therapeutic antibody that binds α2β1 integrin, including the α2β1 integrin on platelets, could result in bleeding complications. For example, antibodies targeting other platelet receptors such as GPIb (Vanhoorelbeke et al., Curr. Drug Targets Cardiovasc. Haematol. Disord. 3(2):125-40 (2003) or GP IIb/IIIa (Schell at al., Ann. Hematol. 81:76-79 (2002), Nieswandt and Watson, Blood 102(2):449-461 (2003), Merlini et al., Circulation 109:2203-2206 (2004)) have been associated with thrombocytopenia, although the mechanisms behind this are not well understood. It has been hypothesized that binding of an antibody to a platelet receptor can alter its three dimensional structure, and expose normally unexposed epitopes which then leads to platelet elimination (Merlini et al., Circulation 109:2203-2206 (2004). Indeed, the bleeding complications associated with oral doses of GP IIa/IIIb antagonists have been described as the "dark side" of this class of compounds (Bhatt and Topol, Nat. Rev. Drug Discov. 2(1):15-28 (2003)).

The anti-human α2β1 integrin blocking antibody BHA2.1 was first described by Hangan et al., (Cancer Res. 56:3142-3149 (1996)). Other anti-α2β1 integrin antibodies are known and have been used in vitro, such as the commercially available antibodies AK7 (Mazurov et al., Thromb. Haemost. 66(4):494-9 (1991), P1E6 (Wayner et al., J. Cell Biol. 107(5): 1881-91 (1988)), 10G11 (Giltay et al., Blood 73(5):1235-41 (1989) and A2-11E10 (Bergelson et al., Cell Adhes. Commun. 2(5):455-64 (1994). Hangan et al., (Cancer Res. 56:3142-3149 (1996)) used the BHA2.1 antibody in vivo to study the effects of blocking α2β1 integrin function on the extravasation of human tumor cells in the liver, and the ability of these tumor cells to develop metastatic foci under antibody treatment. The Ha1/29 antibody (Mendrick and Kelly, Lab Invest. 69(6):690-702 (1993)), specific for rat and murine α2β1 integrin, has been used in vivo to study the upregulation of α2β1 integrin on T cells following LCMV viral activation (Andreasen et al., J. Immunol. 171:2804-2811 (2003)), to study SRBC-induced delayed type hypersensitivity and FITC-induced contact type-hypersensitivity responses and collagen-induced arthritis (de Fougerolles et. al., J. Clin. Invest. 105:721-720 (2000)), to study the role of α2β1 integrin in VEGF regulated angiogenesis (Senger et al., Am. J. Pathol. 160(1):195-204 (2002); Senger et al., PNAS 94(25): 13612-7 (1997)), and to study the role of α2β1 integrin in PMN locomotion in response to platelet activating factor (PAF) (Werr et al., Blood 95:1804-1809 (2000)).

The use of murine monoclonal antibodies, such as those described above, as human therapeutic agents in non-immunocompromized patients has been limited by the robust immune responses directed against administered murine antibodies, particularly in repeated administration. This response cannot only curtail the effective half-life of the murine antibody in circulation but also can lead to profound injection site and/or anaphylactic responses (Shawler et al., J. Immunol. 135(2):1530 (1985)). In addition, the rodent effector functions associated with the constant regions (Fc) are much less effective than their human counterparts when administered to humans, resulting in a loss of potentially desirable complement activation and antibody-dependent, cell-mediated cytotoxicity (ADCC) activity.

BRIEF DESCRIPTION OF THE DRAWINGS

FIG. 8: Confocal microscopy images of stained cell line SW480.

FIG. 9: Effect of GBR500 against the A549 non small cell lung cancer xenograft in nu/nu athymic mice.

SUMMARY OF THE INVENTION

Figure 1:
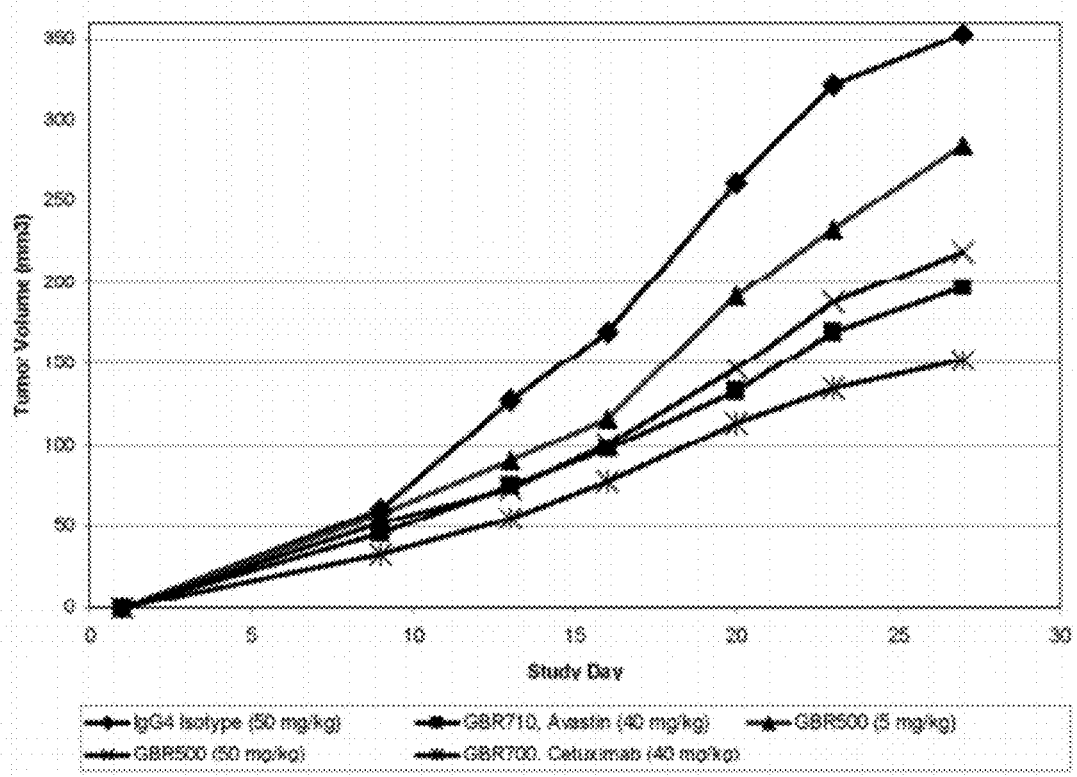
FIG. 1: Effect of GBR500 on AsPC-1 human pancreatic cancer xenograft growth in immunodeficient female BALB/c nude (nu/nu) athymic mice.

The present invention concerns methods of using humanized anti-alpha 2 (α2) integrin antibodies for treating cancers. In particular, the invention provides an effective approach for treating cancers selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma. This invention is based on the unexpected results that anti-alpha 2 (α2) integrin antibodies which bind specifically α2β1 integrin inhibit tumor growth to a degree comparable to anti-VEGF antibodies. VEGF factors activate or upregulate expression of integrins such as α1β1, α2β1, α4β1, α5β1 and αv/β3 on blood vessels and α4β, α9β1, α2β1 and α1/β1 on lymphatic vessels (Avraamides et al., Nat Rev Cancer. 2008 August; 8(8):604-17). It is therefore surprising that antagonism of only α2β1 leads to a similar outcome as treatment with a VEGF antibody.

Accordingly in one aspect, the invention provides a method of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma, comprising administering to a subject a therapeutically effective amount of a humanized anti-α2 integrin antibody comprising a heavy chain variable region comprising the amino acid sequence of (a) HCDR2 (VIWARGFTNYN-SALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40 and/or a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6).

In another aspect the invention provides a method of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma, comprising administering to a subject a composition comprising a therapeutically effective amount of a humanized anti-α2 integrin antibody comprising a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40 and/or a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6) and a pharmaceutically acceptable carrier. Compositions for therapeutic uses may be sterile and may be lyophilized.

In another aspect the invention provides a method of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma, comprising administering to a subject a composition comprising a therapeutically effective amount of a humanized anti-α2 integrin antibody comprising a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40 and/or a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6) and a pharmaceutically acceptable carrier, whereas the dosage regime is once every two weeks.

In yet a further aspect, the invention provides a humanized anti-α2 integrin antibody comprising a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40 and/or a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6) or a composition comprising said humanized anti-α2 integrin antibody and a pharmaceutically acceptable carrier for use in a method for the treatment of cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma fibrosarcoma, osteosarcoma, and epidermoid carcinoma.

In a further aspect the invention provides a kit for treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL);

acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma in a human patient comprising a package comprising a humanized anti-α2 integrin antibody composition comprising a humanized anti-α2 integrin antibody comprising a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40 and/or a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6) and instructions for using said humanized anti-α2 integrin antibody for said treatment.

In a further aspect the invention provides an article of manufacture comprising a humanized anti-α2 integrin antibody comprising a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40 and/or a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6) a container and a label indicating the use of said humanized anti-α2 integrin antibody for treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma.

In certain embodiments, the anti-α2 integrin antibody includes one or more human constant regions (e.g., $C_L$ and/or $C_H$) and a light chain variable region comprising the amino acid sequence of SEQ ID NO:19 and/or a heavy chain variable region comprising the amino acid sequence of SEQ ID NO:21 or amino acid sequence variants thereof. Various forms of the antibody are contemplated herein. For example, the anti-α2 integrin antibody may be a full length antibody (e.g., comprising human immunoglobulin constant regions) or an antibody fragment (e.g. Fab or F(ab')$_2$ or Fab' or Fv or scFv fragments). Furthermore, the antibody may be labeled with a detectable label, immobilized on a solid phase and/or conjugated with a heterologous compound (such as a cytotoxic agent).

In an embodiment, the above-mentioned heavy chain variable region comprises the amino acid sequence of SEQ ID NO:185.

In a further embodiment, the above-mentioned heavy chain variable region comprises the amino acid sequence of SEQ ID NO:185 in which position 30 is Thr and/or position 31 is Asn.

In a further embodiment, the above-mentioned heavy chain variable region comprises the amino acid sequence of SEQ ID NO:185 in which (a) position 71 is Lys, (b) position 73 is Asn, (c) position 78 is Val, or (d) any combination of (a)-(c).

In a further embodiment, the above-mentioned heavy chain variable region comprises an amino acid sequence selected from SEQ ID NOs:70-79 and SEQ ID NOs:109-111.

In a further embodiment, the above-mentioned heavy chain variable region comprises an amino acid sequence selected from SEQ ID NOs:70-75, SEQ ID NOs:77-79 and SEQ ID NOs:109-111.

In an embodiment, the above-mentioned heavy chain variable region further comprises a FW4 region comprising the amino acid sequence WGQGTLVTVSS (SEQ ID NO:13).

In an embodiment, the above-mentioned heavy chain variable region comprises the amino acid sequence of HCDR1 (SEQ ID NO:1), HCDR2 (SEQ ID NO:2) and HCDR3 (SEQ ID NO:3).

In a further embodiment, the above-mentioned humanized anti-α2 integrin antibody comprises a heavy chain comprising SEQ ID NO:187.

In an embodiment, the above-mentioned light chain variable region comprises the amino acid sequence of SEQ ID NO:186.

In an embodiment, the above-mentioned light chain variable region comprises the amino acid sequence of SEQ ID NO:186 in which the asparagine (N) at amino acid position 26 is replaced by glutamine (Q).

In an embodiment, the above-mentioned light chain variable region comprises the amino acid sequence of SEQ ID NO:186 in which (a) position 2 is Phe, (b) position 45 is Lys, (c) position 48 is Tyr, or (d) any combination of (a)-(c).

In an embodiment, the above-mentioned light chain variable region comprises an amino acid sequence selected from SEQ ID NO:41, SEQ ID NOs:80-92 and SEQ ID NO:108.

In an embodiment, the above-mentioned light chain variable region comprises an amino acid sequence selected from SEQ ID NOs:90-92.

In an embodiment, the above-mentioned light chain variable region further comprises a FW4 region comprising the amino acids sequence FGQGTKVEIK (SEQ ID NO:38).

In an embodiment, the above-mentioned light chain variable region comprises the amino acid sequence of LCDR1 (SEQ ID NO:4), LCDR2 (SEQ ID NO:5) and LCDR3 (SEQ ID NO:6).

In an embodiment, the above-mentioned light chain variable region comprises the amino acid sequence of LCDR1 (SEQ ID NO:112), LCDR2 (SEQ ID NO:5) and LCDR3 (SEQ ID NO:6).

In a further embodiment, the above-mentioned humanized anti-α2 integrin antibody comprises a light chain comprising SEQ ID NO:188.

In a further embodiment the above-mentioned humanized anti-α2 integrin antibody comprises:
(i) a heavy chain variable region comprising the amino acid sequence of (a) HCDR2 (VIWARGFTNYNSALMS, SEQ ID NO:2), (b) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (c) SEQ ID NO:40; and
(ii) a light chain variable region comprising the amino acid sequence of (a) an LCDR1 selected from SANSSVNYIH (SEQ ID NO:4) or SAQSSWNYIH (SEQ ID NO:112), (b) LCDR2 (DTSKLAS; SEQ ID NO:5) and (c) LCDR3 (QQWTTNPLT, SEQ ID NO:6).

In a further embodiment the above-mentioned humanized anti-α2 integrin antibody comprises:
(i) a heavy chain variable region comprising the amino acid sequence of (a) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (b) SEQ ID NO:40; and
(ii) a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6).

In a further embodiment the above-mentioned humanized anti-α2 integrin antibody comprises:
(i) a heavy chain variable region comprising the amino acid sequence of HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3); and
(ii) a light chain variable region comprising the amino acid sequence of LCDR1 (SAQSSVNYIH, SEQ ID NO:112), LCDR2 (DTSKLAS; SEQ ID NO:5) and LCDR3 (QQWTTNPLT, SEQ ID NO:6).

Also provided is the above-mentioned method comprising the humanized anti-α2 integrin antibody, wherein (a) the heavy chain variable region comprises the amino acid sequence of SEQ ID NO:185, (b) the light chain variable region comprises the amino acid sequence of SEQ ID NO:186, or (c) both (a) and (b).

Also provided is the above-mentioned method comprising the humanized anti-α2 integrin antibody, wherein (a) the heavy chain variable region comprises the amino acid sequence of SEQ ID NO:185 in which position 30 is Thr and/or position 31 is Asn; (b) the light chain variable region comprises the amino acid sequence of SEQ ID NO:186 in which the asparagine (N) at amino acid position 26 is replaced by glutamine (Q); or (c) both (a) and (b).

Also provided is the above-mentioned method comprising the humanized anti-α2 integrin antibody, wherein (i) the heavy chain variable region comprises the amino acid sequence of SEQ ID NO:185 in which (a) position 71 is Lys, (b) position 73 is Asn, (c) position 78 is Val, or (d) any combination of (a)-(c); (ii) the light chain variable region comprises the amino acid sequence of SEQ ID NO:186 in which (a) position 2 is Phe, (b) position 45 is Lys, (c) position 48 is Tyr, or (d) any combination of (a)-(c); or (iii) both (i) and (ii).

Also provided is the above-mentioned method comprising the humanized anti-α2 integrin antibody, wherein (a) the heavy chain variable region comprises an amino acid sequence selected from SEQ ID NOs:70-79 and SEQ ID NOs:109-111; (b) the light chain variable region comprises an amino acid sequence selected from SEQ ID NO:41, SEQ ID NOs:80-92 and SEQ ID NO:108; or (c) both (a) and (b).

Also provided is the above-mentioned method comprising the humanized anti-α2 integrin antibody, wherein (a) the heavy chain variable region comprises an amino acid sequence selected from SEQ ID NOs:70-75, SEQ ID NOs: 77-79 and SEQ ID NOs:109-111; (b) the light chain variable region comprises an amino acid sequence selected from SEQ ID NOs:90-92; or (c) both (a) and (b).

Also provided is the above-mentioned method comprising the humanized anti-α2 integrin antibody, wherein the humanized anti-α2 integrin antibody comprises a heavy chain comprising SEQ ID NO:187 and a light chain comprising SEQ ID NO:188.

Also provided is the above-mentioned method comprising the humanized anti-α2 integrin antibody, wherein the humanized anti-α2 integrin antibody comprises a heavy chain comprising SEQ ID NO:174 or SEQ ID NO:176 and a light chain comprising SEQ ID NO:178.

In an embodiment, the above-mentioned anti-α2 integrin antibody recognizes the I domain of human α2 integrin.

In an embodiment, the above-mentioned anti-α2 integrin antibody binds α2β1 integrin.

In an embodiment, the above-mentioned anti-α2 integrin antibody binds an epitope of α2 integrin, the epitope comprising:
(a) a Lys residue corresponding to position 192 of the α2 integrin amino acid sequence set forth in SEQ ID NO:8 or position 40 of the α2 integrin I domain amino acid sequence set forth in SEQ ID NO:11;
(b) an Asn residue corresponding to position 225 of the α2 integrin amino acid sequence set forth in SEQ ID NO:8 or position 73 of the α2 integrin I domain amino acid sequence set forth in SEQ ID NO:11;
(c) a Gln residue corresponding to position 241 of the α2 integrin amino acid sequence set forth in SEQ ID NO:8 or position 89 of the α2 integrin I domain amino acid sequence set forth in SEQ ID NO:11;
(d) a Tyr residue corresponding to position 245 of the α2 integrin amino acid sequence set forth in SEQ ID NO:8 or position 93 of the α2 integrin I domain amino acid sequence set forth in SEQ ID NO:11;
(e) an Arg residue corresponding to position 317 of the α2 integrin amino acid sequence set forth in SEQ ID NO:8 or position 165 of the α2 integrin I domain amino acid sequence set forth in SEQ ID NO:11;
(f) an Asn residue corresponding to position 318 of the α2 integrin amino acid sequence set forth in SEQ ID NO:8 or position 166 of the α2 integrin I domain amino acid sequence set forth in SEQ ID NO:11; or
(g) any combination of (a) to (f).

In an embodiment, the above-mentioned humanized anti-α2 integrin antibody is a full length antibody.

In an embodiment, the above-mentioned humanized anti-α2 integrin antibody is an antigen binding fragment.

In an embodiment, the above-mentioned humanized anti-α2 integrin antibody inhibits binding of α2 or α2β1 integrin to an α2β1 integrin ligand.

In an embodiment, the above-mentioned α2β1 integrin ligand is selected from collagen, laminin, Echovirus-1, decorin, E-cadherin, matrix metalloproteinase I (MMP-I), endorepellin, collectin and C1q complement protein.

In embodiments, the above-mentioned method is not associated with (a) platelet activation, (b) platelet aggregation, (c) a decrease in circulating platelet count, (d) bleeding complications, or (e) any combination of (a) to (d).

In an embodiment, the above-mentioned anti-α2 integrin antibody competitively inhibits the binding of an antibody comprising the UL region of SEQ ID NO:19 and the VH region of SEQ ID NO:21 to human α2β1 integrin or the I domain thereof.

Preferred antibodies bind to the I-domain of human α2β1 integrin. In particular, the preferred antibodies are able to block α2-dependent adhesion of cells to the extracellular matrix (ECM), particularly to at least one or both of collagen and laminin. Humanized antibodies are provided, including antibodies based on an antibody referred to herein as TMC-2206. Anti-α2 integrin antibodies are provided that are highly specific for human α2β1 integrin, and whose administration is not associated with undesired effects such as bleeding complications or complications due to cellular activation. The binding specificity (e.g., epitope specificity) of these antibodies is associated with their unexpected non-hemorrhagic profile.

The humanized anti-α2β1 integrin antibody used in the present invention may have a heavy chain variable region comprising the amino acid sequence of HCDR1 (GFSLTNY-GIH; SEQ ID NO:1) and/or HCDR2 (VIWARGFTNYN-SALMS; SEQ ID NO:2) and/or HCDR3 (ANDGVYYAMDY; SEQ ID NO:3). The humanized anti-α2β integrin antibody may have a light chain variable region comprising the amino acid sequence of LCDR1 (SANSSV-NYIH; SEQ ID NO:4 or SAQSSVNYIH; SEQ ID NO:112) and/or LCDR2 (DTSKLAS; SEQ ID NO:5) and/or LCDR3 (QQWTTNPLT; SEQ ID NO:6). In certain embodiments, the humanized anti-α2β1 integrin antibodies have a heavy chain comprising HCDR1 (GFSLTNYGIH; SEQ ID NO:1) and/or HCDR2 (VIWARGFTNYNSALMS; SEQ ID NO:2) and/or HCDR3 (ANDGVYYAMDY; SEQ ID NO:3) and a light chain variable region comprising the amino acid sequence of LCDR1 (SANSSVNYIH; SEQ ID NO:4 or SAQSSVNYIH; SEQ ID NO:112) and/or LCDR2 (DTSKLAS; SEQ ID NO:5) and/or LCDR3 (QQWTTNPLT; SEQ ID NO:6). In other embodiments, the antibody comprises an amino acid sequence variant of one or more of such CDRs, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants).

DETAILED DESCRIPTION OF THE INVENTION

The present invention provides methods of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma using antibodies specifically reactive with human alpha 2 (α2) integrin, including humanized antibodies. The humanized antibodies may have human framework regions (FWs) and complementarity determining regions (CDRs) from a non-human antibody, typically a mouse, specifically reactive with human α2 integrin. In preferred embodiments, one or more of the CDR regions are derived from or based on the murine antibody secreted by the BHA2.1 hybridoma (Hangan et al., Cancer Res., 56(13): 3142-9 (1996)). This antibody binds to human and rat α2β1 integrin, but does not bind the murine counterpart. The antibody so produced by the BHA2.1 hybridoma is referred to herein as TMC-2206 and is commercially available from Chemicon (now part of Millipore, catalog number MAB1998). Further provided are methods of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma using antibodies having similar binding properties and antibodies (or other antagonists) having similar functionality as the antibodies disclosed herein. Preferred anti-α2 integrin antibodies include those that (a) bind to the I domain of α2 integrin, (b) inhibit the function of α2 integrin (e.g., collagen or laminin binding), (c) bind to α2 integrin on resting platelets without inducing platelet activation and (d) recognize the binding epitope of TMC-2206 (e.g., compete with TMC-2206 for the binding to α2 integrin). Such antibodies may bind preferentially to the inactive or closed conformation of the target α2 integrin molecule without competing for the ligand binding site. Advantages of anti-α2 integrin antibodies as described herein that bind preferentially to the closed conformation of the α2β1 integrin and/or bind to α2β1 integrin without competing for the ligand binding site (e.g., are not a ligand mimetic) include preventing potential platelet activation, platelet aggregation, decreases in circulating platelet count and/or bleeding complications in a treated subject.

"Bleeding complications" as used herein refers to any adverse effect on blood levels and physiology, including platelet thrombotic responses, thrombocytopenia, increased time to clot, increased bleeding time and blood loss that limit therapeutic use of the anti-α2 integrin antibody.

α2β1 integrin is a molecule comprised of an α2 integrin subunit (see, e.g., SEQ ID NO:7, for DNA sequence and SEQ ID NO:8 for protein sequence of human α2) from the family of alpha integrins, and a β1 integrin subunit (see, e.g., SEQ ID NO:9 for DNA sequence and SEQ ID NO:10 protein sequence of human β1) from the family of beta integrins, and may be from any subject including a mammal, but preferably is from a human. The α2β1 integrin may be purified from any natural source, or may be produced synthetically (e.g., by use of recombinant DNA technology). The nucleic acid coding sequences for α2 integrin and for β1 integrin are described in Takada and Hemler J. Cell Biol. 109(1):397-407 (1989; GenBank submission X17033; subsequently updated to entry NM 002203) and Argraves, W. S, J. Cell. Biol. Sep. 105(3):1183-90 (1987; Genbank submission X07979.1 and related sequences representing alternatively spliced variants), respectively.

The 'I' domain of the α2β1 integrin molecule refers to a region of this α2β1 integrin molecule within the α2 subunit, and is described, for example, in Kamata et al., J. Biol. Chem. 269:9659-9663 (1994); Emsley et al., J. Biol. Chem. 272: 28512 (1997) and Cell 101:47 (2000). The amino acid sequence of a human I domain of α2 integrin is shown as SEQ ID NO:11 (see also, e.g., SEQ ID NO: 107). The I domain of α2 integrin contains a MIDAS type of ligand binding site (Metal Ion Dependent Adhesion Site) which has a requirement and a specificity for a given divalent cation to support ligand binding. The amino acid sequences for an I domain of α2 integrin in rat is shown as SEQ ID NO:93 (see also, e.g., SEQ ID NO:113) and in mouse is shown as SEQ ID NO:94 (see also, e.g., SEQ ID NO:114). Cynomolgus monkey and rhesus monkey I domain sequences were cloned from the leukocyte fraction derived from whole blood and are provided in SEQ ID NO:103 (DNA), SEQ ID NO:171 (amino acid) for cynomolgus and SEQ ID NO:104 (DNA), SEQ ID NO:172 (amino acid) for rhesus, respectively.

A TMC-2206 (BHA2.1) epitope refers to a region of the I domain of human α2 integrin to which the TMC-2206 antibody binds. This epitope spans a region of 127 amino acids encompassing amino acid residues, K40, N73, Q89, Y93, R165, and N166, which contribute to binding and optionally, other amino acid residues of the α2 integrin I domain as described in WO2007/056858.

The term "cancer" refers to or describes the physiological condition in mammals that is typically characterized by unregulated cell growth. Included in this definition are benign and malignant cancers, metastatic cancers as well as adenomas or adenocarcinomas. "Tumor" refers to all neoplastic cell growth and proliferation, whether malignant or benign, and all pre-cancerous and cancerous cells and tissues. "Benign tumor" or "benign cancer" refers to a tumor that remains localized at the site of origin and does not have the capacity to infiltrate, invade, or metastasize to a distant site. "Malignant tumor" refers to a tumor that invades and damages other tissues around them. Treatment of cancer refers to both therapeutic use and prophylactic or preventative use of the anti-α2 integrin antibodies described herein. Those in need of treatment include those already diagnosed with the cancer as well as those in which the onset of the disorder is to be prevented or delayed.

Cancers can be selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, and multiple myeloma. Cancers which are preferably treated using the anti-α2 integrin antibodies described herein are selected from the group consisting of breast cancer, colorectal cancer, rectal cancer, non-small cell lung cancer, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amendable for treatment of the invention include metastatic cancers. Thus even more preferred are cancers selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, multiple myeloma, metastatic colorectal and metastatic breast cancer. Particular preferred are cancers selected from the group consisting of non-small cell lung cancer, pancreatic cancer, glioblastoma, cervical cancer, ovarian cancer, liver cancer, breast cancer, colon cancer, colorectal cancer, kidney cancer, prostate cancer, mesothelioma, fibrosarcoma, osteosarcoma, epidermoid carcinoma, metastatic colorectal, metastatic prostate and metastatic breast cancer. More particular preferred are cancers selected from the group consisting of non-small cell lung cancer, pancreatic cancer, glioblastoma, liver cancer, breast cancer, colon cancer, colorectal cancer, kidney cancer, prostate cancer, mesothelioma, fibrosarcoma, metastatic colorectal, metastatic prostate and metastatic breast cancer. Even more particular preferred are cancers selected from the group consisting of pancreatic cancer, breast cancer, colon cancer, colorectal cancer, non-small cell lung cancer, fibrosarcoma, metastatic colorectal, and metastatic breast cancer. Most particular preferred are cancers selected from the group consisting of pancreatic cancer, breast cancer, colon cancer, colorectal cancer, non-small cell lung cancer, and fibrosarcoma. Most preferred are pancreatic cancer, breast cancer or metastatic breast cancer, with a particular preference to pancreatic cancer. "Breast cancer" as referred herein include mammary adenocarcinoma. The method of the present invention is particularly suitable for the treatment of vascularized tumors.

A subject, including for purposes of treatment, refers to any animal classified as a mammal, including humans, domestic and farm animals, and zoo, sports or pet animals such as dogs, horses, cats, cows etc. Preferably, the subject is a human.

The term antibody or immunoglobulin is used in the broadest sense, and covers monoclonal antibodies (including full length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')$_2$, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, VH regions ($V_H$, $V_H$-$V_H$), anticalins, PepBodies™, antibody-T-cell epitope fusions (Troybodies) or Peptibodies. "Antibody fragment" and "antigen binding fragment" have the same meaning and are equivalently used herein.

A monoclonal antibody refers to an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (e.g., polyclonal) antibody preparations which typically include different antibodies directed against different determinants (e.g., epitopes) on an antigen, each monoclonal antibody is directed against at least a single determinant on the antigen. The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature 256:495 (1975), or may be made by recombinant DNA methods (see, e.g., U.S. Pat. No. 4,816,567). Monoclonal antibodies may also be isolated from phage antibody libraries, for example, using the techniques described in Clackson et al., Nature 352:624-628 (1991) and Marks et al., J. Mol. Biol. 222:581-597 (1991). Monoclonal antibodies can also be isolated using the techniques described in U.S. Pat. Nos. 6,025,155 and 6,077,677 as well as U.S. Patent Application Publication Nos. 2002/0160970 and 2003/0083293 (see also, e.g., Lindenbaum, et al., Nucleic Acids Research 32 (21):0177 (2004)).

Monoclonal antibodies can include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81: 6851-6855 (1984) for mouse-human chimeric antibodies).

A hypervariable region refers to the amino acid residues of an antibody which are responsible for antigen-binding. The hypervariable region comprises amino acid residues from a complementarity determining region or CDR (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987)). Framework or FR residues are those variable domain residues other than the hypervariable region residues. For antibodies described herein, the CDR and framework regions are identified based on the Kabat numbering system except that the CDR1 of the heavy chain is defined by Oxford Molecular's AbM definition as spanning residues 26 to 35. The Oxford Molecular's AbM antibody modeling software (Martin et al., Proc. Natl. Acad. Sci. USA, 86, 9268-9272 (1989); Martin et al., Methods Enzymol., 203, 121-153 (1991); Pedersen et al., Immunomethods, 1, 126 (1992); and Rees et al., In Sternberg M. J. E. (ed.), Protein Structure Prediction. Oxford University Press, Oxford, 141-172. (1996)) combines the Kabat CDR and the Chothia hypervariable region numbering systems to define CDRs.

Humanized forms of non-human (e.g., murine) antibodies may be chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In addition, individual or groups of Fv framework region (FR) residues of the human immunoglobulin may be replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable regions or domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (e.g., Fc), typically that of a human immunoglobulin (see, e.g., Queen et al., Proc. Natl. Acad. Sci. USA 86:10029 (1989), and Foote and Winter, J. Mol. Biol. 224: 487 (1992)).

Single-chain Fv or scFv antibody fragments may comprise the $V_H$ and $V_L$ regions or domains of antibody, wherein these domains are present in a single polypeptide chain. Generally, the Fv polypeptide further comprises a polypeptide linker between the $V_H$ and $V_L$ domains which enables the scFv to form the desired structure for antigen binding (for a review, see, e.g., Pluckthun in The Pharmacology of Monoclonal Antibodies, vol. 113, Rosenburg and Moore eds. Springer-Verlag, New York, pp. 269-315 (1994)).

Diabody refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA 90: 6444-6448 (1993).

Linear antibody refers to antibodies such as those described in Zapata et al., Protein Eng. 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

An isolated antibody refers to one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An epitope tagged antibody refers to one wherein the antibody of the invention is fused to an epitope tag. The epitope tag polypeptide has enough residues to provide an epitope against which an antibody thereagainst can be made, yet is short enough such that it does not interfere with activity of the anti-α2β1 integrin antibody. The epitope tag preferably is sufficiently unique so that the antibody thereagainst does not substantially cross-react with other epitopes. Suitable tag polypeptides generally have at least 6 amino acid residues and usually between about 8-50 amino acid residues (preferably between about 9-30 residues). Examples include the flu HA tag polypeptide and its antibody 12CA5 (Field et al., Mol. Cell. Biol. 8: 2159-2165 (1988)); the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6): 547-553 (1990)). In certain embodiments, the epitope tag is a salvage receptor binding epitope which is an epitope of the Fc region of an IgG molecule (e.g., $IgG_1$, $IgG_2$, $IgG_3$, or $IgG_4$) that is responsible for increasing the in vivo serum half-life of the IgG molecule.

A cytotoxic agent refers to a substance that inhibits or prevents the function of cells and/or causes destruction of cells. This can include radioactive isotopes (e.g., $^{131}I$ $^{125}I$, $^{90}Y$ and $^{186}Re$), chemotherapeutic agents, and toxins such as enzymatically active toxins of bacterial, fungal, plant or animal origin, or fragments thereof. A non-cytotoxic agent refers to a substance that does not inhibit or prevent function of cells and/or does not cause destruction of cells. A non-cytotoxic agent may include an agent that can be activated to become cytotoxic. A non-cytotoxic agent may include a bead, liposome, matrix or particle (see, e.g., U.S. Patent Publications 2003/0028071 and 2003/0032995 which are incorporated by reference herein). Such agents may be conjugated, coupled, linked or associated with an anti-α2β1 integrin antibody as described herein.

A chemotherapeutic agent refers to a chemical compound useful in the treatment of cancer. Examples of chemotherapeutic agents include but are not limited to Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see U.S. Pat. No. 4,675,187), Melphalan and other related nitrogen mustards.

A prodrug refers to a precursor or derivative form of a pharmaceutically active substance that is less cytotoxic to tumor cells compared to the parent drug and is capable of being enzymatically activated or converted into the more active parent form (see, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are mot limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form can be those chemotherapeutic agents described above.

A label refers to a detectable compound or composition which is conjugated or coupled directly or indirectly to the antibody. The label may itself be detectable by itself (e.g., radioisotope labels or fluorescent labels) or, in the case of an enzymatic label, may catalyze chemical alteration of a substrate compound or composition which is detectable.

Solid phase refers to a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

The terms "once every two weeks dosis regimen", "once every two weeks dosing", and "once every two weeks administration", as used herein, refer to the time course of administering a substance (e.g., anti-α2 integrin antibody) to a subject to achieve a therapeutic objective (e.g., the treatment of a cancer). The once every two weeks dosing regimen is not intended to include a weekly dosing regimen. Preferably, the substance is administered every 9-19 days, more preferably, every 11-17 days, even more preferably, every 13-15 days, and most preferably, every 14 days.

A liposome refers to a small vesicle composed of various types of lipids, phospholipids and/or surfactant which is useful for delivery of a drug (such as the antibodies of the invention and, optionally, a chemotherapeutic agent) to a mammal. The components of the liposome are commonly arranged in a bilayer formation, similar to the lipid arrangement of biological membranes.

An isolated nucleic acid molecule refers to a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

A viral vector refers to a vehicle for the transfer of a nucleic acid (e.g. DNA or RNA) to cells through viral infection or transduction. Examples of viral vectors include retroviruses, adenoviruses, pox viruses, and baculovirus.

A non-viral vector refers to a nucleic acid vehicle such as a CAN, plasmid or chromosome that is delivered to cells by non-viral methods such as electroporation, injections, and cationic reagent mediated transfection.

Expression control sequences refer to those DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked DNA sequences are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Cell, cell line, and cell culture are often used interchangeably and all such designations include progeny. Transformants and transformed cells (e.g., obtained by transfection, transformation or transduction of nucleic acids, vectors, virus, etc.) include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Humanized antibodies as described herein include antibodies that have variable region frameworks derived from a human acceptor antibody molecule, hypervariable or CDR sequences from a donor murine antibody, and constant regions, if present, derived from human sequences.

Humanized antibodies used in the present invention have been constructed comprising CDRs from both the heavy chain variable and light chain variable regions of the murine monoclonal antibody clone BHA2.1 (Hangan et al., Cancer Res. 56:3142-3149 (1996)). Preferred starting materials for constructing antibodies are anti-α2 integrin antibodies such as those secreted by the BHA2.1 hybridoma (e.g., TMC-2206) that are function-blocking antibodies directed against human α2 integrin and are dependent for binding and activity on the presence of an intact I-domain within the targeted α2 integrin. Preferred are humanized antibodies with the epitope specificity of TMC-2206 (or BHA2.1), including antibodies which bind to the inactive conformation of the α2 integrin molecule, and/or do not act as ligand mimetics. Preferred are humanized antibodies with the epitope specificity of TMC-2206 (or BHA2.1) that, although they interact with α2β1 integrin present on both leukocytes and platelets, do not cause platelet activation, impair aggregation of activated platelets on collagen, have minimal or no effect on bleeding and/or are not associated with bleeding complications at administered concentrations, including therapeutic doses in vivo.

Antibodies may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential antigenicity. Germline databases are made up of antibody sequences that read through the end of the heavy chain FW3 region and partially into the CDR3 sequence. For selection of a FW4 region, it is preferred to search databases of mature antibody sequences which have been derived from the selected germline molecule, and also preferred to select a reasonably homologous FW4 region for use in the recombinant antibody molecule. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well. For humanized anti-α2 integrin antibodies with the same or similar epitope specificity and/or functional properties as TMC-2206, a preferred light chain human acceptor molecule is SEQ ID NO:37 with the germline antibody sequence A14 for the FW 1-3 region and the sequence FGQGTKVEIK for FW4 (SEQ ID NO:38) which represents a common FW-4 of mature kappa 1 light chains (e.g., light chain sequence AAB24132 (NCBI entry gi/259596/gb/AAB24132).

Antibodies may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential antigenicity. Germline databases are made up of antibody sequences that read through the end of the heavy chain FW3 region and partially into the CDR3 sequence. For selection of a FW4 region, it is preferred to search databases of mature antibody sequences which have been derived from the selected germline molecule, and also preferred to select a reasonably homologous FW4 region for use in the recombinant antibody molecule. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region include homology in CDR length between the murine donor molecule and the human acceptor molecule. Human acceptor antibody molecules are preferably selected by homology search to the V-BASE database, although other databases such as the Kabat and the public NCBI databases may be used as well. For anti-α2 integrin antibodies with the same or similar epitope specificity and/or functional properties as TMC-2206, a preferred heavy chain acceptor molecule is SEQ ID NO:39 with the germline antibody sequence 4-59 for the FW 1-3 region (SEQ ID NO:12) and antibody, CAA48104.1 (NCBI entry, gi/33583/emb/CAA48104.1) a mature antibody derived from the 4-59 germline sequence for the FW 4 region (SEQ ID NO:13).

Methods for humanizing a nonhuman α2 integrin antibody are known to the skilled person and are described e.g. in WO2007/056858. In order to humanize an anti-α2 integrin antibody, the nonhuman antibody starting material is obtained, including by preparation from immunization or by purchase of commercially available antibodies. Exemplary techniques for generating antibodies used in the present invention are described in WO2007/056858.

The α2β1 integrin antigen to be used for production of antibodies may be, for example, a soluble form of α2β1 integrin or other fragment of α2β1 integrin (e.g., an α2β1 integrin fragment comprising a human α2 integrin I-domain (SEQ ID NO:11); see also, e.g., SEQ ID NO: 107). Other forms of α2 integrin useful for generating antibodies will be apparent to those skilled in the art based on the sequence of α2 integrin (e.g., a human α2 integrin as in SEQ ID NO:8).

Polyclonal antibodies are preferably raised in animals by multiple subcutaneous (sc), intravenous (iv) or intraperitoneal (ip) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen, immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293 (see also, e.g., Lindenbaum, et al., Nucleic Acids Research 32 (21):0177 (2004)).

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell (see, e.g., Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (e.g., Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can be determined, for example, by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures including, for example, protein A chromatography, hydrophobic interaction chromatography, hydroxylapatite chromatography, gel electrophoresis, dialysis, and/or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells, including those that do not otherwise produce immunoglobulin protein, to obtain the synthesis of monoclonal antibodies in the recombinant host cells. Recombinant production of antibodies is described in further detail below.

In certain embodiments, it may be desirable to generate amino acid sequence variants of the humanized antibody, particularly where these improve the binding affinity or other biological properties of the humanized antibody.

Amino acid sequence variants of humanized anti-α2β1 integrin antibody are prepared by introducing appropriate nucleotide changes into a humanized anti-α231 integrin antibody DNA, or by peptide synthesis. Such variants include, for example, deletions from, and/or insertions into and/or substitutions of, residues within the amino acid sequences shown for the anti-α2 integrin antibody TMC-2206 (e.g., derived from or based on variable region sequences as shown in SEQ ID NOS: 19 and 21). Any combination of amino acid deletion, insertion, and substitution is made to arrive at the final construct, provided that the final construct possesses the desired characteristics. The amino acid changes also may alter post-translational processes of the humanized anti-α2 integrin antibody, such as changing the number or position of glycosylation sites.

There are a number of methods used to make antibodies human or human-like (e.g., "humanization"). Approaches to humanize antibodies have varied over the years. One approach was to generate murine variable regions fused to human constant regions, so-called murine-human Fc chimeras (see, e.g., Morrison et al., Proc. Natl. Acad. Sci. USA 81:6851-6855 (1984); U.S. Pat. No. 5,807,715). Another approach exploited the fact that CDRs could be readily identified based on their hypervariable nature (Kabat et al, J. Biol. Chem. 252:6609-6616 (1977)), Kabat, Adv. Protein Chem. 32:1-75 (1978)) and canonical structure (Chothia and Lesk, J. Mol. Biol. 196(4):901-17 (1987); Lazakani et al., J. Mol. Biol. 272:929 (1997) and humanized by grafting just the non-human CDR regions (referred to as donor CDRs) onto a human framework (referred to as acceptor frameworks) as shown, for example by Jones et al., Nature 321(6069):522-5 (1986); (see, e.g., U.S. Pat. No. 5,225,539; U.S. Pat. No. 6,548,640). The six CDR loops are presented in a cluster, and based on crystallographic analysis, critical framework residues within the so-called "Vernier" zone flanking the CDRs or in the heavy-light chain interface can be readily identified (see, e.g., Chothia and Lesk, J. Mol. Biol. 196(4):901-17 (1987); Chothia et al., J. Mol. Biol. 186(3):651-63 (1985); Chothia et al., Nature 342(6252):877-83 (1989)). These residues can be back-mutated to the murine residue to restore the correct relative orientation of the six CDRs (see, e.g., Verhoyen et al., Science 239(4847):1534-6 (1988); Reichman et al., Nature 332(6162):323-7 (1988); Tempest et al., Biotechnology (NY) 9(3):266-71 (1991)). Since variable regions can be classified in families that bear relatively high homology between mouse and human (reviewed in e.g., Pascual and Capra Adv. Immunol. 49:1-74 (1991)), these early studies also indicated that the potential for loss in affinity could be minimized in the grafted antibody by selecting the human germline sequence with the highest homology to the murine antibody of interest for use as the human acceptor molecule (see, e.g., U.S. Pat. No. 5,225,539; Verhoyen et al., Science 239(4847):1534-6 (1988)).

Family homologies and structural relationships between frameworks that impact correct presentation of a given type of CDR canonical structure have been reported (see, e.g., Al-Lazakani et al., J. Mol. Biol. 273(4):927-48 (1997) and references therein). Preferably, a best fit human or germline sequence is chosen. Available databases of antibody germline sequences may be used to determine the family subtype of a given murine heavy and light chain and to identify best fit sequences useful as human acceptor frameworks within that human subfamily. Both the linear amino acid homology of the donor and acceptor frameworks as well as the CDR canonical structure are preferably taken into account.

Exemplary heavy chain residues which may be substituted in a humanized anti-α2 integrin antibody include any one or more of the following framework residue numbers: H37, H48, H67, H71, H73, H78 and H91 (Kabat numbering system). Preferably at least four of these framework residues are substituted. A particularly preferable set of substitutions for the heavy chain in humanized anti-α2 integrin antibodies as exemplified herein is H37, H71, H73 and H78. Similarly, residues in the light chain can also be substituted. Exemplary light chain residues for substitution include any one or more of the following residue numbers: L1, L2, L4, L6, L46, L47, L49 and L71. Preferably at least three of these framework residues are substituted. A particularly preferable set of substitutions for the light chain in humanized anti-α2 integrin antibodies as exemplified herein is L2, L46 and L49.

A useful method for identification of certain residues or regions of a humanized anti-α2 integrin antibody that are preferred locations for mutagenesis is called "alanine scanning mutagenesis" (see, e.g., Cunningham and Wells Science, 244: 1081-1085 (1989)). Here, a residue or group of target residues are identified (e.g., charged residues such as arg, asp, his, lys, and glu) and replaced by a neutral or negatively charged amino acid (preferably alanine or polyalanine) to affect the interaction of the amino acids with α2β1 integrin antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed humanized anti-α2 integrin antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a humanized anti-α2 integrin antibody with an N-terminal methionyl residue or the antibody fused to an epitope tag. Other insertional variants of a humanized anti-α2 integrin antibody molecule include the fusion to the N- or C-terminus of a humanized anti-α2 integrin antibody of an enzyme or a polypeptide which increases the serum half-life of the antibody (see below).

Another type of variant is an amino acid substitution variant. These variants have at least one amino acid residue in a humanized anti-α2 integrin antibody molecule removed and a different residue inserted in its place. The sites of greatest interest for substitutional mutagenesis include the hypervariable loops, but framework alterations are also contemplated. Hypervariable region residues or framework residues involved in antigen binding are generally substituted in a relatively conservative manner. Such conservative substitutions are shown below under the heading of "preferred substitutions". If such substitutions result in a change in biological activity, then more substantial changes, denominated "exemplary substitutions" or as further described below in reference to amino acid classes, are introduced and the products screened.

| Original Residue | Exemplary Substitutions | Preferred Substitutions |
| --- | --- | --- |
| Ala (A) | val; leu; ile | Val |
| Arg (R) | lys; gln; asn | Lys |
| Asn (N) | gln; his; lys; arg | Gln |
| Asp (D) | glu | Glu |
| Cys (C) | ser | Ser |
| Gln (Q) | asn | Asn |
| Glu (E) | asp | Asp |
| Gly (G) | pro; ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |

| Original Residue | Exemplary Substitutions | Preferred Substitutions |
|---|---|---|
| Lys (K) | arg; gln; asn | Arg |
| Met (M) | leu; phe; ile | leu |
| Phe (F) | leu; val; ile; ala; tyr | Leu |
| Pro (P) | ala | Ala |
| Ser (S) | thr | Thr |
| Thr (T) | ser | Ser |
| Trp (W) | tyr; phe | Tyr |
| Tyr (Y) | trp; phe; thr; ser | Phe |
| Val (V) | ile; leu; met; phe; ala; norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper confirmation of a humanized anti-α2 integrin antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that it contains or lacks one or more of the above-described tripeptide sequences (for N-linked glycosylation sites). The alteration may also be made by the addition of, substitution by, or deletion of, one or more serine or threonine residues to the sequence of the original antibody (for O-linked glycosylation sites). Nucleic acid molecules encoding amino acid sequence variants of humanized anti-α2 integrin antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, or cassette mutagenesis of an earlier prepared variant or a non-variant version of humanized anti-α2 integrin antibody.

Ordinarily, amino acid sequence variants of a humanized anti-α2 integrin antibody will have an amino acid sequence having at least 75% amino acid sequence identity with the original humanized antibody amino acid sequences of either the heavy or the light chain (e.g., variable region sequences as in SEQ ID NO:21 or SEQ ID NO:19, respectively), more preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the humanized anti-α2 integrin residues, after aligning the sequences and introducing gaps, if necessary, to achieve the maximum percent sequence identity, and not considering any conservative substitutions (as described above) as part of the sequence identity. None of N-terminal, C-terminal, or internal extensions, deletions, or insertions into the antibody sequence shall be construed as affecting sequence identity or homology. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3 (1978)) can be used in conjunction with the computer program. For example, the percent identity can the be calculated as: the total number of identical matches multiplied by 100 and then divided by the sum of the length of the longer sequence within the matched span and the number of gaps introduced into the longer sequences in order to align the two sequences.

Antibodies having the characteristics identified herein as being desirable in a humanized anti-α2 integrin antibody are screened for by methods as described herein. For example, methods for screening candidate anti-α2 integrin antibodies for preferred characteristics and functionalities are provided that include screening for antibodies which bind to the epitope on α2β1 integrin bound by an antibody of interest (e.g., those which compete with, inhibit or block binding of the TMC-2206 antibody to α2β1 integrin). Cross-blocking assays can be performed and are described, for example, in Antibodies, A Laboratory Manual, Cold Spring Harbor Laboratory, Ed Harlow and David Lane (1988). In addition, or alternatively, epitope mapping, for example, as described in Champe et al., J. Biol. Chem. 270:1388-1394 (1995), can be performed to determine whether the antibody binds an epitope of interest.

Immobilized α2β1 integrin can similarly be used to determine relative binding potencies by measuring $K_i$ values in competition assays. For example, fluorescently labeled Eu-TMC-2206 is used in the presence of varying concentrations of unlabeled candidate antibody, for example, using an assay system similar to that described above. Following a specified incubation time, the amount of bound Eu-TMC-2206 is determined. The inhibition curves are fitted with the "one site competition" model using Prism software (GraphPad, Inc.

CA) to obtain IC$_{50}$ values and to calculate the K$_i$ using the equation of Cheng and Prusoff (Biochem, Pharmacol. 22(23): 3099-108 (1973)).

It is desirable to prepare, identify and/or select humanized anti-α2 integrin antibodies which have beneficial binding properties, for example, under conditions as described in Example 2 of WO2007/056858, wherein candidate antibodies are tested for their ability to block α2β1-integrin mediated cell adhesion in comparison to TMC-2206 and the mouse-human chimeric antibody derived from TMC-2206. For example, CHO cells expressing human α2 integrin and endogenous hamster (31 (Symington et al., J. Cell Biol. 120 (2):523-35 (1993)) are prepared and labeled with CFSE (Molecule Probes, OR).

Labeled cells are prepared and the cell concentration is adjusted; cells are kept in the dark until used. A collagen-coated plate (rat-tail collagen Type I; BD Biosciences) is prepared and each serially diluted antibody solution is added to the collagen plate. Labeled cells are then added to the well and the plate is incubated. After washing, cells are lysed and the fluorescence intensity (excitation, 485 nm; emission, 535 nm) is read. The inhibitory activity of each antibody is calculated.

Additionally, binding constants of the candidate antibodies for the immobilized α2β1 integrin ligand can be calculated as described in Example 2 of WO2007/056858. Wells in a 96 well microtiter plate are coated with platelet α2β1-integrin (custom-coated with human platelet α2β1 by GTI Inc., WI) and then blocked. For example, to determine the affinity of TMC-2206 for its α2 integrin antigen, fluorescently labeled TMC-2206 or isotype control IgG antibody are used. The fluorescently labeled antibody, including Eu-TMC-2206 or Eu-isotype control IgG, is applied to the blocked α2β1-integrin microtiter plates. After incubating the sealed plates to allow the antibody-antigen interaction to reach equilibrium, samples are transferred from each well into a fresh well containing an enhancement solution for the measurement of free (unbound) label. The enhancement solution is also added to the emptied wells for the measurement of bound label. The K$_d$ values of the anti-α2 integrin antibody is calculated by Scatchard analysis. The relative affinity of TMC-2206 derivatives (including humanized antibodies derived from or based on TMC-2206) can be determined by determining the Ki value in a competition assay. For example, for the competition assay, Eu-labelled TMC-2206 is added to α2 (31-coated wells in the presence of unlabelled anti-α2 integrin antibodies, including TMC-2206 or chimeric (including humanized) antibodies derived from or based on TMC-2206, or isotype control IgG antibody at various concentrations. After a period of incubation to reach equilibrium, the wells are washed and the bound labeled antibody levels are measured as retained Eu label in each well. The Ki value can be derived from the EC50 values using the K$_d$ value obtained for the Eu-TMC-2206 antibody by the direct binding studies as described above.

In certain embodiments, the humanized anti-α2 integrin antibody is an antibody fragment. Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science 229: 81 (1985)). However, these fragments can be produced directly by recombinant host cells, such as bacteria (see, e.g., Better et al., Science 240 (4855)1041-1043 (1988); U.S. Pat. No. 6,204,023. For example, Fab'-SH fragments can be directly recovered from E. coli and chemically coupled to form F(ab')$_2$ fragments (Carter et al., Bio/Technology 10: 163-167 (1992)). According to another approach, F(ab')$_2$ fragments can be isolated directly from recombinant host cell culture. Other techniques for the production of antibody fragments will be apparent to the skilled practitioner.

In some embodiments, it may be desirable to generate multispecific (e.g., bispecific) humanized anti-α2 integrin antibodies having binding specificities for at least two different epitopes. Exemplary bispecific antibodies (e.g., with two different binding arms) may bind to two different epitopes of the α2β1 integrin protein. Alternately, an anti-α2 integrin arm may be combined with an arm which binds to a triggering molecule on a leukocyte such as a T-cell receptor molecule (e.g., CD2 or CD3), or Fc receptors for IgG (FcγR), such as FcγR1 (CD64), FcγRII (CD32) and FcγRIII (CD16) so as to focus cellular defense mechanisms on a cell which has α2β1 integrin bound to its surface. Bispecific antibodies can be used to localized cytotoxic agents to cells with α2β1 integrin bound to their surface. These antibodies possess a α2β1 integrin binding arm and an arm which binds the cytotoxic agent (e.g., gelonin, saporin, anti-interferon alpha, vinca alkaloid, ricin A chain, or radioisotope hapten). Bispecific antibodies can be prepared as full length antibodies or antibody fragments (e.g., F(ab')$_2$ bispecific antibodies).

According to another approach for making bispecific antibodies, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains are replaced with larger side chains (e.g., tyrosine or tryptophan). Compensatory cavities of identical or smaller size to the large side chain(s) are created on the interface of the second antibody by replacing large amino acid side chains with smaller ones (e.g., alanine or threonine). This provides a mechanism for increasing the yield of the heterodimers over other unwanted end-products such as homodimers (see, e.g., WO96/27011).

Bispecific antibodies include cross-linked or heteroconjugate antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed, for example, in U.S. Pat. No. 4,676,980 along with a number of cross-linking techniques.

Techniques for generating bispecific antibodies from antibody fragments have also been described in the literature. Bispecific antibodies can be prepared using chemical linkage. For example, Brennan et al., (Science 229:81 (1985)) describe a procedure wherein intact antibodies are proteolytically cleaved to generate F(ab')$_2$ fragments. These fragments are reduced in the presence of the dithiol complexing agent sodium arsenite to stabilize vincal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments, recovered from E. coli, can be chemically coupled to form bispecific antibodies. For example, Shalaby et al., (J. Exp. Med. 175:217-225 (1992)) describe the production of a fully humanized bispecific antibody F(ab')$_2$ molecule. Where each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers (see, e.g., Kostgelny et al., J. Immunol. 148(5):1547-1553 (1992)). The leucine zipper peptides from the Fos and Jun proteins were linked to Fab' portions of two different antibodies by gene fusion. The antibody homodimers were reduced at the hinge region to form monomers and then re-oxidized to form antibody heterodimers. This method can also be utilized for the production of antibody heterodimers. The diabody technology (see, e.g., Hollinger et al., Proc. Natl. Acad. Sci. USA 90:6444-6448 (1993) has provided an alternative mechanism for making bispecific antibody fragments. The fragments comprise a heavy chain variable region (VH) connected to a light-chain variable region (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv or scFv) dimers also has been reported (see, e.g., Gruber et al., J. Immunol. 152:5368 (1994)). Alternatively, the bispecific antibody, may be a linear antibody, for example, produced as described in Zapata et al., Protein Eng. 8(10):1057-1062 (1995).

Antibodies with more than two valencies are contemplated. For example, trispecific antibodies can be prepared (see, e.g., Tutt et al., J. Immunol. 147:60 (1991)).

Other modifications of the humanized anti-α2 integrin antibodies are contemplated. For example, it may be desirable to modify the antibody with respect to effector function, so as to enhance or decrease the effectiveness of the antibody, for example, in treating cancer. Cysteine residue(s) may be introduced in the Fc region, thereby allowing interchain disulfide bond formation in the region. The homodimeric antibody thus generated may have improved internalization capability and/or increased complement mediated cell killing (CMC) and/or antibody-dependent cellular cytotoxicity (ADCC) (see e.g., Caron et al., J. Exp. Med. 176:1191-1195 (1992) and Shopes, B. J. Immunol. 148:2918-2922 (1992)). Homodimeric antibodies with enhanced anti-tumor activity may also be prepared using heterobifunctional cross-linkers (see, e.g., those described in Wolff et al., Cancer Research 53:2560-2565 (1993)). Alternatively, an antibody can be engineered which has dual Fc regions and may thereby have enhanced CMC and/or ADCC capabilities (see, e.g., Stevenson et al., Anti-Cancer Drug Design 3:219-230 (1989)).

Immunoconjugates comprising a humanized anti-α2 integrin antibody conjugated to a moiety, e.g., a molecule, composition, complex, or agent, for example a cytotoxic agent such as a chemotherapeutic agent, toxin (e.g., an enzymatically active toxin of bacterial, fungal, plant or animal origin, or fragments thereof), or a radioactive isotope (e.g., a radioconjugate), for the targeting of the agent to an anti-α2 integrin-expressing cell, tissue or organ. Such an immunoconjugate may be used in a method of targeting the moiety or agent to a particular site of action characterized by the presence of α2 or α2β1 integrin.

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin or the tricothecenes. A variety of radionuclides are available for the production of radioconjugated anti-alpha 2 integrin antibodies. Examples include $^{212}$Bi, $^{131}$In, $^{90}$Y or $^{186}$Re.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as gluteraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), or bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody (see, e.g., WO94/11026).

In another embodiment, the antibody may be conjugated to a receptor (such as streptavidin) for utilization in pretargeting α2 integrin-expressing cell, tissue or organ wherein the antibody-receptor conjugate is administered to the patient, followed by removal of unbound conjugate from the circulation using a clearing agent and then administration of a ligand (e.g., avidin) which is conjugated to an agent, for example a cytotoxic agent (e.g., a radio-nuclide).

The anti-α2 integrin antibodies disclosed herein may also be formulated as immunoliposomes. Liposomes containing the antibody are prepared by methods known in the art, such as described in Epstein et al., Proc. Natl. Acad. Sci. USA 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an anti-α2 integrin antibody can be conjugated to the liposomes as described in Martin et al., J. Biol. Chem. 257: 286-288 (1982) via a disulfide interchange reaction. A chemotherapeutic agent (e.g., doxorubicin) is optionally contained within the liposome (see, e.g., Gabizon et al., J. National Cancer Inst. 81(19): 1484 (1989)).

Humanized anti-α2 integrin antibodies may also be used in Antibody Directed Enzyme Prodrug Therapy (ADEPT) by conjugating the antibody to a prodrug-activating enzyme which converts a prodrug (e.g., a peptidyl chemotherapeutic agent, see, e.g., WO81/01145) to an active drug. (see, e.g., WO88/07378 and U.S. Pat. No. 4,975,278). The enzyme component of the immunoconjugate useful for ADEPT includes any enzyme capable of acting on a prodrug in such a way so as to covert it into its more active form. Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known as abzymes, can be used to convert the prodrugs of the invention into free active drugs (see, e.g., Massey, Nature 328: 457-458 (1987)). Antibody-abzyme conjugates can be prepared as described herein, including for delivery of the abzyme to a α2 integrin-expressing cell, tissue or organ.

Enzymes may be covalently bound to the anti-α2 integrin antibodies by techniques well known in the art, including the use of the heterobifunctional crosslinking reagents discussed above. Alternatively, fusion proteins comprising at least the antigen binding region of an anti-α2 integrin antibody linked to at least a functionally active portion of an enzyme can be constructed using recombinant DNA techniques well known in the art (see, e.g., Neuberger et al., Nature 312: 604-608 (1984)).

In certain embodiments of the invention, it may be desirable to use an antibody fragment, rather than an intact antibody, for example, to increase tissue or tumor penetration. It may also be desirable to modify the antibody fragment in order to increase its serum half-life. This may be achieved by incorporation of a salvage receptor binding epitope into the antibody fragment, for example, by mutation of the appropriate region in the antibody fragment or by incorporating the epitope into a peptide tag that is then fused to the antibody fragment at either end or in the middle, for example, by DNA or peptide synthesis (see, e.g., WO96/32478).

Covalent modifications of the humanized anti-α2 integrin antibodies may be made, for example, by chemical synthesis or by enzymatic or chemical cleavage of the antibody. Other types of covalent modifications of the antibody are introduced into the molecule by reacting targeted amino acid residues of the antibody with an organic derivatizing agent that is capable of reacting with selected side chains or the N- or C-terminal residues. Cysteinyl residues, for example, most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues, for example, are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues, for example, are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate. Arginyl residues, for example, are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group. Tyrosyl residues, for example, are specifically modified with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay. Carboxyl side groups, for example, aspartyl or glutamyl, are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions. Glutaminyl and asparaginyl residues are frequently deamidated to the corresponding glutamyl and aspartyl residues, respectively. These residues are deamidated under neutral or basic conditions. The deamidated form of these residues falls within the scope of this invention. Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine (see, e.g., WO87/05330; Aplin and Wriston, CRC Crit. Rev. Biochem., pp. 259-306 (1981)).

Removal of any carbohydrate moieties present on the antibody may be accomplished, for example, chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact (see, e.g., Hakimuddin, et al., Arch. Biochem. Biophys. 259: 52 (1987); Edge et al., Anal. Biochem., 118: 131 (1981)). Enzymatic cleavage of carbohydrate moieties on antibodies can be achieved by the use of a variety of endo- and exo-glycosidases, (see, e.g., Thotakura et al., Meth. Enzymol. 138: 350 (1987)).

Another type of covalent modification of the antibody comprises linking the antibody to one of a variety of nonproteinaceous polymers, such as polyethylene glycol, polypropylene glycol, or polyoxyalkylenes (see, e.g., U.S. Pat. Nos. 4,640,835; 4,496,689; 4,301,144; 4,670,417; 4,791,192 or 4,179,337).

For recombinant production of the antibody, the nucleic acid(s) encoding the antibody are isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An anti-α2 integrin antibody may be produced recombinantly, including as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a eukaryotic signal sequence (e.g., an immunoglobulin signal sequence), the signal sequence is substituted by a prokaryotic signal sequence including, for example, pectate lysase (such as pelB), alkaline phosphatase, penicillinase, Ipp, or heat-stable enterotoxin II leaders. For yeast secretion, a yeast signal sequence may be utilized, including, for example, the yeast invertase leader, a factor leader (including Saccharomyces and Kluyveromyces α-factor leaders), or acid phosphatase leader, the C. albicans glucoamylase leader, or the signal described in WO90/13646. In mammalian cell expression, mammalian signal sequences as well as viral secretory leaders, for example, the herpes simplex gD signal, are available and may be utilized. The DNA for such a precursor region (e.g., the signal sequence) is ligated in reading frame to DNA encoding an anti-α2 integrin antibody.

Both expression and cloning vectors contain a nucleic acid sequence that enables the vector to replicate in one or more selected host cells. Generally, in cloning vectors, this sequence is one that enables the vector to replicate independently of the host chromosomal DNA, and includes origins of replication or autonomously replicating sequences. Such sequences are well known for a variety of bacteria, yeast, and viruses. For example, the origin of replication from the plasmid pBR322 is suitable for most gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (e.g., the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, (e.g., the gene encoding D-alanine racemase for Bacilli).

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the anti-α2 integrin antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding anti-α2 integrin antibody, wild-type DHFR protein, and another selectable marker such as aminoglycoside 3'-phosphotransferase (APH) can be selected by cell growth in medium containing a selection agent for the selectable marker, including an aminoglycosidic antibiotic, such as kanamycin, neomycin, or G418 (see e.g., U.S. Pat. No. 4,965,199).

One suitable selection gene for use in yeast is the trp1 gene present in the yeast plasmid YRp7 (Stinchcomb et al., Nature, 282: 39 (1979)). The trp1 gene provides a selection marker for a mutant strain of yeast lacking the ability to grow in tryptophan, for example, ATCC No. 44076 or PEP4-1 (see, e.g., Jones, Genetics, 85: 12 (1977)). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6μ circular plasmid pKD1 can be used for transformation of Kluyveromyces yeasts. Alternatively, an expression system for large-scale production of recombinant calf chymosin was reported for K. lactis by Van den Berg, Bio/Technology, 8:135 (1990). Stable multi-copy expression vectors for secretion of mature recombinant human serum albumin by industrial strains of Kluyveromyces have also been disclosed (see, e.g., Fleer et al., Bio/Technology, 9: 968-975 (1991)).

Expression and cloning vectors usually contain a promoter that is recognized by the host organism and is operably linked to the anti-α2 integrin antibody nucleic acid. Promoters suitable for use with prokaryotic hosts include the arabinose promoter (e.g., araB), phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-α2 integrin antibody.

Promoter sequences are known for eukaryotes. Most eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO:115) region where N may be any nucleotide. At the 3' end of most eukaryotic genes is an AATAAA (SEQ ID NO:116) sequence that may be the signal for addition of the poly A tail to the 3' end of the coding sequence. Such sequences are suitably inserted into eukaryotic expression vectors.

Examples of suitable promoter sequences for use with yeast hosts include but are not limited to the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-α2 integrin antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus or Simian Virus 40 (SV40), from heterologous mammalian promoters, for example, the actin promoter or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446, and a modification of this system is described in U.S. Pat. No. 4,601,978 (see, also Reyes et al., Nature 297: 598-601 (1982) on expression of human β-interferon cDNA in mouse cells under the control of a thymidine kinase promoter from herpes simplex virus). Alternatively, the rous sarcoma virus long terminal repeat can be used as the promoter.

Transcription of DNA encoding an anti-α2 integrin antibody by higher eukaryotes is often increased by inserting an enhancer sequence into the vector. Many enhancer sequences are now known from mammalian genes (globin, elastase, albumin, α-fetoprotein, and insulin). Often, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers (see, also, e.g., Yaniv, Nature 297: 17-18 (1982) on enhancing elements for activation of eukaryotic promoters). The enhancer may be spliced into the vector at a position 5' or 3' to the anti-α2 integrin antibody-encoding sequence, but is preferably located at a site 5' from the promoter. Other gene regulation systems well known in the art (e.g. inducible systems, such as tetracycline inducible systems and GeneSwitch™) can be used to control the transcription of DNA encoding an anti-α2 integrin.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an anti-α2 integrin antibody. One useful transcription termination component is the bovine growth hormone polyadenylation region (see, e.g., WO94/11026 and the expression vector disclosed therein).

Suitable host cells for cloning or expressing the DNA in the vectors herein are the prokaryote, yeast, or higher eukaryote cells as described above. Suitable prokaryotes for this purpose include eubacteria, including gram-negative or gram-positive organisms, for example, Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis, Pseudomonas such as P. aeruginosa, and Streptomyces. Suitable E. coli cloning hosts include E. coli 294 (ATCC 31,446), E. coli B, E. coli X1776 (ATCC 31,537), and E. coli W3110 (ATCC 27,325).

In addition to prokaryotes, eukaryotic microbes such as filamentous fungi or yeast are suitable cloning or expression hosts for anti-alpha 2 integrin antibody-encoding vectors. Saccharomyces cerevisiae, or common baker's yeast, is the most commonly used among lower eukaryotic host microorganisms. However, a number of other genera, species, and strains are commonly available and useful, such as Schizosaccharomyces pombe; Kluyveromyces hosts including K. lactis, K. fragilis (ATCC 12,424), K. bulgaricus (ATCC 16,045), K. wickeramii (ATCC 24,178), K. waltii (ATCC 56,500), K. drosophilarum (ATCC 36,906), K. thermotolerans, or K. marxianus; yarrowia (EP 402,226); Pichia pastoris (EP 183, 070); Candida; Trichoderma reesia (EP 244,234); Neurospora crassa; Schwanniomyces such as Schwanniomyces occidentalis; and filamentous fungi including Neurospora, Penicillium, Tolypocladium, or Aspergillus hosts such as A. nidulans or A. niger.

Suitable host cells for the expression of glycosylated anti-α2 integrin antibody are derived from multicellular organisms. Examples of invertebrate cells include plant and insect cells. Numerous baculoviral strains and variants and corresponding permissive insect host cells from hosts such as Spodoptera frugiperda (caterpillar), Aedes aegypti (mosquito), Aedes albopictus (mosquito), Drosophila melanogaster (fruitfly), and Bombyx mori have been identified. A variety of viral strains for transfection are publicly available, for example, the L-1 variant of Autographa californica NPV and the Bm-5 strain of Bombyx mori NPV, and such viruses may be used, particularly for transfection of Spodoptera frugiperda cells.

Plant cell cultures of cotton, corn, potato, soybean, petunia, tomato, and tobacco can also be utilized as hosts.

However, interest has been greatest in vertebrate cells, and propagation of vertebrate cells, including a variety of mammalian cells, has become routine procedure. Examples of useful mammalian host cells include: a monkey kidney CV1 line transformed by SV40 (e.g., COS-7, ATCC CRL 1651); a human embryonic kidney line 293 or 293 cells subcloned for growth in suspension culture (see e.g., Graham et at, J. Gen Virol. 36: 59 (1977)); baby hamster kidney cells (e.g., BHK, ATCC CCL 10); Chinese hamster ovary (CHO) cells, including CHO cells lacking DHFR (see, e.g., DHFR Urlaub et al., Proc. Natl. Acad. Sci. USA 77: 4216 (1980)); mouse sertoli cells ((e.g., TM4, Mather, Biol. Reprod. 23: 243-251 (1980)); monkey kidney cells (e.g., CV1 ATCC CCL 70); African green monkey kidney cells (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); mouse mammary tumor (e.g., MMT 060562, ATCC CCL51); TRI cells (see, e.g., Mather et al., Annals N.Y. Acad. Sci. 383: 44-68 (1982)); MRC 5 cells; FS4 cells; or a human hepatoma line (e.g., Hep G2).

Host cells are transformed with an above-described expression or cloning vectors for anti-α2 integrin antibody production and cultured in conventional nutrient media modified as appropriate for inducing promoters, selecting transformants and/or amplifying the genes encoding the desired sequences.

The host cells used to produce an anti-α2 integrin antibody may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. Culture conditions, such as temperature, pH, and the like, are selected by those skilled in the art, including those culture conditions previously used with the host cell selected for expression.

Anti-α2 integrin antibodies can be purified from cells, including microbial or mammalian cells using, for example, protein A chromatography, ion exchange chromatography, hydrophobic interaction chromatography, gel electrophoresis, dialysis, and/or affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., J. Immunol. Meth. 62:1-13 (1983)). Protein G is useful for mouse isotypes and for human γ3 (see, e.g., Guss et al, EMBO J. 5:1516-1517 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ (J. T. Baker, Phillipsburg, N.J.) is useful for purification. Protein purification can include one or more of the following techniques such as fractionation on an ion-exchange column, ethanol precipitation, Reverse Phase HPLC, chromatography on silica, chromatography on heparin SEPHAROSE™, chromatography on an anion or cation exchange resin (e.g., a polyaspartic acid column), chromatofocusing, SDS-PAGE, ammonium sulfate precipitation and/or hydrophobic interaction chromatography. For example, it may be useful following any purification step(s), to subject a mixture comprising the antibody of interest and contaminants to low pH hydrophobic interaction chromatography using an elution buffer at a pH between about 2.5-4.5, preferably performed at low salt concentrations (e.g., from about 0-0.25M salt).

Formulations of an anti-α2 integrin antibody, including those for therapeutic administration, are prepared for storage by mixing the antibody having the desired degree of purity with optional physiologically acceptable carriers, diluents, excipients or stabilizers (Remington's Pharmaceutical Sciences 16th edition, Osol, A. Ed. (1980)), in the form of lyophilized formulations or aqueous solutions. Acceptable carriers, diluents, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, or other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). For therapeutic uses the anti-α2 integrin antibody of the present invention may be formulated e.g. in phosphate buffered saline (PBS) containing 0.03% Tween-80™. The antibody formulation may also contain more than one active compound for the particular indication being treated, preferably those with complementary activities that do not adversely affect each other. It may be desirable to use anti-α2 integrin antibody in addition to one or more agents currently used to prevent or treat the disorder in question. In addition, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles or nanocapsules) or in macroemulsions. Such techniques are disclosed, for example, in Remington's Pharmaceutical Sciences 16th edition, Osol, A. Ed. (1980).

Formulations to be used for in vivo administration are preferably sterile. This is readily accomplished, for example, by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The anti-α2 integrin antibody is administered by any suitable means, including parenteral, subcutaneous, intraperitoneal, intrapulmonary, or intranasal. If desired for local immunosuppressive treatment, intralesional administration of the antibody (including perfusing or otherwise contacting the graft with the antibody before transplantation) is done. Parenteral administration includes intramuscular, intravenous, intraarterial, intraperitoneal, or subcutaneous administration. In addition, the anti-α2 integrin antibody is suitably administered by pulse infusion, for example, with declining doses of the antibody. Preferably the dosing is given by injections, most preferably intravenous or subcutaneous injections. This may depend in part on whether the administration is brief or chronic. More preferably the anti-α2 integrin antibodies or the compositions as described herein are administered in the methods of the present invention by intravenous infusion, intravenous bolus, subcutaneous administration, subcutaneous infusion or subcutaneous bolus, whereas intravenous infusion or intravenous bolus is most preferred. The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less. The term "intravenous bolus" or "intravenous push" refers to drug administration into a vein of an animal or human such that the body receives the drug in approximately 15 minutes or less, preferably 5 minutes or less. The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue. The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. The term "subcutaneous bolus" refers to drug administration beneath the skin of an animal or human patient, where bolus drug delivery is preferably less than approximately 15 minutes, more preferably less than 5 minutes, and most preferably less than 60 seconds. Administration is preferably within a pocket between the skin and underlying tissue, where the pocket is created, for example,— by pinching or drawing the skin up and away from underlying tissue. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen. Intermittent or periodic dosing is a dosing that is continuous for a certain period of time and is at regular intervals that are preferably separated more than by one day.

"Therapeutically effective amount" or "effective amount" which are used synonymously herein, refer to an amount of the anti-α2 integrin antibodies described herein effective to ameliorate or prevent the symptoms, or prolong the survival of the subject being treated. Determination of a therapeutically effective amount is well within the capabilities of those skilled in the art, especially in light of the detailed disclosure provided herein. The term "therapeutically effective amount" of the anti-α2 integrin antibodies described herein specifically refers to the amount needed to delay or inhibit tumor growth.

For the prevention or treatment of cancer, the appropriate dosage of antibody will depend on the type of disease to be treated, as defined above, the severity and course of the disease, whether the anti-α2 integrin antibody is administered for preventive or therapeutic purposes, previous therapy, the patient's clinical history and response to the antibody, and the discretion of the attending physician. The antibody is suitably administered to the patient at one time or over a series of treatments.

The anti-α2 integrin antibodies can be thus administered to a subject, preferably to human, in the method of the present invention, at a therapeutically effective amount ranging from about 0.1 to about 100 mg/kg. Preferably, a therapeutically effective amount ranging from about 1 to about 20 mg/kg, more preferably a therapeutically effective amount ranging from about 3 to about 10 mg/kg is administered to a subject, preferably to human. A therapeutically effective amount of the humanized antibody or binding fragment thereof can be administered to the subject in one or more therapeutically effective doses.

Depending on the type and severity of the disease from about 0.1 mg/kg to about 100 mg/kg of antibody is an initial candidate dosage for administration to the subject, whether, for example, by one or more separate administrations, or by continuous infusion. A typical daily dosage to e.g. human might range from 0.1 mg/k to 20 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is readily monitored by those skilled in the art. According to toxicokinetics studies as described in example 6 the anti-α2 integrin antibodies of the present invention have an estimated half life T½ of between 199 and 316 hours. Thus a once every two weeks dosis regimen seems preferable.

Unexpectedly the anti-alpha 2 (α2) integrin antibodies used in the present invention inhibit tumor growth to a degree comparable to anti-VEGF antibodies. Specifically at a dose of 50 mg/kg of anti-alpha 2 (α2) integrin antibody administered biweekly for 22 days in a mouse xenograft study the size of the tumor was around 60% of the isotype control on day 27. Thus the invention provides a method of treating cancer selected from the group consisting of squamous cell cancer, lung cancer including small-cell lung cancer, non-small cell lung cancer, adenocarcinoma of the lung, and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema such as that associated with brain tumors, Meigs' syndrome, melanoma, mesothelioma, multiple myeloma, fibrosarcoma, osteosarcoma, and epidermoid carcinoma, by administering to a subject a therapeutically effective amount of a humanized anti-α2 integrin antibody, whereas the size of the tumor treated with the humanized anti-α2 integrin antibody is equal to or less than 90%, preferably equal to or less than 80%, more preferably equal to or less than 70%, most preferably equal to or less than 60%, in particular equal to or less than 50%, more particular equal to or less than 40%, most particular equal to or less than 30% of the size of the tumor treated with the control antibody, whereas the size of the tumor is usually measured as tumor volume or tumor weight.

An anti-α2 integrin antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, results from pharmacological and toxicity studies and other factors known to medical practitioners. A therapeutically effective amount of the antibody to be administered is determined by consideration of such, and is the minimum amount necessary to prevent, ameliorate, or treat an α2β1 integrin-associated disorder. Such amount is preferably below the amount that is toxic to the host or renders the host significantly more susceptible to infections.

The anti-α2 integrin antibody need not be, but may be optionally formulated, co-administered or used as an adjunct therapy with one or more agents currently used to prevent or treat the disorder in question. For example, the antibody may be given in conjunction with radiotherapy and or one or several cancer medications. These cancer medications may comprise another antibody, chemo-therapeutic agent, cytotoxic agent, anti-angiogenic agent, immunosuppressive agent, prodrug, cytokine, cytokine antagonist, cytotoxic radiotherapy, corticosteroid, anti-emetic cancer vaccine, analgesic, anti-vascular agent, or growth-inhibitory agent. More specific agents include, for example, irinotecan (CAMPTOSAR®), cetuximab (ERBITUX®), fulvestrant (FASLODEX®), vinorelbine (NAVELBINE®), EFG-receptor antagonists such as erlotinib (TARCEVA®) VEGF antagonists such as bevacizumab (AVASTIN®), vincristine (ONCOVIN®), inhibitors of mTor (a serine/threonine protein kinase) such as rapamycin and CCI-779, and anti-HER1, HER2, ErbB, and/or EGFR antagonists such as trastuzumab (HERCEPTIN®), pertuzumab (OMNI-TARG™), or Iapatinib, and other cytotoxic agents including chemotherapeutic agents. Alternatively, or in addition, α2β1 integrin antagonists may be administered to the mammal suffering from an α2β1 integrin-associated disorder. The effective amount of such other agents depends on the amount of anti-α2 integrin antibody present in the formulation, the type of disorder or treatment, and other factors discussed above. These are generally used in the same dosages and with administration routes as used hereinbefore or about from 1 to 99% of the heretofore employed dosages.

An article of manufacture containing materials, including an anti-α2 integrin antibody, useful for the treatment of the cancer as described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is an anti-alpha 2 integrin antibody. The label on, or associated with, the container indicates that the composition is used for treating the cancer as described above. The article of manufacture may further comprise a second container comprising a pharmaceutically-acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

The following examples are offered by way of illustration and not by way of limitation. The disclosures of all citations in the specification are expressly incorporated herein by reference.

EXAMPLES

Example 1

In Vitro Evaluation of Anti-$\alpha_2$ Integrin Antibody Potencies in Inhibiting Interaction Between Human $\alpha_2$ Integrin Expressed on Human Carcinoma Cell Lines and Human Collagen An in vitro binding assay between human cell line and human collagen has been established to assess the potency of different anti-$\alpha_2$ integrin antibodies to inhibit the interaction between human VLA-2 ($\alpha_2\beta_1$) integrin expressed on human carcinoma cell lines and human collagen type I. In this assay, fluorescently labelled human pancreatic cancer cell lines that naturally expresses VLA-2 were distributed in 96 well plates which have been previously coated with human collagen type I. A fluorescently labelled human pancreatic cancer cell line that doesn't express VLA-2 was used as a negative control. Fluorescently-labelled cells were then incubated in the collagen coated 96 well plates in presence of different concentrations of the anti-$\alpha_2$ integrin (GBR500 or TMC2206) or isotype-matched control antibody (GBR600) for one hour. Plates were gently washed and the remaining fluorescence was measured in each well of the plate. The strength of the fluorescence signal measured in each individual well is proportional to the number of cells that have adhered to the collagen.

Material and Methods

TABLE 1

| Antibodies | | | |
|---|---|---|---|
| Clone number or antibody name | Supplier | Catalogue number | Description |
| TMC-2206 | Glenmark/ Millipore | MAB1998 | Mouse anti-human $\alpha_2$ integrin |

TABLE 1-continued

Antibodies

| Clone number or antibody name | Supplier | Catalogue number | Description |
|---|---|---|---|
| GBR500 | Glenmark | NA | Humanized anti-human $\alpha_2$ integrin |
| GBR600 | Glenmark | NA | Humanized IgG$_4$ control antibody |

The humanized anti-human $\alpha_2$ integrin GBR500 as referred herein comprises a heavy chain comprising SEQ ID NO:187 and a light chain comprising SEQ ID NO:188.

TABLE 2

Cell lines

| Name | Source | Supplier | Cat# | VLA-2 expression |
|---|---|---|---|---|
| SK-BR-3 | Breast Carcinoma | ATCC | HTB-30 | Low |
| AsPC-1 | Pancreatic Carcinoma | ATCC | CRL-1682 | High |
| HPAF-II | Pancreatic Carcinoma | ATCC | CRL-1997 | High |
| MIA PaCa-2 | Pancreatic Carcinoma | ATCC | CRL-1420 | Negative |

Flow Cytometry

After incubation with Versene (Gibco, cat#15040), AsPC-1 cells, HPAF-II cells and MIA PaCa-2 cells were collected and resuspended in PBS-2.5% FBS at a concentration of $1\times10^6$ cells/mL. One hundred µl of the cell suspension was incubated with 10 µg/mL of GBR500-FITC or hIgG4-FITC as a control for 20 minutes on ice. Cells were washed twice with PBS-2.5% FBS and analyzed by flow cytometry. Trypsinised SK-BR-3 cell line were treated in the same way as described for the pancreatic cell line. Expression level of VLA-2 molecule was expressed as the Mean Fluorescence Intensity (MFI).

Collagen Binding Assay

Ninety six well ELISA plates (black cliniplate, Thermo Firsher scientific, cat no 9502867) were coated with 100 µl of human collagen type I (SIGMA, cat no C7774) at 50 µg/mL in Acetic Acid 0.02N or in PBS. Collagen was either diluted in acetic acid and incubated for 1 hour at 37° C. or diluted in PBS and incubated overnight at 4° C. Plates were blocked with 150 µl of PBS supplemented with 0.1% BSA or 1% BSA (Sigma, cat no A3059). Cells were first labelled with CFSE (Invitrogen cat no C34554) into serum free DMEM medium (PAA, cat no E15-005). Three µl of a 15 mM CFSE solution was added to 5 ml cells at a concentration between $1\times10^6$ cells/ml to $0.6\times10^6$ cells/ml. Cells were incubated with CFSE for 10 minutes at 37° C. and CFSE excess was removed by centrifugation of the cells at 900 rpm for 3 min. CFSE-labelled cells were resuspended at a concentration between $0.6\times10^6$ to $1\times10^6$ cells/ml in DMEM supplemented with 0.1% BSA. Fifty µl of antibody dilutions in DMEM-0.1% BSA were distributed to the collagen coated plate and fifty µl of CFSE labelled cells were immediately distributed to the plate. GBR600 antibody was used as an isotype control antibody for GBR500. Plates were incubated at room temperature for 1 hour and cells that were not bound to the collagen were removed by dumping the supernatant. Plates were washed four times with PBS buffer either manually or using BioTek washer. Wells in the plates were filled with PBS and fluorescence with excitation at 498 nm and emission at 525 nm was measured using Synerg HT2 fluorometer. Data were analyzed using PRISM software. Activity of the anti-VLA-2 antibody was expressed as $EC_{50}$ which is defined as the concentration of antibody that provokes a response halfway between the baseline and the maximum response.

Results:

TABLE 3

FACS staining

| | MFI | |
|---|---|---|
| Cell line | hIgG4 | GBR500 |
| AsPC-1 | 6.8 | 69.8 |
| HPAF-II | 14.9 | 166.5 |
| MIA PaCa-2 | 4.9 | 5.0 |
| SK-BR-3 | 3.4 | 6.0 |

Collagen Binding Assay

Collagen binding assay using the three pancreatic cancer cell lines and the breast cancer cell line were performed twice. Table 4 summarizes the EC-50 values obtained in the 2 experiments performed is depicted below.

TABLE 4

EC-50 values

| | Experiment I | | Experiment II | |
|---|---|---|---|---|
| Cell line | $EC_{50}$ GBR500 | $EC_{50}$ TMC2206 | $EC_{50}$ GBR500 | $EC_{50}$ TMC2206 |
| AsPC-1 | 0.047 µg/mL | 0.074 µg/mL | 0.036 µg/mL | 0.087 µg/mL |
| HPAF-II | 0.224 µg/mL | 0.3257 µg/mL | 0.103 µg/mL | 0.253 µg/mL |
| MIA Paca-2 | No cell binding | | No cell binding | |
| SK-BR-3 | 0.039 µg/mL | | 0.032 µg/mL | |

GBR500 and TMC-2206 antibodies inhibited the binding of the VLA-2 positive pancreatic and breast cancer cells to the human collagen. The MIA PaCa-2 cell line which doesn't express VLA-2 doesn't bind to the collagen. This result demonstrates that VLA-2 expression is a prerequisite for cell adherence to collagen type I.

CONCLUSION

1) α2 integrin expression on the carcinoma cancer cell lines AsPC-1, HPAF-II and SKBR3 cells can be detected using fluorescently-labelled GBR500 antibody. The pancreatic cancer cell line express a higher level of the α2 integrin compare to the breast cancer cell line.
2) The VLA-2 positive cell lines AsPC-1, HPAF-II and SK-BR-3 cell lines adhered to the collagen whereas the VLA-2 negative cell line MiaPaCA doesn't.
3) Antibody EC-50 values for the inhibition of collagen binding for the different cell lines tested are shown in Table 5:

TABLE 5

EC-50 values

| Cell lines | GBR500 $EC_{50}$ | TMC-2206 $EC_{50}$ |
|---|---|---|
| AsPC-1 | 0.041 ± 0.008 (n = 2) | 0.080 ± 0.009 (n = 2) |
| HPAF-II | 0.163 ± 0.086 (n = 2) | 0.290 ± 0.051 (n = 2) |
| MiaPaCa | No cell binding | No cell binding |
| SK-BR-3 | 0.036 ± 0.005 (n = 2) | Not done |

The EC$_{50}$ value obtained with the HPAF-II cell line was about 4 times (3.9 times for GBR500 and 3.6 for TMC-2206) higher compared to the EC$_{50}$ value measured for AsPC-1 cell line. This difference cannot be attributed to VLA-2 expression level, since both pancreatic cell lines expressed similar VLA-2 levels (see FACS staining data). Moreover, the SK-BR-3 cell line expressing a low level of VLA-2, displayed an EC$_{50}$ value comparable to AsPC-1 (high VLA-2 expression). However, the collagen coating conditions were different between the pancreatic cell lines and the breast cancer cell line (collagen diluted acid acetic at 37° C. for one hour versus collagen diluted in PBS at 4° C. overnight), therefore EC50 value comparisons between these cell lines should be interpreted with caution.

4) This study identifies $\alpha_2\beta_1$ integrin mediated adhesion to type I collagen as a potential therapeutic target. Moreover, the anti-VLA-2 antibody GBR500 and TMC2206 displayed a good capacity to inhibit the binding of VLA-2 expressing cell lines to collagen. GBR500 antibody is therefore a potential therapeutic candidate in the treatment of pancreatic and breast cancers.

Example 2

Effect of GBR500 Against the Human Pancreatic Carcinoma Tumour Xenograft AsPC-1 in BALB/c Nude (nu/nu) Athymic Mice Female BALB/c nude (nu/nu) athymic mice, of at least 6-8 weeks age were used in the xenograft study. Animals obtained from Australian Research Council (ARC) were assigned into treatment groups on day −2 of the study and treatment was being started as per the regime described in Table 6. On day 1 human AsPC-1 pancreatic carcinoma tumour cells (ATCC® Number: CRL-1682) were harvested from sub-confluent cultures grown in vitro and the number of viable cells determined. Cells were re-suspended in 1×PBS at a concentration of 5×10$^7$ cells/ml and animals were injected subcutaneously in the rear right flank with approximately 5×10$^6$ cells in a volume of 0.1 ml.

Animals were examined regularly for the appearance of tumours and dosed biweekly for 22 days starting from day −2 (Total 7 injections on days −2, 2, 6, 9, 13, 16, 20). Antibodies were administered in a volume of 10 ml/kg. At day 20 treatments were stopped and animals were monitored up to day 27.

TABLE 6

Treatment Groups and Study Design

| Group | Treatment | Dose level | Treatment Days | Route of administration | Number of animals |
|---|---|---|---|---|---|
| 1 | Isotype control | 50 mg/kg | biweekly* for 22 days | IP | 14 |
| 2 | Avastin ® | 40 mg/kg | biweekly for 22 days | IP | 14 |
| 3 | GBR500 | 5 mg/kg | biweekly for 22 days | IP | 14 |
| 4 | GBR500 | 50 mg/kg | biweekly for 22 days | IP | 14 |
| 5 | Cetuximab | 40 mg/kg | biweekly for 22 days | IP | 14 |

*Biweekly for 22 days starting from day −2 (Total 7 injections on days −2, 2, 6, 9, 13, 16, 20)

Tumour measurements were obtained twice weekly using digital callipers for the duration of the study. Tumour dimensions were recorded (length and width), and tumour volumes calculated using the formula W$^2$×L×0.536, where W is the widest tumour dimension and L is the longest. The results of the study are shown in FIG. 1. The tumor volumes refer to the mean per group of 14 animals. At a dose of 50 mg/kg GBR500, the size of the tumor was around 60% of the isotype control on day 27.

Example 3

Effect of GBR500 Against the HT29 Human Colon Carcinoma Xenograft in nu/nu Athymic Mice Nu/Nu male mice, from Harlan, Italy, were used. The animals were maintained in cages using steam autoclaved (sterile) bedding, diet and water were offered ad libitum. Animals were identified by a uniquely numbered ear-tag which appears on the data sheets. Body weight at the day of tumor implantation was: 24-31 g.

Number of Groups-Treatment Schedule:
Number of groups was 5. Number of animals/group was 10. Treatment was being started as per the regime described in Table 7.

TABLE 7

Treatment Groups and Study Design

| Group | Compound | Dose mg/kg | | Route/Schedule |
|---|---|---|---|---|
| 1 | IgG4 Isotype | 50 | IP* | Day 6, 9, 13, 16, 20, 23, 27** |
| 2 | Ha1/29 | 5 | IP | Day 6, 9, 13, 16, 20, 23, 27** |
| 3 | GBR500 | 50 | IP | Day 6, 9, 13, 16, 20, 23, 27** |
| 4 | Ha1/29 + GBR500 | 50 + 5 | IP | Day 6, 9, 13, 16, 20, 23, 27** |
| 5 | Avastin ® | 40 | IP | Day 6, 9, 13, 16, 20, 23, 27** |

*IP: intraperitoneally
**Treatment starts at day 6 after tumor implants

Substances:
Test compounds were stored at 4° C. temperature and protected from light until use. Test compounds were dissolved in 0.03% Tween-80™ in Phosphate buffered saline and were diluted immediately before use in order to reach the right concentration (IgG4 Isotype, Ha1/29 and GBR500 in PBS; Avastin® in saline solution). Treatments were administered intraperitoneally (IP) in a volume of 10 ml/kg Tumor:
HT29 tumor fragment from mice previously inoculated with HT29 cells (ATCC HTB-38™) were implanted subcutaneously into the left flank of athymic nude mice. Animals were examined regularly for the appearance of tumors. When measurable tumors have been established in the majority of mice, animals were assigned into treatment groups, with a target of 10 mice per group (5 mice per cage). When treatment starts the mean tumor volume was 120 mm$^3$.

Evaluation of Antitumor Activity in the Xenograft Models and Toxicity:
At least twice a week the tumor growth and the net body weight were evaluated. Tumor growth was assessed by caliper. Dimensions of the tumors were measured regularly by calliper during the experiments, and tumor masses were calculated as follows:

$$\text{Tumor weight (mg)} = \frac{\text{length (mm)} \cdot \text{width}^2 \text{ (mm)}}{2} \cdot d(mg/mm^3)$$

assuming density d=1 mg/mm$^3$ for tumor tissue

Toxicity was evaluated on the basis of the body weight reduction. Mice were sacrificed when the tumors reach a volume that hampers them.

Results and Conclusions:

Ha 1/29 (5 mg/kg) and GBR500 (50 mg/kg) administered as single agents twice a week, gave a tumor weight inhibition at day 28 of 12% and 16%, respectively. Ha1/29 in combination with GBR500 showed a reduction of tumor weight of 19% (Table 8).

TABLE 8

Dosage scheme and tumor weight inhibition

| Group | Compound | Dose mg/kg | % Tumor Weight Inhibition | | | | | | | |
|---|---|---|---|---|---|---|---|---|---|---|
| | | | 6 | 9 | 13 | 16 | 20 | 23 | 28 | 31 | 35 |
| 1 | IgG4 Isotype | 50 | — | — | — | — | — | — | — | — | — |
| 2 | Ha1/29 | 5 | 1 | 14 | 28 | 33 | 23 | 17 | 12 | 3 | −4 |
| 3 | GBR500 | 50 | 2 | 4 | 11 | 18 | 12 | 15 | 16 | 13 | 0 |
| 4 | Ha1/29 + GBR500 | 50 + 5 | 2 | 17 | 24 | 33 | 23 | 25 | 19 | 7 | −1 |
| 5 | Avastin ® | 40 | 1 | 20 | 28 | 43 | 44 | 50 | 50 | 40 | 24 |

Figure 2:
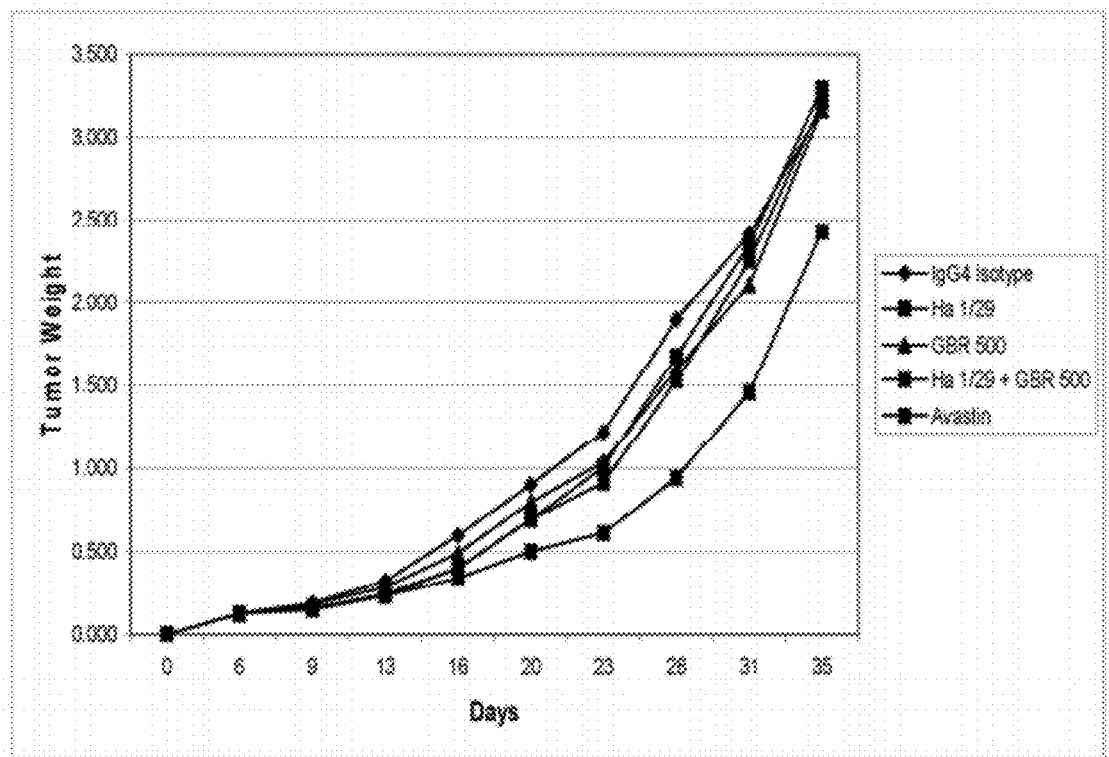
FIG. 2: Effect of GBR500 on HT29 human colon carcinoma xenograft in nu/nu athymic mice.

The maximal antitumor activity of antibodies treated groups was observed at day 16 with a tumor weight inhibition of 33, 18, 33% (Ha1/29, GBR500 and the combination group respectively). Avastin®, administered at 40 mg/kg, showed a tumor growth inhibition of 50% at day 28. In FIG. 2 the comparison of the average tumor growth observed in the different treatment groups is shown. Treatments were well tolerated and no dead mice in treated groups were found during the experiment. No signs of distress were observed during and after treatments and no significant body weight loss was observed.

Example 4

Detection of Expression Levels of CD49b (Integrin Subunit α2) in Human Cell Lines Cell Lines and Culture Conditions A panel of cell lysates was screened for expression of CD49b. This panel consisted of lysates from four non-transformed human cell lines (BJ, 1407, primary fibroblasts, WRL-68) and 96 human cancer cell lines from different tissues/organs (including colorectal, skin, breast, prostate, pancreas, lung, cervix, kidney, ovary, CNS, bone, liver, thyroid, and blood). The cell lines used are shown in Table 9 A and 9B.

TABLE 9A

Cell lines

| | Tissue tumor origin | Lane | Cell line | Source | Type | Growth medium |
|---|---|---|---|---|---|---|
| 1 | fibrosarcoma | 1 | HT-1080 | ECACC | ADHESION | E-MEM + 10% FCS + 2 mM L-Glutamine + 1% NEAA |
| 2 | adenocarcinoma colon | 2 | CACO-2 | 1st. Zooprofilattico BS | ADHESION | E-MEM + 10% FCS + 2 mM L-Glutamine + 1% NEAA |
| | | 3 | CL-11 | DSMZ | ADHESION | 80% mixture of Ham's F12 + Dulbecco's MEM (at E1) + 20% FBS |
| | | 4 | COLO-205 | NCI | ADHESION | RPMI 1640 + 10% FCS + 2 mM Glut |
| | | 5 | COLO-206F | DSMZ | ADHESION | RPMI 1640 + 10% FCS + 2 mM Glut. |
| | | 6 | COLO-320 | DSMZ | ADHESION | RPMI 1640 + 10% FCS + 2 mM Glut. |
| | | 7 | COLO-678 | DSMZ | ADHESION | RPMI 1640 + 10% FCS + 2 mM Glut. |
| | | 8 | COLO-741 | ICLC | ADHESION | RPMI 1640 + 10% FCS + 2 mM Glut. |
| | | 9 | DLD-1 | IEO (ATCC) | ADHESION | RPMI 1640 + 10% FCS + 2 mM Glut. + 10 mM HEPES, and 1.0 mM sodium pyruvate |
| | | 10 | HCC2998 | NCI | ADHESION | RPMI 1640 + 10% FCS + 2 mM Glut |
| | | 11 | HCT-116 | ECACC | ADHESION | McCoy's + 2 mM L-Glutamine + 10% FCS |
| | | 12 | HCT15 | NCI | ADHESION | RPMI 1640 + 10% FCS + 2 mM Glut |
| | | 13 | HT-29 | ECACC | ADHESION | McCoy's + 2 mM L-Glutamine + 10% FCS |
| | | 14 | KM12 | NCI | ADHESION | RPMI 1640 + 10% FCS + 2 mM Glut |
| | | 15 | LoVo | ECACC | ADHESION | HAM's F12 + 10% FCS + 2 mM Glut. |
| | | 16 | LS-174T | ATCC | ADHESION | E-MEM + 10% FCS + 2 mM L-Glutamine + 1% NEAA + 1% Na Pyruvate |
| | | 17 | LS-180 | ICLC | ADHESION | MEM(EBSS) + 10% FCS + 2 mM glutamine + 1% AAEE + 1% Sodium pyruvate |
| | | 18 | SW1417 | ICLC | ADHESION | RPMI 1640 + 10% FCS + 2 mM Glut |
| | | 19 | SW403 | DSMZ | ADHESION | DMEM + 2 mM glutamine + 10% |
| | | 20 | SW48 | ATCC | ADHESION | RPMI 1640 + 10% FCS + 2 mM Glut. |
| | | 21 | SW480 | IEO (ATCC) | ADHESION | Leibowitz's L-15 + 10% FCS + 2 mM Glutamine or RPMI + 10% fcs |
| | | 22 | SW620 | NCI | ADHESION | RPMI 1640 + 10% FCS + 2 mM Glut. |
| | | 23 | T84 | ATCC | ADHESION | HAM's F12 + DMEM E1 + 10% FCS |
| 3 | non tumoral | 24 | BJ | ATCC | ADHESION | D-MEM/M199 + 10% FCS + 2 mM Glut |
| | | 25 | I407 | PHA | ADHESION | EMEM(EBSS) + 2 mM Glutamine + 1% Non Essential Amino Acids (NEAA) + 10% Foetal Bovine Serum (FBS) |
| | | 26 | NHDF | PROMOCELL | ADHESION | Fibroblast basal medium + bullet kit + 1 ng/ml diFGF + 10% fcs |
| | | 27 | WRL-68 | ECACC | ADHESION | E-MEM + 10% FCS + 2 mM L-Glutamine + 1% NEAA |
| 4 | melanoma | 28 | A375 | ECACC | ADHESION | DMEM + 2 mM Glutamine + 10% FCS |
| | | 29 | Mewo | ATCC | ADHESION | E-MEM + 10% FCS + 2 mM L-Glutamine + 1% NEAA |
| | | 30 | SK-MEL-28 | NCI | ADHESION | RPMI 1640 + 10% FCS + 2 mM Glut. |
| | | 31 | SK-MEL-5 | ATCC | ADHESION | RPMI 1640 + 10% FCS + 2 mM Glut. |
| | | 32 | UACC-257 | NCI | ADHESION | RPMI 1640 + 10% FCS + 2 mM Glut |

TABLE 9A-continued

Cell lines

| Tissue tumor origin | Lane | Cell line | Source | Type | Growth medium |
|---|---|---|---|---|---|
| 5 adenocarcinoma mammary | 33 | BT-20 | ATCC | ADHESION | E-MEM + 10% FCS + 2 mM L-Glutamine |
| | 34 | MCF7 | NCI | ADHESION | RPMI 1640 + 10% FCS + 2 mM Glut |
| | 35 | MDA-MB-231 | NCI | ADHESION | RPMI 1640 + 10% FCS + 2 mM Glut |
| | 36 | MDA-MB-435S | NCI | ADHESION | RPMI 1640 + 10% FCS + 2 mM Glut |
| | 37 | MDA-MB-468 | ITM | ADHESION | RPMI or Leibowitz's L-15 + 10% FCS + 2 mM Glutamine |
| | 38 | SK-BR-3 | ATCC | ADHESION | McCoy's + 2 mM L-Glutamine + 10% FCS |
| | 39 | T47D | ATCC | ADHESION | RPMI 1640 + 10% FCS + 2 mM Glut |
| 6 carcinoma prostate | 40 | DU-145 | NCI | ADHESION | RPMI 1640 + 10% FCS + 2 mM Glut |
| | 41 | LnCap | ATCC | ADHESION | RPMI 1640 + 10% FCS + 2 mM Glut. + 10 Mm Hepes + 1 mM Na Pyruvate |
| | 42 | PC-3 | NCI | ADHESION | RPMI 1640 + 10% FCS + 2 mM Glut |
| 7 adenocarcinoma pancreas | 43 | BxPC-3 | ECACC | ADHESION | RPMI 1640 + 10% FCS + 2 mM Glut |
| | 44 | CAPAN-1 | DSMZ | ADHESION | RPMI 1640 + 10% FCS + 2 mM Glut |
| | 45 | MIA-PaCa-2 | ECACC | ADHESION | DMEM + 2 mM Glutamine + 10% FCS |
| | 46 | PANC-1 | ATCC | ADHESION | DMEM + 4 mM glutamine + 4.5 g/L glucose + 10% FCS |
| 8 non-small cell lung cancer | 47 | A549 | NCI | ADHESION | RPMI 1640 + 10% FCS + 2 mM Glut |
| | 48 | CAL-12T | IFOM | ADHESION | DMEM + 2 mM Glutamine + 10% FCS |
| | 49 | HOP-62 | NCI | ADHESION | RPMI 1640 + 10% FCS + 2 mM Glut |
| | 50 | NCI-H1437 | ATCC | ADHESION | RPMI 1640 + 10% FCS + 2 mM Glut |
| | 51 | NCI-H1770 | ATCC | SUSPENSION | RPMI 1640 + 10% FCS + 2 mM Glut |
| | 52 | SK-LU-1 | ICLC | ADHESION | MEM(EBSS) + 10% FCS + 2 mM glutamine + 1% AAEE + 1% Sodium pyruvate |

TABLE 9B

Cell lines

| Tissue tumor origin | Lane | Cell line | Source | Type | Growth medium |
|---|---|---|---|---|---|
| 9 adenocarcinoma cervix | 53 | C-33-A | IEO | ADHESION | RPMI 1640 + 10% FCS + 2 mM Glut. |
| | 54 | HeLa | ECACC | ADHESION | E-MEM + 10% FCS + 2 mM L-Glutamine + 1% NEAA |
| 10 adenocarcinoma kidney | 55 | A498 | NCI | ADHESION | RPMI 1640 + 10% FCS + 2 mM Glut |
| | 56 | ACHN | NCI | ADHESION | RPMI 1640 + 10% FCS + 2 mM Glut |
| | 57 | SN12C | NCI | ADHESION | RPMI 1640 + 10% FCS + 2 mM Glut |
| | 58 | TK10 | NCI | ADHESION | RPMI 1640 + 10% FCS + 2 mM Glut |
| | 59 | U031 | NCI | ADHESION | RPMI 1640 + 10% FCS + 2 mM Glut |
| 11 adenocarcinoma ovary | 60 | A2780 | ECACC | ADHESION | RPMI 1640 + 10% FCS + 2 mM Glut |
| | 61 | IGROV-1 | NCI | ADHESION | RPMI 1640 + 10% FCS + 2 mM Glut |
| | 62 | OVCAR-3 | NCI | ADHESION | RPMI 1640 + 10% FCS + 2 mM Glut |
| | 63 | OVCAR-8 | NCI | ADHESION | RPMI 1640 + 10% FCS + 2 mM Glut |
| 12 glioblastoma | 64 | SNB19 | NCI | ADHESION | RPMI 1640 + 10% FCS + 2 mM Glut |
| | 65 | T98G | ATCC | ADHESION | EMEM + 2 mM glut + 10% FCS + 1% AAEE + 1% (1.0 mM)sodium pyruvate |
| | 66 | U251 | NCI | ADHESION | RPMI 1640 + 10% FCS + 2 mM Glut |
| | 67 | U-87-MG | ATCC | ADHESION | E-MEM + 10% FCS + 2 mM L-Glutamine + 1% NEAA |
| 13 osteosarcoma | 68 | U-2-OS | ATCC | ADHESION | McCoy's + 2 mM L-Glutamine + 10% FCS |
| 14 non-small cell lung cancer | 69 | NCI-H1299 | ATCC | ADHESION | RPMI1640 + 10% FCS + 10 mM HEPES + 1 mM Na Pyruvate + 2 mM Glut. |
| | 70 | NCI-H1975 | ATCC | ADHESION | RPMI1640 + 20% FCS |
| 15 small cell lung cancer | 71 | NCI-H146 | ATCC | SUSPENSION | RPMI 1640 + 10% FCS + 2 mM Glut. + 10 mM HEPES, and 1.0 mM sodium pyruvate |
| | 72 | NCI-H1963 | ATCC | SUSPENSION | RPMI 1640 + 10% FCS + 2 mM Glut |
| | 73 | NCI-H209 | ATCC | SUSPENSION | RPMI 1640 medium, 90%; fetal bovine serum, 10% |
| | 74 | NCI-H526 | ATCC | SUSPENSION | RPMI 1640 + 10% FCS + 2 mM Glut. + 10 mM HEPES, and pyruvate + 1.0 mM sodium pyruvate |
| | 75 | NCI-H69 | ATCC | SUSPENSION | RPMI 1640 medium with 2 m 10 mM HEPES, and 1.0 mM sodium 10% FCSM L-glutamine |
| | 76 | NCI-H82 | ATCC | SUSPENSION | RPMI 1640 + 10% FCS + 2 mM Glut. + 10 mM HEPES, and 1.0 mM sodium pyruvate |
| | 77 | NCI-N592 | NMS | SUSPENSION | RPMI + 10% FCS + 1% HEPES + 1% Sodio Pyruvato |
| 16 adenocarcinoma liver | 78 | HepG2 | ECACC | ADHESION | E-MEM + 10% FCS + 2 mM L-Glutamine + 1% NEAA |
| 17 papillary thyroid carcinoma | 79 | WRO | Istituto Tumori | ADHESION | DMEM + Na piruvato + 10% fcs |
| 18 carcinoma epidermoid | 80 | A431 | ATCC | ADHESION | RPMI 1640 + 10% FCS + 2 mM Glut |
| 19 mesothelioma | 81 | MSTO-211H | Ospedale S. Matteo Pavia | ADHESION | RPMI 1640 + 10% FCS + 2 mM Glut. + 10 mM HEPES, and 1.0 mM sodium pyruvate |
| | 82 | REN | Ospedale S. Matteo Pavia | ADHESION | RPMI 1640 + 10% FCS + 2 mM Glut. |

TABLE 9B-continued

Cell lines

| Tissue tumor origin | Lane | Cell line | Source | Type | Growth medium |
|---|---|---|---|---|---|
| leukemia | 83 | HL-60 | ECACC | SUSPENSION | RPMI 1640 + 10% FCS + 2 mM Glut |
| leukemia | 84 | K-562 | ECACC | SUSPENSION | RPMI 1640 + 10% FCS + 2 mM Glut |
| leukemia T lymphoblastoid | 85 | CEM/VM1 | W. Beck-St Jude Hospital | SUSPENSION | E-MEM + 10% FCS + 2 mM L-Glutamine + 100 nM VM26 |
| leukemia T lymphoblastoid | 86 | KARPAS-299 | DSMZ | SUSPENSION | RPMI 1640 + 10% FCS + 2 mM glutamine |
| thrombocythemia leukemic | 87 | SET-2 | DSMZ | SUSPENSION | RPMI 1640 + 20% FBS |
| multiple myeloma | 88 | KMS-11 | Istituto Tumori | SUSPENSION | RPMI 1640 + 10% FCS + 2 mM glutamine |
| multiple myeloma | 89 | RPMI-8226 | ECACC | SUSPENSION | RPMI 1640 + 10% FCS + 2 mM Glut. |
| multiple myeloma | 90 | RPMI-8226 | DSMZ | SUSPENSION | RPMI 1640 + 10% FCS + 2 mM Glut. |
| Leukemia B cell | 91 | 697 | DSMZ | SUSPENSION | RPMI 1640 + 10% FCS + 2 mM Glut |
| Leukemia B cell | 92 | MEC-1 | DSMZ | SUSPENSION | 90% Iscove's MDM + 10% FBS |
| Leukemia B cell | 93 | NALM-6 | DSMZ | SUSPENSION | RPMI 1640 + 10% FCS + 2 mM glutamine |
| leukemia B cell | 94 | RS4-11 | ATCC | SUSPENSION | RPMI 1640 medium with 2 mM L-glutamine adjusted to contain 1.5 g/L sodium bicarbonate, 4.5 g/L glucose, 10 mM HEPES, and 1.0 mM sodium pyruvate, + 10% fetal bovine |
| Lymphoma B cell | 95 | GRANTA-519 | DSMZ | SUSPENSION | DMEM + 2 mM glutamine + 10% |
| Lymphoma B cell | 96 | SU-DHL-10 | DSMZ | SUSPENSION | 80-90% RPMI 1640 + 10-20% FBS |
| Lymphoma B cell | 97 | SU-DHL-4 | DSMZ | SUSPENSION | 80-90% RPMI 1640 + 10-20% FBS |
| Lymphoma B cell | 98 | SU-DHL-6 | DSMZ | SUSPENSION | 80-90% RPMI 1640 + 10-20% FBS |
| Lymphoma B cell | 99 | SUP-B15 | DSMZ | SUSPENSION | 80% McCoy's 5A + 20% FBS |
| Lymphoma | 100 | SUP-M2 | DSMZ | SUSPENSION | RPMI 1640 + 10% FCS + 2 mM Glut |

Lysate Preparation for Western Blot

The lysates are prepared from sub-confluent cultures of cell lines maintained in appropriate growth medium in the presence of 10% Foetal Bovine Serum (see table 8 for details). Adherent cell lines were seeded in 150 mm plates (cells harvested at approx. 60-70% confluency); suspension cell lines were grown in T-175 flasks (cells harvested at approx. 200,000 cells/ml).

Protocol for Adherent Cell Lines:
1) Wash plate with cold PBS (without Ca2+ and Mg2+). Remove PBS.
2) Allow excess PBS to drain to one side and remove.
3) Add 1 ml cold lysis buffer and put plate on ice. Scrape the cells.
4) Collect the lysate and wash the plate with another 200 µl lysis buffer and add to the lysate, agitate in cold room for 15 min.
6) Spin for 15 min in microfuge (15000 rpm at 4° C.).
7) Recover supernatant and freeze in aliquots in liquid Nitrogen.
8) Determine protein concentration in an aliquot of each lysate using a BSA reference curve.
9) Bring samples to 1 mg/ml with complete Lysis Buffer, 4× LDS Sample Buffer, 20× Reducing Agent (1M DTT) and boil 10 min.

Protocol for Suspension Cell Lines:
1) Spin cell suspension for 15 min (2000 rpm at 4° C.) and remove medium.
2) Wash with cold PBS (without Ca2+ and Mg2+), spin for 15 min (2000 rpm at 4° C.) and remove PBS.
3) Add 1 ml cold lysis buffer and pipette the cell lysate in ice.
4 Keep cell/lysate agitating in cold room for 15 min.
6) Spin for 15 min (15000 rpm at 4° C.).
7) Recover supernatant and freeze in aliquots in liquid Nitrogen.
8) Determine protein concentration in all lysates in parallel using the same BSA reference curve.
9) Bring samples to 1 mg/ml with Complete Lysis Buffer, 4× LDS Sample Buffer, 20× Reducing Agent (1M DTT) and boil 10 min.

Complete Lysis Buffer Composition:

| | |
|---|---|
| 50 mM | Hepes pH 7.5 |
| 150 mM | NaCl |
| 1% | Tritonx-100 |
| 1% | Deoxycholate |
| 0.1% | SDS |
| 10 mM | EDTA |

Add DTT (final 1 mM) and protease/phosphatase inhibitor cocktails (Sigma P-2850, P-5726, P-8340) as required just before use. DTT Reducing Agent (Biorad, cat. #161-0610): 50 mM final concentration.

LDS Sample Buffer Composition (Invitrogen, cat. #02 98 22 201):

| | |
|---|---|
| 106 mM | Tris HCl pH 8.5 |
| 150 mM | Tris base 1% TritonX-100 |
| 2% | LDS |
| 10% | glycerol |
| 0.51 mM | EDTA |
| 0.22 mM | Serva Blue G250 |
| 0.175 mM | Phenol Red |

Western Blot

Protein extracts (10 µg proteins/sample) were resolved by SDS-PAGE using 4-12% Bis-Tris Midi gels (Invitrogen) according to manufacturer's instructions. Membranes were stained with Ponceau Red after transfer. Anti-CD49b and anti-GAPDH antibodies were used diluted 1:1000 and 1:2000, respectively, in blocking buffer containing 5% non-fat dry milk. HRP-conjugated secondary antibodies were used 1:5000 in blocking buffer containing 5% non-fat dry milk.

Antibodies Used in the Study
- Mouse monoclonal IgG2a anti-CD49b (Integrin $\alpha_2$ chain) antibody (Becton Dickinson, cat. #611016);
- Rabbit polyclonal IgG anti-GAPDH (Glyceraldehyde 3-phosphate dehydrogenase) antibody (Santa Cruz Biotechnology, cat. # sc-25778);
- HRP-conjugated anti-mouse and anti-rabbit antibodies (Pierce);
- Biotin-GBR500 (lot AT-220208A) recombinant humanized monoclonal antibody;
- Biotin-IgG4 (lot AT-090108A) recombinant humanized monoclonal antibody (Glenmark Pharmaceuticals S.A.);
- Fluorolink™Cy™2 goat anti-mouse IgG (GE Healthcare, cat. # PA42002);
- Streptavidin-FITC (BD Pharmingen, ca. #554060).

Sample Preparation for Immunofluorescence

Cells were cultured in Lab-Tek chamber slides (Nunc) for 48 hours (70,000 cells/chamber), and afterwards fixed with formaldehyde 3.7% (v/v) for 20 minutes. Cells were washed twice with PBS, then saturated for 30 minutes with a blocking solution containing 1% (w/v) bovine serum albumin (BSA) and 0.3% (v/v) Triton X-100 (Sigma-Aldrich) in PBS. Primary antibodies were added at the recommended dilution in blocking solution. After 1 hour incubation at 37° C., the solution was removed and cells were washed twice with PBS.

Secondary antibodies, or alternatively Streptavidin-FITC, were added in blocking solution at the recommended dilution together with 1 mg/ml DRAQ5™ (Alexis, cat. # BOS-889-001-R200). Slides were incubated for 1 hour at 37° C., then the solution was removed and cells washed twice with PBS. PBS was removed and slides were mounted with coverslips using a Mowiol solution (Mowiol 4.88, Calbiochem cat. #475904).

Laser-Scanning Confocal Microscopy

Immunofluorescence pictures were obtained using an Axioplan microscope (Zeiss) coupled with a Radiance 2000 laser scanning system (Bio-Rad, 40× objective, oil immersion). Acquisition was performed using Kalman filter (10 iterations); laser power was equal for the same fluorescence channel in different samples.

Results and Conclusions

Western Blot Analysis of CD49b Expression in Human Cell Lines

Ponceau Red staining of membranes confirmed homogeneous transfer of cellular proteins to membrane.

Figure 3:
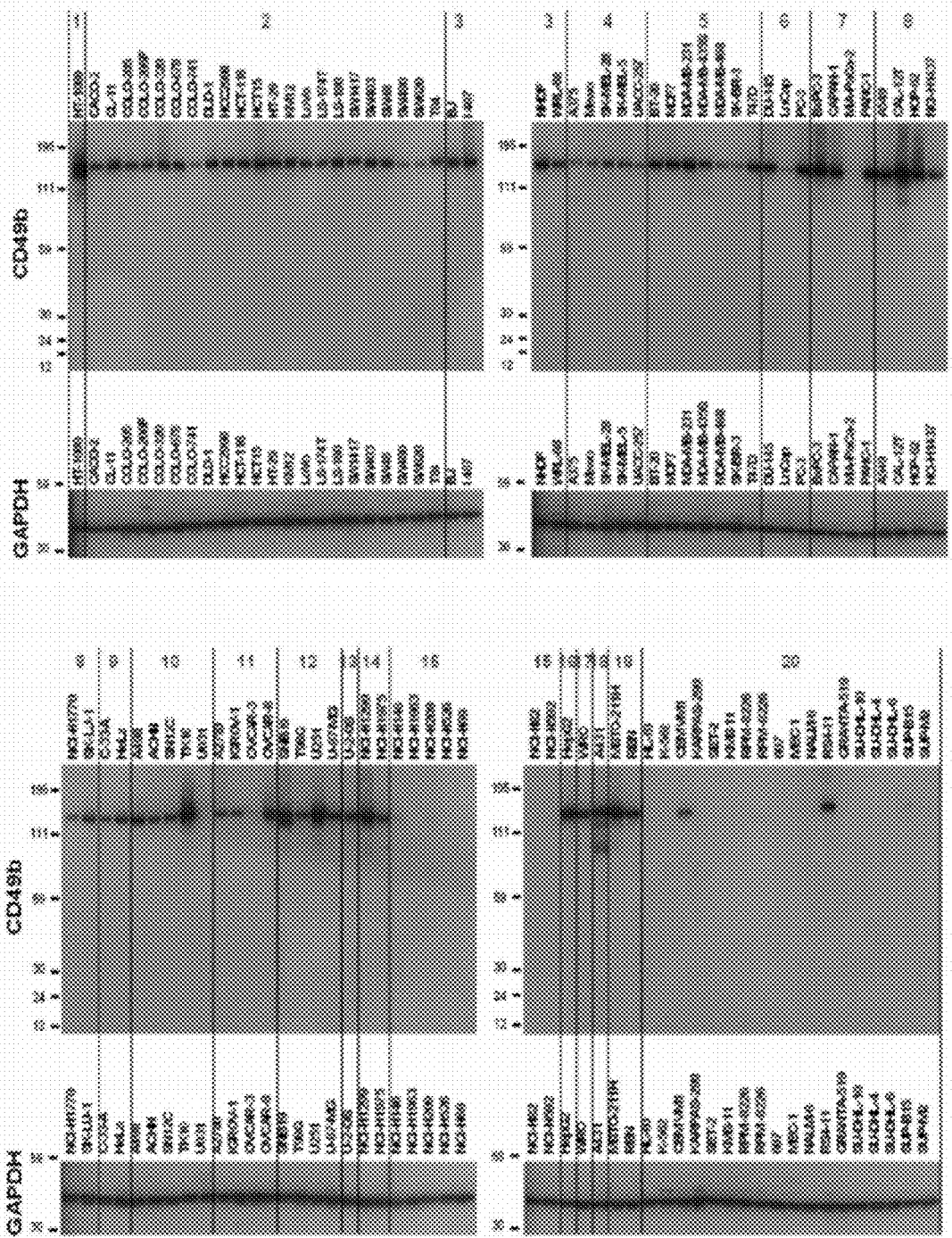
FIG. 3: Western Blot analysis of CD49b and GAPDH expression in human cell lines.

Western Blot analyses for CD49b and GAPDH expression are shown in FIG. 3. Overall, CD49b is ubiquitously expressed in adherent cell lines, but not in suspension ones (leukemias—block 15 and SCLCs—block 20). There are some exceptions of a few adherent cell lines with undetectable CD49b levels (for example, MIA PaCa-2 and U031), and conversely, of cell lines which grow in suspension expressing high CD49b levels (CEM/VM1 and RS4-11). All cell lines show consistent GAPDH expression, used as a loading/WB control.

The highest levels of CD49b were found in the following cell lines:
- HT-1080 (fibrosarcoma);
- BxPC-3 (adenocarcinoma pancreas);
- CAL-12T (non-small cell lung cancer);
- NCI-H1299 (non-small-cell lung cancer);
- TK10 (adenocarcinoma kidney);
- SNB19 and U251 (glioblastomas);
- A431 (epidermoid carcinoma).

Regarding colorectal carcinomas, the majority of the 22 tested lines exhibited homogenous, moderately high relative expression of CD49b. In only 3/22 tested lines, expression levels were relatively low, but still readily detectable by Western Blot.

CD49b Detection in Selected Cell Lines by Confocal Microscopy Using GBR500 Antibody Confocal microscopy was used to test whether Western Blot data obtained using Becton-Dickinson anti-CD49b correlated with cell surface expression using GBR500. In the samples studied, cell lines with high expression of the antigen as judged by Western blot were also found to exhibit specific immunoreactivity at the plasma membrane using GBR500. Human tumor cell lines which express CD49b at the plasma membrane and which therefore could be suitable for in vivo studies include HT-29 colorectal carcinoma and BX-PC3 pancreatic carcinoma lines, though many further candidates have been identified in this study.

Five selected cell lines (HT-1080, BxPC-3, MIAPaCa2, HT-29 and SW480) were immunostained with Biotin-GBR500 and biotin-hIgG4 (unrelated isotype) and analysed by laser-scanning confocal microscopy. These tumor cell lines were selected on the basis of results obtained by Western Blotting using BD anti-CD49b antibody:

BxPC-3: pancreatic carcinoma with high level of CD49b

MIAPaCa2: pancreatic carcinoma with undetectable CD49b

HT-29: colorectal carcinoma with moderately high level of CD49b

SW480: colorectal carcinoma with relatively low, but detectable level of CD49b

Figure 4:
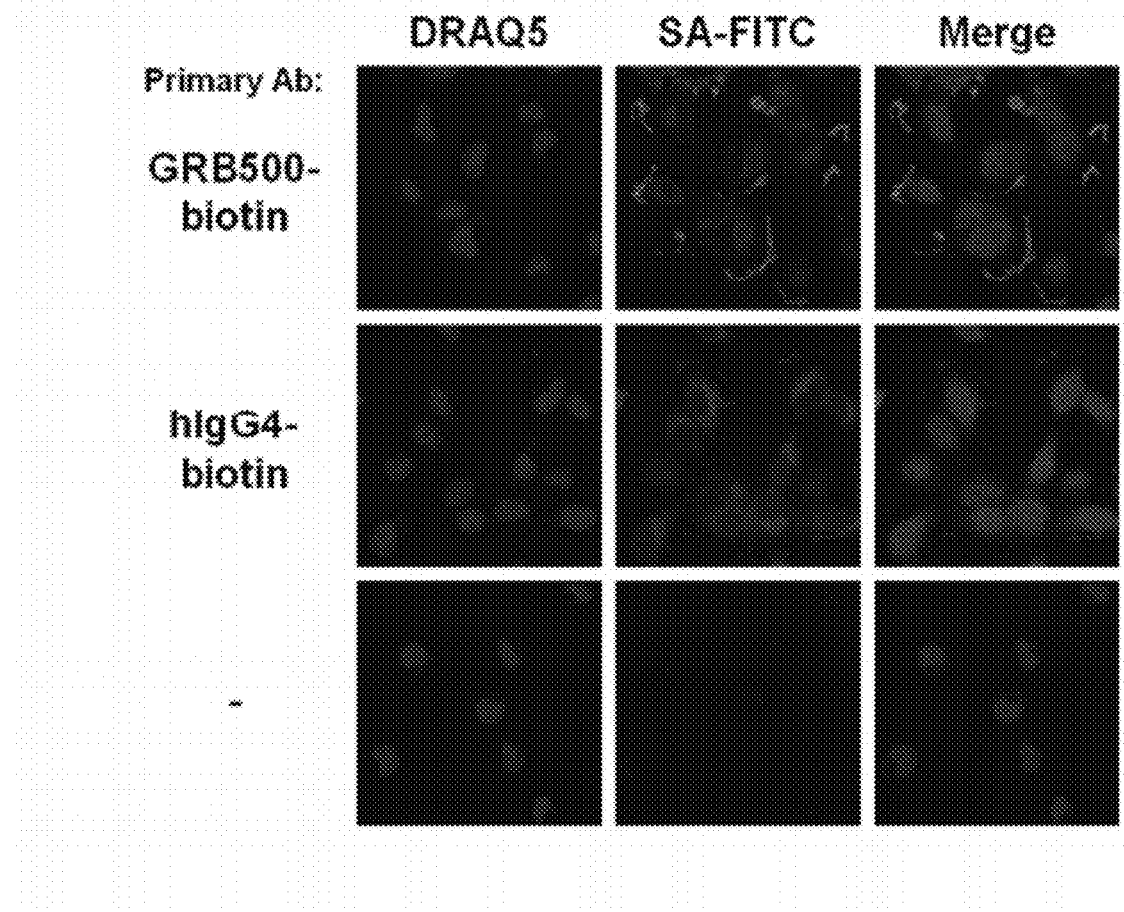
FIG. 4: Confocal microscopy images of stained cell line HT1080.

The fibrosarcoma cell line HT1080, known to express high levels of CD49b, was used as positive control: confocal microscopy confirms strong membrane staining concentrated at lamellipodia-like areas of the plasma membrane (FIG. 4).

Figure 5:
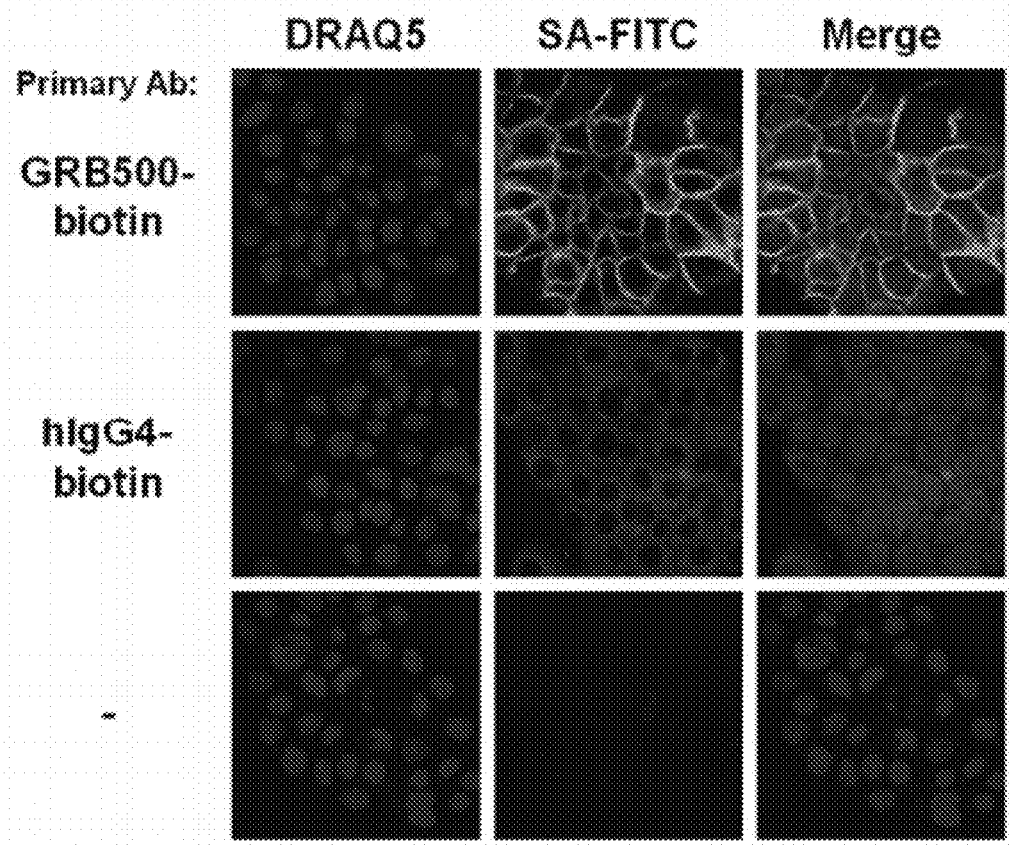
FIG. 5: Confocal microscopy images of stained cell line BxPC-3.
Figure 6:
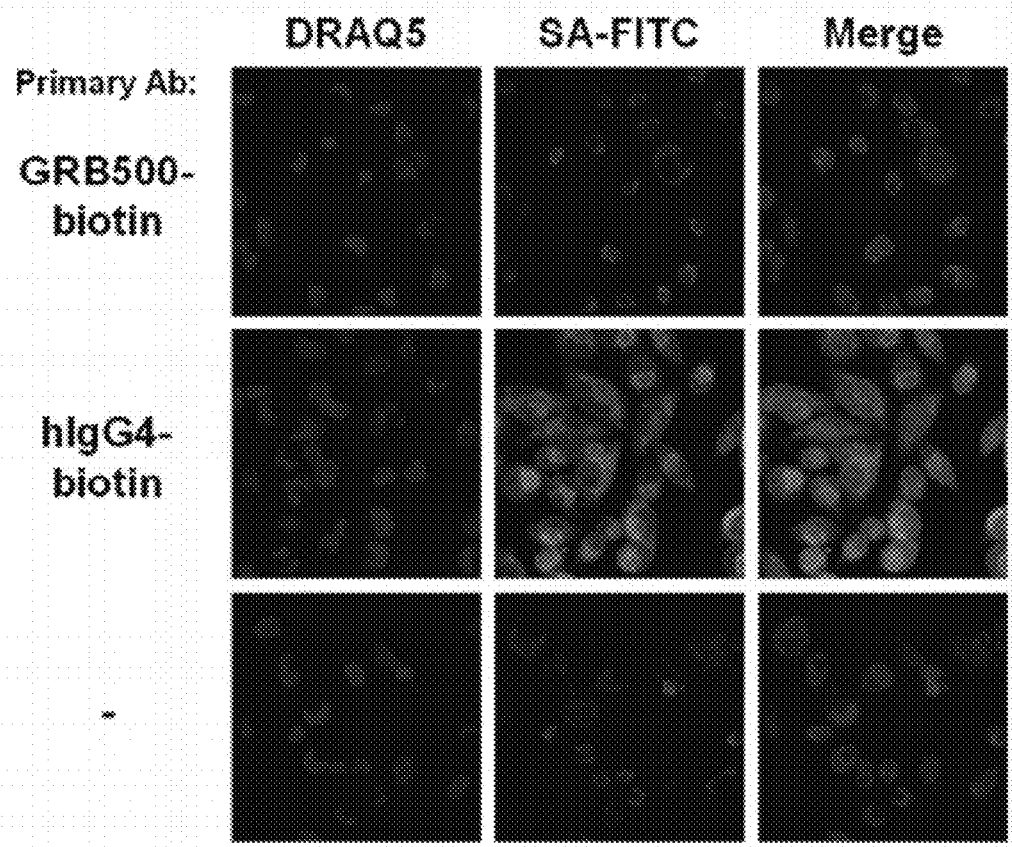
FIG. 6: Confocal microscopy images of stained cell line MIA PaCa2.

As shown in the images reported in FIG. 5 (BxPC-3) and FIG. 6 (MIA PaCa2) there does appear to be correlation between Western Blot data obtained with the BD antibody and immunocytochemistry results obtained with GBR500: BxPC-3 are strongly positive, while MIAPaCa2 are negative for staining with GBR500. In particular, confocal microscopy revealed strong biotin-GRB500, but not biotin-hIgG4, immunostaining of cell membrane within areas of cell-to-cell contact for BxPC-3. This is a distinct staining pattern compared to HT-1080 cells, where GBR500 staining is confined to possibly lamellipodia-like regions of the plasma membrane.

Figure 7:
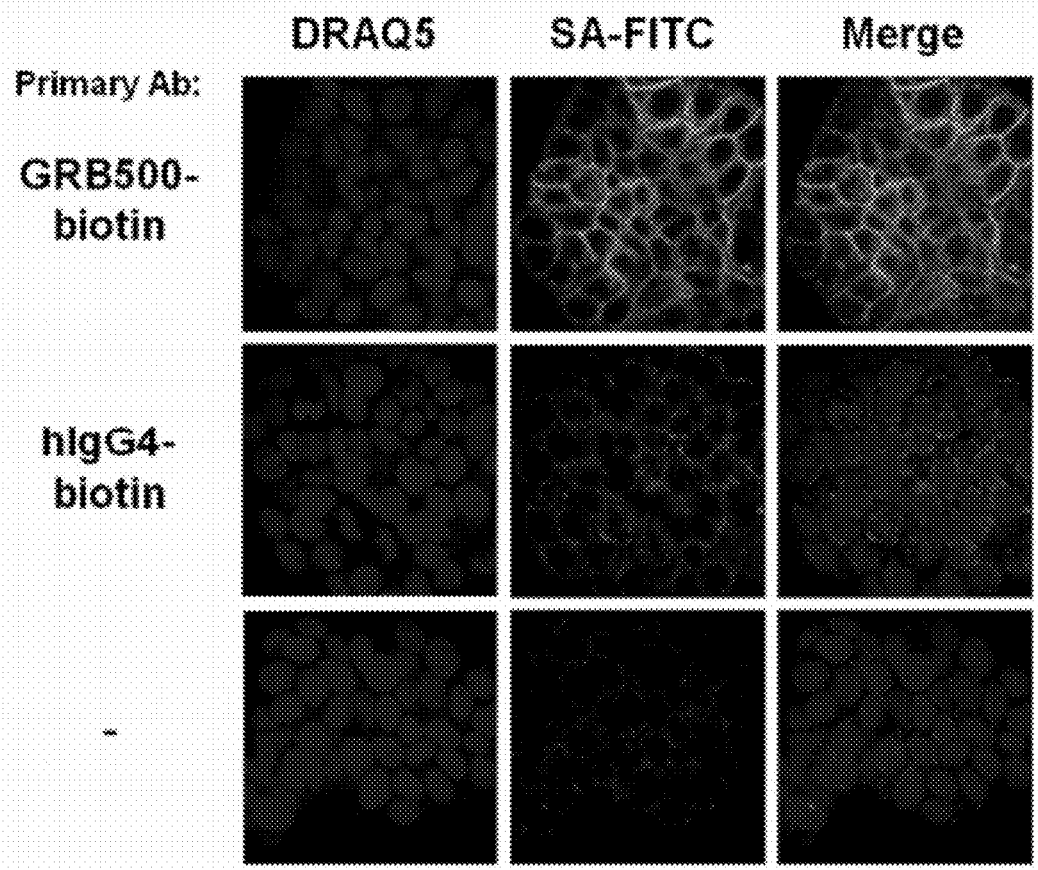
FIG. 7: Confocal microscopy images of stained cell line HT-29.

The colon adenocarcinoma cell line HT-29 showed intense biotin-GRB500 immunostaining (FIG. 7), with a distribution similar to that observed in BX-PC-3 cells.

In SW480 cells, another line with low CD49b expression as judged by Western Blot, biotin-GBR500 staining was nearly indistinguishable from biotin-IgG4 staining (FIG. 8), confirming a low CD49b expression level detected by Western Blot.

In conclusion, CD49b expression was detected in the majority of colon carcinoma cell lines, as well as several other solid tumor types, where it is commonly detected. CD49b expression is relatively rare in Small Cell Lung Carcinoma, and leukemias/lymphomas. Highest expressing cell lines as judged by Western Blot are HT-1080 (fibrosarcoma), BxPC-3 (pancreatic adenocarcinoma), CAL-12T (non-small cell lung cancer), NCI-H1299 (non-small-cell lung cancer), TK10 (renal adenocarcinoma), SNB19 and U251 (glioblastomas).

Example 5

Effect of GBR500 Against the A549 Non Small Cell Lung Cancer Xenograft in nu/nu Athymic Mice Nu/Nu male mice, from Harlan, Italy, were used. The animals were maintained in cages using steam autoclaved (sterile) bedding, diet and water were offered ad libitum. Animals were identified by a uniquely numbered ear-tag which appears on the data sheets. Body weight at the day of tumor implantation was: 24-31 g.
Number of groups-treatment schedule:
Number of groups was 4. Number of animals/group was 10. Treatment was being started at day 6 after tumor implantation until day 27 as per the regime described in Table 10.

TABLE 10

Treatment Groups and Study Design

| Group | Compound | Dose mg/kg | | Route/Schedule |
|---|---|---|---|---|
| 1 | IgG4 Isotype | 50 | IP* | Day 6, 9, 13, 16, 20, 23, 27** |
| 2 | Ha1/29 + GBR500 | 5 + 5 | IP | Day 6, 9, 13, 16, 20, 23, 27** |
| 3 | Ha1/29 + GBR500 | 5 + 50 | IP | Day 6, 9, 13, 16, 20, 23, 27** |
| 4 | Avastin ® | 40 | IP | Day 6, 9, 13, 16, 20, 23, 27** |

*IP: intraperitoneally
**Treatment starts at day 6 after tumor implants

Substances:

Test compounds were stored at 4° C. temperature and protected from light until use. Test compounds were dissolved in 0.03% Tween-80™ in Phosphate buffered saline and were diluted immediately before use in order to reach the right concentration (IgG4 Isotype, Ha1/29 and GBR500 in PBS; Avastin® in saline solution). Treatments were administered intraperitoneally (IP) in a volume of 10 ml/kg
Tumor:

The A549 epitelial lung carcinoma cell line (ATCC® Number: CCL-185) was used as a representative for non small lung cell cancer. Tumor fragments from a A549 xenograft were implanted subcutaneously into the left flank of athymic nude mice. Animals were examined regularly for the appearance of tumors. When measurable tumors have been established in the majority of mice, animals were assigned into treatment groups, with a target of 10 mice per group (5 mice per cage). When treatment starts the mean tumor volume was 120 mm³.
Evaluation of Antitumor Activity in the Xenograft Models and Toxicity:

At least twice a week the tumor growth and the net body weight were evaluated. Tumor growth was assessed by caliper. Dimensions of the tumors were measured regularly by calliper during the experiments, and tumor masses were calculated as follows:

$$\text{Tumor weight (mg)} = \frac{\text{length (mm)} \cdot \text{width}^2 \text{ (mm)}}{2} \cdot d(\text{mg}/\text{mm}^3)$$

assuming density d=1 mg/mm³ for tumor tissue
Toxicity was evaluated on the basis of the body weight reduction. Mice were sacrificed when the tumors reach a volume that hampers them.
Results and Conclusions:

As can be seen from Table 11 the maximal antitumor activity of antibodies treated groups was observed at day 17 with a tumor weight inhibition of 18% and 11% (Ha1/29+GBR500 combination groups respectively). Avastin®, administered at 40 mg/kg, showed a tumor growth inhibition of 20% at day 28. In FIG. 9 the comparison of the average tumor growth observed in the different treatment groups is shown. Treatments were well tolerated and no dead mice in treated groups were found during the experiment. No signs of distress were observed during and after treatments and no significant body weight loss was observed.

TABLE 11

Treatment Groups and Study Design

| | | Dose | % Tumor Weight Inhibition | | | | | |
|---|---|---|---|---|---|---|---|---|
| Group | Compound | mg/kg | 7 | 10 | 14 | 17 | 21 | 24 | 28 |
| 1 | IgG4 Isotype | 50 | — | — | — | — | — | — | — |
| 2 | Ha1/29 + GBR500 | 5 + 5 | −3 | 3 | 15 | 18 | 14 | 3 | 0% |
| 3 | Ha1/29 + GBR500 | 5 + 50 | −4 | 5 | 14 | 11 | 11 | 11 | 9 |
| 4 | Avastin ® | 40 | −4 | 3 | 10 | 12 | 17 | 18 | 20 |

Example 6

GBR500 Toxicokinetics in Cynomolgus Monkeys

As part of a 6-week toxicity study with toxicokinetic endpoints Cynomolgus monkeys were dosed via slow intravenous infusion of GBR 500 over approximately 60 minutes. The animals were dosed once per week for six weeks. (days 1, 8, 15, 22, 29, and 36). Dose Group Assignment and Dose Levels are summarized in Table 12 below:

TABLE 12

Dose Group Assignment and Dose Levels

| Group | Number of Males/Females | Dose Level (mg/kg) |
|---|---|---|
| 1 | 5/5 | 0 (control) |
| 2 | 3/3 | 10 |
| 3 | 3/3 | 30 |
| 4 | 3/3 | 100 |

Blood samples of 1 ml were taken from animals on Day 1 (predose, 15 minutes, 4, 8, 24, 48 and 120 hours post infusion, Day 8 (predose, 15 minutes post infusion), Day 15 (predose, 15 minutes post infusion), Day 22 (predose, 15 minutes post infusion), Day 29 (predose, 15 minutes post infusion), Day 36 (predose, 15 minutes, 4, 8, 24, 48 and 120 hours post infusion), and Days 50, 57, 64, 71, 78, 84, 91, and 98. GBR 500 concentration was determined with a validated ELISA assay.

The toxicokinetic (TK) profile of each animal was characterized by non-compartmental analysis of the GBR 500 serum concentration using validated computer software (WinNonlin, version 3.2, Pharsight Corp., Mountain View, Calif., USA). A model was selected based on the vascular route of administration and the serum matrix. The concentration at time zero on Day 1 was assumed to be 0 for the purpose of parameter estimation. Serum concentration values obtained at the predose time-point were used to estimate the concentration at time zero on Day 36.

Figure 10A:
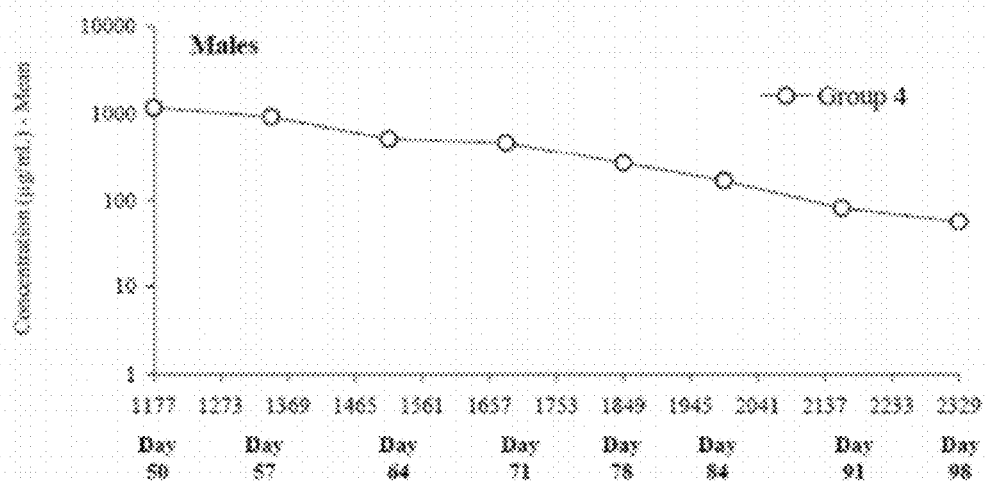
FIGS. 10A and 10B: Concentration curves of GBR500 100 mg dose group for male and female monkeys.
Figure 10B:
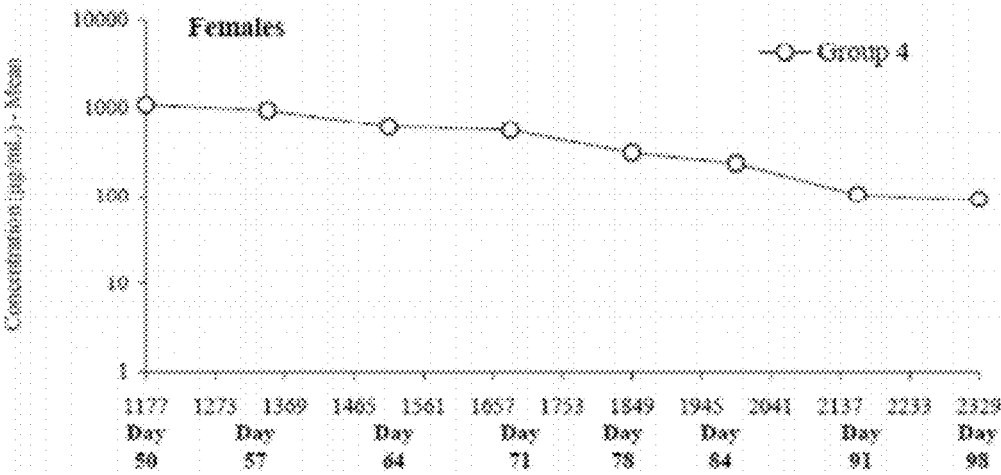

For the Group 4 recovery animals, the half life T½ was estimated between 199 and 316 hours, the volume of distribution Vz was estimated between 10.1-23.6 mL/kg, and the clearance CL between 0.03-0.60 mL/hr/kg. Vz and CL estimates indicated that GBR500 was not distributed beyond the plasma and was very slowly cleared from it. FIGS. 10A and 10B show the concentration curves of the 100 mg dose group for male and female monkeys.

Example 7

In vitro Evaluation of Anti-$\alpha_2$ Integrin Antibody Potencies in Inhibiting Interaction Between Human $\alpha_2$ Integrin Expressed on Human Fibrosarcoma Cell Line and Human Collagen Material and Methods Flow cytometry and collagen binding inhibition assays were performed as described in Example 1. A fibrosarcoma cell line HT-1080 was used in the experiments (Table 13). HT-1080 was trypsinized to prepare cells for flow cytometry as described for SK-BR-3

TABLE 13

Cell lines

| Name | Source | Supplier | Cat# | VLA-2 expression |
|---|---|---|---|---|
| HT-1080 | Fibrosarcoma | ATCC | CCL-121 | High |

Results

TABLE 14

FACS staining

| | MFI | |
|---|---|---|
| Cell line | hIgG4 | GBR500 |
| HT-1080 | 4.9 | 165.1 |

VLA-2 expression by HT-1080 was high.

Collagen Binding Assay

TABLE 15

EC-50 values

| Cell lines | GBR500 EC$_{50}$ | TMC-2206 EC$_{50}$ |
|---|---|---|
| HT-1080 | 0.076 ± 0.045 (n = 3) | 0.097 ± 0.038 (n = 3) |

GBR 500 and TMC-2206 inhibited binding of HT-1080 cells to human collagen I.

CONCLUSION $\alpha 2$ integrin expression on the fibrosarcoma cell line HT-1080 was detected using fluorescently-labelled GBR500 antibody. The level of expression VLA-2 is high. The VLA-2 positive cell line HT-1080 adhered to human collagen type I. This binding was inhibited by VLA-2 antibodies GBR 500 and TMC-2206.

Example 8

Effect of GBR500 Against the HT-1080 Fibrosarcoma Xenograft in nu/nu Athymic Mice Nu/Nu male mice, from Harlan, Italy, were used. The animals were maintained in cages using steam autoclaved (sterile) bedding, diet and water were offered ad libitum. Animals were identified by a uniquely numbered ear-tag which appears on the data sheets. Body weight at the day of tumor implantation was: 24-31 g.

Number of Groups-Treatment Schedule:

Number of groups was 4. Number of animals/group was 10. Treatment was being started as per the regime described in Table 16.

TABLE 16

Treatment Groups and Study Design

| Group | Compound | Dose mg/kg | Route/Schedule | |
|---|---|---|---|---|
| 1 | IgG4 Isotype | 50 | IP* | Day 6, 9, 13, 16, 20, 23, 27** |
| 2 | Ha1/29 + GBR500 | 5 + 5 | IP | Day 6, 9, 13, 16, 20, 23, 27** |
| 3 | Ha1/29 + GBR500 | 5 + 50 | IP | Day 6, 9, 13, 16, 20, 23, 27** |
| 4 | Avastin ® | 40 | IP | Day 6, 9, 13, 16, 20, 23, 27** |

*IP: intraperitoneally
**Treatment starts at day 6 after tumor implants

Substances:

Test compounds were stored at 4° C. temperature and protected from light until use. Test compounds were dissolved in 0.03% Tween-80™ in Phosphate buffered saline and were diluted immediately before use in order to reach the right concentration (IgG4 Isotype, Ha1/29 and GBR500 in PBS; Avastin® in saline solution). Treatments were administered intraperitoneally (IP) in a volume of 10 ml/kg.

Tumor:

The HT-1080 fibrosarcoma cell line (ATCC® Number: CCL-121) was used. Tumor fragments from a HT-1080 xenograft were implanted subcutaneously into the left flank of athymic nude mice. Animals were examined regularly for the appearance of tumors.

When measurable tumors have been established in the majority of mice, animals were assigned into treatment groups, with a target of 10 mice per group (5 mice per cage). When treatment starts the mean tumor volume was about 300 mm$^3$.

Evaluation of Antitumor Activity in the Xenograft Models and Toxicity:

At least twice a week the tumor growth and the net body weight were evaluated. Tumor growth was assessed by caliper. Dimensions of the tumors were measured regularly by calliper during the experiments, and tumor masses were calculated as follows:

$$\text{Tumor weight (mg)} = \frac{\text{length (mm)} \cdot \text{width}^2 \text{ (mm)}}{2} \cdot d(\text{mg}/\text{mm}^3)$$

assuming density d=1 mg/mm$^3$ for tumor tissue

Toxicity was evaluated on the basis of the body weight reduction. Mice were sacrificed when the tumors reach a volume that hampers them.

Results and Conclusions:

At day 11, after two doses of the antibody, Avastin led to a reduction of tumor weight of 31.6% relative to control. The Ha 1/29 5 mg/GBR500 5 mg combination led to a tumor weight reduction of 3.5% and the Ha 1/29 5 mg/GBR500 50 mg combination led to a tumor weight reduction of 27.7% (Table 17).

TABLE 17

Treatment Groups and Study Design

| Group | Compound | Dose mg/kg | % Tumor Weight Inhibition Day 11 Day 11 |
|---|---|---|---|
| 1 | IgG4 Isotype | 50 | 0 |
| 2 | Ha1/29 + GBR500 | 5 + 5 | 3.5 |
| 3 | Ha1/29 + GBR500 | 5 + 50 | 27.7 |
| 4 | Avastin ® | 40 | 31.6 |

Treatments were well tolerated and no dead mice in treated groups were found during the experiment. No signs of distress were observed during and after treatments and no significant body weight loss was observed.

SEQUENCE LISTING

```
<160> NUMBER OF SEQ ID NOS: 190

<210> SEQ ID NO 1
<211> LENGTH: 10
<212> TYPE: PRT
<213> ORGANISM: Homo Sapiens
<220> FEATURE:
<221> NAME/KEY: MISC_FEATURE
<223> OTHER INFORMATION: hCDR1 [CDR1 of heavy chain variable region]

<400> SEQUENCE: 1

Gly Phe Ser Leu Thr Asn Tyr Gly Ile His
1               5                   10

<210> SEQ ID NO 2
<211> LENGTH: 16
<212> TYPE: PRT
<213> ORGANISM: Homo Sapiens
<220> FEATURE:
<221> NAME/KEY: MISC_FEATURE
<223> OTHER INFORMATION: hCDR2  [CDR2 of heavy chain variable region]

<400> SEQUENCE: 2

Val Ile Trp Ala Arg Gly Phe Thr Asn Tyr Asn Ser Ala Leu Met Ser
1               5                   10                  15

<210> SEQ ID NO 3
<211> LENGTH: 11
<212> TYPE: PRT
<213> ORGANISM: Homo Sapiens
<220> FEATURE:
<221> NAME/KEY: MISC_FEATURE
<223> OTHER INFORMATION: hCDR3  [CDR3 of heavy chain variable region]

<400> SEQUENCE: 3

Ala Asn Asp Gly Val Tyr Tyr Ala Met Asp Tyr
1               5                   10

<210> SEQ ID NO 4
<211> LENGTH: 10
<212> TYPE: PRT
<213> ORGANISM: Homo Sapiens
<220> FEATURE:
<221> NAME/KEY: MISC_FEATURE
<223> OTHER INFORMATION: lCDR1 [CDR1 of light chain variable region]

<400> SEQUENCE: 4

Ser Ala Asn Ser Ser Val Asn Tyr Ile His
1               5                   10

<210> SEQ ID NO 5
```

```
<211> LENGTH: 7
<212> TYPE: PRT
<213> ORGANISM: Homo Sapiens
<220> FEATURE:
<221> NAME/KEY: MISC_FEATURE
<223> OTHER INFORMATION: lCDR2  [CDR2 of light chain variable region]

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Homo Sapiens
<220> FEATURE:
<221> NAME/KEY: MISC_FEATURE
<223> OTHER INFORMATION: lCDR3  [CDR3 of light chain variable region]

<400> SEQUENCE: 6

Gln Gln Trp Thr Thr Asn Pro Leu Thr
1               5

<210> SEQ ID NO 7
<211> LENGTH: 5361
<212> TYPE: DNA
<213> ORGANISM: Homo Sapiens
<220> FEATURE:
<221> NAME/KEY: misc_feature
<223> OTHER INFORMATION: Human alpha2 integrin DNA

<400> SEQUENCE: 7
ctgcaaaccc agcgcaacta cggtcccccg gtcagaccca ggatggggcc agaacggaca      60
ggggccgcgc cgctgccgct gctgctggtg ttagcgctca gtcaaggcat tttaaattgt     120
tgtttggcct acaatgttgg tctcccagaa gcaaaaatat tttccggtcc ttcaagtgaa     180
cagtttgggt atgcagtgca gcagtttata aatccaaaag caactggttt actggttggt     240
tcaccctgga gtggcttttcc tgagaaccga atgggagatg tgtataaatg tcctgttgac     300
ctatccactg ccacatgtga aaaactaaat ttgcaaactt caacaagcat tccaaatgtt     360
actgagatga aaccaacat gagcctcggc ttgatcctca ccaggaacat gggaactgga     420
ggttttctca catgtggtcc tctgtgggca cagcaatgtg ggaatcagta ttacacaacg     480
ggtgtgtgtt ctgacatcag tcctgatttt cagctctcag ccagcttctc acctgcaact     540
cagccctgcc cttccctcat agatgttgtg gttgtgtgtg atgaatcaaa tagtatttat     600
ccttgggatg cagtaaagaa ttttttggaa aaatttgtac aaggccttga tataggcccc     660
acaaagacac aggtgggggtt aattcagtat gccaataatc aagagttgt gtttaacttg     720 aacacatata aaaccaaaga gaaatgatt gtagcaacat cccagacatc ccaatatggt     780
ggggacctca aaacacatt cggagcaatt caatatgcaa gaaaatatgc ctattcagca     840
gcttctggtg ggcgacgaag tgctacgaaa gtaatggtag ttgtaactga cggtgaatca     900
catgatggtt caatgttgaa agctgtgatt gatcaatgca accatgacaa tatactgagg     960
tttggcatag cagttcttgg gtacttaaac agaaacgccc ttgatactaa aaatttaata    1020
aaagaaataa aagcgatcgc tagtattcca acagaaagat actttttcaa tgtgtctgat    1080
gaagcagctc tactagaaaa ggctgggaca ttaggagaac aaattttcag cattgaaggt    1140
actgttcaag gaggagacaa ctttcagatg gaaatgtcac aagtgggatt cagtgcagat    1200
tactcttctc aaaatgatat tctgatgctg ggtgcagtgg gagcttttgg ctggagtggg    1260
accattgtcc agaagacatc tcatggccat ttgatctttc ctaaacaagc ctttgaccaa    1320
```

```
attctgcagg acagaaatca cagttcatat ttaggttact ctgtggctgc aatttctact    1380
ggagaaagca ctcactttgt tgctggtgct cctcgggcaa attataccgg ccagatagtg    1440
ctatatagtg tgaatgagaa tggcaatatc acggttattc aggctcaccg aggtgaccag    1500
attggctcct attttggtag tgtgctgtgt tcagttgatg tggataaaga caccattaca    1560
gacgtgctct tggtaggtgc accaatgtac atgagtgacc taaagaaaga ggaaggaaga    1620
gtctacctgt ttactatcaa aaagggcatt ttgggtcagc accaatttct tgaaggcccc    1680
gagggcattg aaaacactcg atttggttca gcaattgcag ctctttcaga catcaacatg    1740
gatggcttta atgatgtgat tgttggttca ccactagaaa atcagaattc tggagctgta    1800
tacatttaca atggtcatca gggcactatc cgcacaaagt attcccagaa aatcttggga    1860
tccgatggag cctttaggag ccatctccag tactttggga ggtccttgga tggctatgga    1920
gatttaaatg gggattccat caccgatgtg tctattggtg cctttggaca gtggttcaa     1980
ctctggtcac aaagtattgc tgatgtagct atagaagctt cattcacacc agaaaaaatc    2040
actttggtca caagaatgc tcagataatt ctcaaactct gcttcagtgc aaagttcaga     2100
cctactaagc aaaacaatca agtggccatt gtatataaca tcacacttga tgcagatgga    2160
ttttcatcca gagtaacctc caggggggtta tttaaagaaa acaatgaaag gtgcctgcag    2220
aagaatatgg tagtaaatca agcacagagt tgccccgagc acatcattta tatacaggag    2280
ccctctgatg ttgtcaactc tttggatttg cgtgtggaca tcagtctgga aaaccctggc    2340
actagccctg cccttgaagc ctattctgag actgccaagg tcttcagtat tccttttccac   2400
aaagactgtg gtgaggatgg actttgcatt tctgatctag tcctagatgt ccgacaaata    2460
ccagctgctc aagaacaacc ctttattgtc agcaaccaaa acaaaaggtt aacattttca    2520
gtaacactga aaaataaaag ggaaagtgca tacaacactg gaattgttgt tgattttttca   2580
gaaaacttgt tttttgcatc attctcccta ccggttgatg ggacagaagt aacatgccag    2640
gtggctgcat ctcagaagtc tgttgcctgc gatgtaggct accctgcttt aaagagagaa    2700
caacaggtga ctttttactat taactttgac ttcaatcttc aaaaccttca gaatcaggcg    2760
tctctcagtt tccaagcctt aagtgaaagc caagaagaaa acaaggctga taatttggtc    2820
aacctcaaaa ttcctctcct gtatgatgct gaaattcact taacaagatc taccaacata    2880
aatttttatg aaatctcttc ggatgggaat gttccttcaa tcgtgcacag ttttgaagat    2940
gttggtccaa aattcatctt ctccctgaag gtaacaacag gaagtgttcc agtaagcatg    3000
gcaactgtaa tcatccacat ccctcagtat accaaagaaa agaacccact gatgtaccta    3060
actgggggtgc aaacagacaa ggctggtgac atcagttgta atgcagatat caatccactg    3120
aaaataggac aaacatcttc ttctgtatct ttcaaaagtg aaaatttcag gcacaccaaa    3180
gaattgaact gcagaactgc ttcctgtagt aatgttacct gctggttgaa agacgttcac    3240
atgaaaggag aatactttgt taatgtgact accagaattt ggaacgggac tttcgcatca    3300
tcaacgttcc agacagtaca gctaacggca gctgcagaaa tcaacaccta taccctgag    3360
atatatgtga ttgaagataa cactgttacg attcccctga tgataatgaa acctgatgag    3420
aaagccgaag taccaacagg agttataata ggaagtataa ttgctggaat ccttttgctg    3480
ttagctctgg ttgcaatttt atggaagctc ggcttcttca aaagaaaata tgaaaagatg    3540
accaaaaatc cagatgagat tgatgagacc acagagctca gtagctgaac cagcagacct    3600
acctgcagtg ggaaccggca gcatcccagc cagggtttgc tgtttgcgtg catggatttc    3660
ttttttaaatc ccatattttt tttatcatgt cgtaggtaaa ctaacctggt attttaagag    3720
```

```
aaaactgcag gtcagtttgg atgaagaaat tgtgggggt ggggagggtg cgggggcag      3780 gtagggaaat aatagggaaa atacctattt tatatgatgg gggaaaaaaa gtaatcttta      3840
aactggctgg cccagagttt acattctaat ttgcattgtg tcagaaacat gaaatgcttc      3900
caagcatgac aacttttaaa gaaaaatatg atactctcag attttaaggg ggaaaactgt      3960
tctctttaaa atatttgtct ttaaacagca actacagaag tggaagtgct tgatatgtaa      4020
gtacttccac ttgtgtatat tttaatgaat attgatgtta acaagagggg aaaacaaaac      4080
acaggttttt tcaatttatg ctgctcatcc aaagttgcca cagatgatac ttccaagtga      4140 taatttttatt tataaactag gtaaaatttg ttgttggttc cttttatacc acggctgccc      4200
cttccacacc ccatcttgct ctaatgatca aacatgcttt gaataactga gcttagagta      4260
tacctcctat atgtccattt aagttaggag agggggcgat atagagacta aggcacaaaa      4320
ttttgtttaa aactcagaat ataacattta tgtaaaatcc catctgctag aagcccatcc      4380
tgtgccagag gaaggaaaag gaggaaattt cctttctctt ttaggaggca caacagttct      4440
cttctaggat ttgtttggct gactggcagt aacctagtga attttgaaa gatgagtaat      4500 ttctttggca accttcctcc tcccttactg aaccactctc ccacctcctg gtggtaccat      4560
tattatagaa gccctctaca gcctgacttt ctctccagcg gtccaaagtt atcccctcct      4620 ttaccctca tccaaagttc ccactccttc aggacagctg ctgtgcatta gatattaggg      4680
gggaaagtca tctgtttaat ttacacactt gcatgaatta ctgtatataa actccttaac      4740
ttcagggagc tattttcatt tagtgctaaa caagtaagaa aaataagcta gagtgaattt      4800
ctaaatgttg gaatgttatg ggatgtaaac aatgtaaagt aaaacactct caggattttca      4860 ccagaagtta cagatgaggc actgaaaacc accaccaaat tagcaggtgc accttctgtg      4920
gctgtcttgt ttctgaagta cttttttcttc cacaagagtg aatttgacct aggcaagttt      4980
gttcaaaagg tagatcctga gatgatttgg tcagattggg ataaggccca gcaatctgca      5040
ttttaacaag caccccagtc actaggatgc agatggacca cactttgaga aacaccaccc      5100
atttctactt tttgcaccctt attttctctg ttcctgagcc cccacattct ctaggagaaa      5160
cttagattaa aattcacaga cactacatat ctaaagcttt gacaagtcct tgacctctat      5220
aaacttcaga gtcctcatta taaaatggga agactgagct ggagttcagc agtgatgctt      5280
tttagtttta aaagtctatg atctgatctg gacttcctat aatacaaata cacaatcctc      5340
caagaatttg acttggaaaa g                                                 5361
```

<210> SEQ ID NO 8
<211> LENGTH: 1181
<212> TYPE: PRT
<213> ORGANISM: Homo Sapiens
<220> FEATURE:
<221> NAME/KEY: MISC_FEATURE
<223> OTHER INFORMATION: Human alpha2 integrin

<400> SEQUENCE: 8

Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
                20                  25                  30

Gly Leu Pro Glu Ala Lys Ile Phe Ser Gly Pro Ser Ser Glu Gln Phe
            35                  40                  45

Gly Tyr Ala Val Gln Gln Phe Ile Asn Pro Lys Gly Asn Trp Leu Leu
        50                  55                  60

-continued

```
Val Gly Ser Pro Trp Ser Gly Phe Pro Glu Asn Arg Met Gly Asp Val
 65                  70                  75                  80

Tyr Lys Cys Pro Val Asp Leu Ser Thr Ala Thr Cys Glu Lys Leu Asn
                 85                  90                  95

Leu Gln Thr Ser Thr Ser Ile Pro Asn Val Thr Glu Met Lys Thr Asn
            100                 105                 110

Met Ser Leu Gly Leu Ile Leu Thr Arg Asn Met Gly Thr Gly Gly Phe
        115                 120                 125

Leu Thr Cys Gly Pro Leu Trp Ala Gln Gln Cys Gly Asn Gln Tyr Tyr
    130                 135                 140

Thr Thr Gly Val Cys Ser Asp Ile Ser Pro Asp Phe Gln Leu Ser Ala
145                 150                 155                 160

Ser Phe Ser Pro Ala Thr Gln Pro Cys Pro Ser Leu Ile Asp Val Val
                165                 170                 175

Val Val Cys Asp Glu Ser Asn Ser Ile Tyr Pro Trp Asp Ala Val Lys
            180                 185                 190

Asn Phe Leu Glu Lys Phe Val Gln Gly Leu Asp Ile Gly Pro Thr Lys
        195                 200                 205

Thr Gln Val Gly Leu Ile Gln Tyr Ala Asn Asn Pro Arg Val Val Phe
    210                 215                 220

Asn Leu Asn Thr Tyr Lys Thr Lys Glu Glu Met Ile Val Ala Thr Ser
225                 230                 235                 240

Gln Thr Ser Gln Tyr Gly Gly Asp Leu Thr Asn Thr Phe Gly Ala Ile
                245                 250                 255

Gln Tyr Ala Arg Lys Tyr Ala Tyr Ser Ala Ala Ser Gly Gly Arg Arg
            260                 265                 270

Ser Ala Thr Lys Val Met Val Val Val Thr Asp Gly Glu Ser His Asp
        275                 280                 285

Gly Ser Met Leu Lys Ala Val Ile Asp Gln Cys Asn His Asp Asn Ile
    290                 295                 300

Leu Arg Phe Gly Ile Ala Val Leu Gly Tyr Leu Asn Arg Asn Ala Leu
305                 310                 315                 320

Asp Thr Lys Asn Leu Ile Lys Glu Ile Lys Ala Ile Ala Ser Ile Pro
                325                 330                 335

Thr Glu Arg Tyr Phe Phe Asn Val Ser Asp Glu Ala Ala Leu Leu Glu
            340                 345                 350

Lys Ala Gly Thr Leu Gly Glu Gln Ile Phe Ser Ile Glu Gly Thr Val
        355                 360                 365

Gln Gly Gly Asp Asn Phe Gln Met Glu Met Ser Gln Val Gly Phe Ser
    370                 375                 380

Ala Asp Tyr Ser Ser Gln Asn Asp Ile Leu Met Leu Gly Ala Val Gly
385                 390                 395                 400

Ala Phe Gly Trp Ser Gly Thr Ile Val Gln Lys Thr Ser His Gly His
                405                 410                 415

Leu Ile Phe Pro Lys Gln Ala Phe Asp Gln Ile Leu Gln Asp Arg Asn
            420                 425                 430

His Ser Ser Tyr Leu Gly Tyr Ser Val Ala Ala Ile Ser Thr Gly Glu
        435                 440                 445

Ser Thr His Phe Val Ala Gly Ala Pro Arg Ala Asn Tyr Thr Gly Gln
    450                 455                 460

Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
                485                 490                 495
```

```
Ser Val Asp Val Asp Lys Asp Thr Ile Thr Asp Val Leu Leu Val Gly
            500                 505                 510

Ala Pro Met Tyr Met Ser Asp Leu Lys Lys Glu Glu Gly Arg Val Tyr
            515                 520                 525

Leu Phe Thr Ile Lys Lys Gly Ile Leu Gly Gln His Gln Phe Leu Glu
            530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
            565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
            595                 600                 605

Gly Ala Phe Arg Ser His Leu Gln Tyr Phe Gly Arg Ser Leu Asp Gly
            610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
            645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
            675                 680                 685

Lys Gln Asn Asn Gln Val Ala Ile Val Tyr Asn Ile Thr Leu Asp Ala
            690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
            725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
            755                 760                 765

Pro Ala Leu Glu Ala Tyr Ser Glu Thr Ala Lys Val Phe Ser Ile Pro
            770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
            805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
            835                 840                 845

Leu Phe Phe Ala Ser Phe Ser Leu Pro Val Asp Gly Thr Glu Val Thr
            850                 855                 860

Cys Gln Val Ala Ala Ser Gln Lys Ser Val Ala Cys Asp Val Gly Tyr
865                 870                 875                 880

Pro Ala Leu Lys Arg Glu Gln Gln Val Thr Phe Thr Ile Asn Phe Asp
            885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
```

```
                915                 920                 925
Lys Ile Pro Leu Leu Tyr Asp Ala Glu Ile His Leu Thr Arg Ser Thr
    930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
            965                 970                 975

Val Thr Thr Gly Ser Val Pro Val Ser Met Ala Thr Val Ile Ile His
            980                 985                 990

Ile Pro Gln Tyr Thr Lys Glu Lys Asn Pro Leu Met Tyr Leu Thr Gly
        995                 1000                1005

Val Gln Thr Asp Lys Ala Gly Asp Ile Ser Cys Asn  Ala Asp Ile
    1010                1015                1020

Asn Pro Leu Lys Ile Gly Gln  Thr Ser Ser Ser Val  Ser Phe Lys
    1025                1030                1035

Ser Glu Asn Phe Arg His Thr  Lys Glu Leu Asn Cys  Arg Thr Ala
    1040                1045                1050

Ser Cys Ser Asn Val Thr Cys  Trp Leu Lys Asp Val  His Met Lys
    1055                1060                1065

Gly Glu Tyr Phe Val Asn Val  Thr Thr Arg Ile Trp  Asn Gly Thr
    1070                1075                1080

Phe Ala Ser Ser Thr Phe Gln  Thr Val Gln Leu Thr  Ala Ala Ala
    1085                1090                1095

Glu Ile Asn Thr Tyr Asn Pro  Glu Ile Tyr Val Ile  Glu Asp Asn
    1100                1105                1110

Thr Val Thr Ile Pro Leu Met  Ile Met Lys Pro Asp  Glu Lys Ala
    1115                1120                1125

Glu Val Pro Thr Gly Val Ile  Ile Gly Ser Ile Ile  Ala Gly Ile
    1130                1135                1140

Leu Leu Leu Leu Ala Leu Val  Ala Ile Leu Trp Lys  Leu Gly Phe
    1145                1150                1155

Phe Lys Arg Lys Tyr Glu Lys  Met Thr Lys Asn Pro  Asp Glu Ile
    1160                1165                1170

Asp Glu Thr Thr Glu Leu Ser  Ser
    1175                1180

<210> SEQ ID NO 9
<211> LENGTH: 3700
<212> TYPE: DNA
<213> ORGANISM: Homo Sapiens
<220> FEATURE:
<221> NAME/KEY: misc_feature
<223> OTHER INFORMATION: Human beta1 integrin DNA

<400> SEQUENCE: 9
agccgccgcc acccgccgcg cccgacaccc gggaggcccc gccagcccgc gggagaggcc     60
cagcgggagt cgcggaacag caggcccgag cccaccgcgc cgggcccgg acgccgcgcg    120 gaaaagatga atttacaacc aattttctgg attggactga tcagttcagt ttgctgtgtg    180
tttgctcaaa cagatgaaaa tagatgttta aaagcaaatg ccaaatcatg tggagaatgt    240
atacaagcag ggccaaattg tgggtggtgc acaaattcaa catttttaca ggaaggaatg    300
cctacttctg cacgatgtga tgatttagaa gccttaaaaa agaagggttg ccctccagat    360
gacatagaaa atcccagagg ctccaaagat ataagaaaa ataaaaatgt aaccaaccgt    420
agcaaaggaa cagcagagaa gctcaagcca gaggatatta ctcagatcca accacagcag    480
```

-continued

```
ttggttttgc gattaagatc aggggagcca cagacattta cattaaaatt caagagagct    540
gaagactatc ccattgacct ctactacctt atggacctgt cttactcaat gaaagacgat    600
ttggagaatg taaaaagtct tggaacagat ctgatgaatg aaatgaggag gattacttcg    660
gacttcagaa ttggatttgg ctcatttgtg gaaaagactg tgatgcctta cattagcaca    720
acaccagcta agctcaggaa cccttgcaca agtgaacaga actgcaccag cccatttagc    780
tacaaaaatg tgctcagtct tactaataaa ggagaagtat ttaatgaact tgttggaaaa    840
cagcgcatat ctggaaattt ggattctcca gaaggtggtt tcgatgccat catgcaagtt    900
gcagtttgtg gatcactgat tggctggagg aatgttacac ggctgctggt gttttccaca    960
gatgccgggt ttcactttgc tggagatggg aaacttggtg gcattgtttt accaaatgat   1020
ggacaatgtc acctggaaaa taatatgtac acaatgagcc attattatga ttatccttct   1080
attgctcacc ttgtccagaa actgagtgaa aataatattc agacaatttt tgcagttact   1140
gaagaatttc agcctgttta caaggagctg aaaaacttga tccctaagtc agcagtagga   1200
acattatctg caaattctag caatgtaatt cagttgatca ttgatgcata caattccctt   1260
tcctcagaag tcattttgga aaacggcaaa ttgtcagaag gagtaacaat aagttacaaa   1320
tcttactgca agaacggggt gaatggaaca ggggaaaatg gaagaaaatg ttccaatatt   1380
tccattggag atgaggttca atttgaaatt agcataactt caaataagtg tccaaaaaag   1440
gattctgaca gctttaaaat taggcctctg ggctttacgg aggaagtaga ggttattctt   1500
cagtacatct gtgaatgtga atgccaaagc gaaggcatcc ctgaaagtcc caagtgtcat   1560
gaaggaaatg ggacatttga gtgtggcgcg tgcaggtgca atgaagggcg tgttggtaga   1620
cattgtgaat gcagcacaga tgaagttaac agtgaagaca tggatgctta ctgcaggaaa   1680
gaaaacagtt cagaaatctg cagtaacaat ggagagtgcg tctgcggaca gtgtgtttgt   1740
aggaagaggg ataatacaaa tgaaatttat tctggcaaat tctgcgagtg tgataatttc   1800
aactgtgata gatccaatgg cttaatttgt ggaggaaatg gtgtttgcaa gtgtcgtgtg   1860
tgtgagtgca cccccaacta cactggcagt gcatgtgact gttctttgga tactagtact   1920
tgtgaagcca gcaacggaca gatctgcaat ggccggggca tctgcgagtg tggtgtctgt   1980
aagtgtacag atccgaagtt tcaagggcaa acgtgtgaga tgtgtcagac ctgccttggt   2040
gtctgtgctg agcataaaga atgtgttcag tgcagagcct tcaataaagg agaaaagaaa   2100
gacacatgca cacaggaatg ttcctatttt aacattacca aggtagaaag tcgggacaaa   2160
ttaccccagc cggtccaacc tgatcctgtg tcccattgta aggagaagga tgttgacgac   2220
tgttggttct attttacgta ttcagtgaat gggaacaacg aggtcatggt tcatgttgtg   2280
gagaatccag agtgtcccac tggtccagac atcattccaa ttgtagctgg tgtggttgct   2340
ggaattgttc ttattggcct tgcattactg ctgatatgga agcttttaat gataattcat   2400
gacagaaggg agtttgctaa atttgaaaag gagaaaatga atgccaaatg ggacacgggt   2460
gaaaatccta tttataagag tgccgtaaca actgtggtca atccgaagta tgagggaaaa   2520
tgagtactgc ccgtgcaaat cccacaacac tgaatgcaaa gtagcaattt ccatagtcac   2580
agttaggtag cttagggca atattgccat ggttttactc atgtgcaggt tttgaaaatg   2640
tacaatatgt ataattttta aaatgtttta ttattttgaa aataatgttg taattcatgc   2700
cagggactga caaaagactt gagacaggat ggttattctt gtcagctaag gtcacattgt   2760 gccttttttga ccttttcttc ctggactatt gaaatcaagc ttattggatt aagtgatatt   2820
tctatagcga ttgaaagggc aatagttaaa gtaatgagca tgatgagagt ttctgttaat   2880
```

-continued

```
catgtattaa aactgatttt tagctttaca aatatgtcag tttgcagtta tgcagaatcc    2940
aaagtaaatg tcctgctagc tagttaagga ttgttttaaa tctgttattt tgctatttgc    3000
ctgttagaca tgactgatga catatctgaa agacaagtat gttgagagtt gctggtgtaa    3060
aatacgtttg aaatagttga tctacaaagg ccatgggaaa aattcagaga gttaggaagg    3120
aaaaaccaat agctttaaaa cctgtgtgcc attttaagag ttacttaatg tttggtaact    3180
tttatgcctt cactttacaa attcaagcct tagataaaag aaccgagcaa ttttctgcta    3240
aaaagtcctt gatttagcac tatttacata caggccatac tttacaaagt atttgctgaa    3300
tggggacctt ttgagttgaa tttattttat tatttttatt ttgtttaatg tctggtgctt    3360
tctatcacct cttctaatct tttaatgtat ttgtttgcaa ttttggggta agactttttt    3420
atgagtactt tttctttgaa gttttagcgg tcaatttgcc tttttaatga acatgtgaag    3480
ttatactgtg gctatgcaac agctctcacc tacgcgagtc ttactttgag ttagtgccat    3540
aacagaccac tgtatgttta cttctcacca tttgagttgc ccatcttgtt tcacactagt    3600
cacattcttg ttttaagtgc ctttagtttt aacagttcac tttttacagt gctatttact    3660
gaagttattt attaaatatg cctaaaatac ttaaatcgga                         3700
```

```
<210> SEQ ID NO 10
<211> LENGTH: 798
<212> TYPE: PRT
<213> ORGANISM: Homo Sapiens
<220> FEATURE:
<221> NAME/KEY: MISC_FEATURE
<223> OTHER INFORMATION: Human beta1 integrin

<400> SEQUENCE: 10
```

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
    210                 215                 220
```

```
Leu Thr Asn Lys Gly Glu Val Phe Asn Glu Leu Val Gly Lys Gln Arg
225                 230                 235                 240

Ile Ser Gly Asn Leu Asp Ser Pro Glu Gly Phe Asp Ala Ile Met
            245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
            290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
            325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
            370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
            405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
            435                 440                 445

Gly Phe Thr Glu Glu Val Glu Val Ile Leu Gln Tyr Ile Cys Glu Cys
            450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
            485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
            515                 520                 525

Gly Glu Cys Val Cys Gly Gln Cys Val Cys Arg Lys Arg Asp Asn Thr
530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
            565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
            595                 600                 605

Gly Arg Gly Ile Cys Glu Cys Gly Val Cys Lys Cys Thr Asp Pro Lys
            610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
```

```
                    645                 650                 655
Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
            675                 680                 685

Ser His Cys Lys Glu Lys Asp Val Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
                755                 760                 765

Glu Lys Met Asn Ala Lys Trp Asp Thr Gly Glu Asn Pro Ile Tyr Lys
            770                 775                 780

Ser Ala Val Thr Thr Val Val Asn Pro Lys Tyr Glu Gly Lys
785                 790                 795

<210> SEQ ID NO 11
<211> LENGTH: 226
<212> TYPE: PRT
<213> ORGANISM: Homo Sapiens
<220> FEATURE:
<221> NAME/KEY: MISC_FEATURE
<223> OTHER INFORMATION: Human alpha2 I domain

<400> SEQUENCE: 11

Ser Pro Asp Phe Gln Leu Ser Ala Ser Phe Ser Pro Ala Thr Gln Pro
1               5                   10                  15

Cys Pro Ser Leu Ile Asp Val Val Val Val Cys Asp Glu Ser Asn Ser
            20                  25                  30

Ile Tyr Pro Trp Asp Ala Val Lys Asn Phe Leu Glu Lys Phe Val Gln
        35                  40                  45

Gly Leu Asp Ile Gly Pro Thr Lys Thr Gln Val Gly Leu Ile Gln Tyr
50                  55                  60

Ala Asn Asn Pro Arg Val Val Phe Asn Leu Asn Thr Tyr Lys Thr Lys
65                  70                  75                  80

Glu Glu Met Ile Val Ala Thr Ser Gln Thr Ser Gln Tyr Gly Gly Asp
                85                  90                  95

Leu Thr Asn Thr Phe Gly Ala Ile Gln Tyr Ala Arg Lys Tyr Ala Tyr
            100                 105                 110

Ser Ala Ala Ser Gly Gly Arg Arg Ser Ala Thr Lys Val Met Val Val
        115                 120                 125

Val Thr Asp Gly Glu Ser His Asp Gly Ser Met Leu Lys Ala Val Ile
130                 135                 140

Asp Gln Cys Asn His Asp Asn Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175

Ile Lys Ala Ile Ala Ser Ile Pro Thr Glu Arg Tyr Phe Phe Asn Val
            180                 185                 190

Ser Asp Glu Ala Ala Leu Leu Glu Lys Ala Gly Thr Leu Gly Glu Gln
        195                 200                 205

Ile Phe Ser Ile Glu Gly Thr Val Gln Gly Gly Asp Asn Phe Gln Met
```

```
                          210                 215                 220
Glu Met
225

<210> SEQ ID NO 12
<211> LENGTH: 71
<212> TYPE: PRT
<213> ORGANISM: Homo Sapiens
<220> FEATURE:
<221> NAME/KEY: MISC_FEATURE
<223> OTHER INFORMATION: FW1-3 4-59 [FW=1-25; FW2=26-39; FW3=40-71]

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Thr Val Ser Trp Ile Arg Gln Pro Pro Gly
            20                  25                  30

Lys Gly Leu Glu Trp Ile Gly Arg Val Thr Ile Ser Val Asp Thr Ser
        35                  40                  45

Lys Asn Gln Phe Ser Leu Lys Leu Ser Ser Val Thr Ala Ala Asp Thr
    50                  55                  60

Ala Val Tyr Tyr Cys Ala Arg
65                  70

<210> SEQ ID NO 13
<211> LENGTH: 11
<212> TYPE: PRT
<213> ORGANISM: Homo Sapiens
<220> FEATURE:
<221> NAME/KEY: MISC_FEATURE
<223> OTHER INFORMATION: FW4 4-59 [NCBI entry gi/33583]

<400> SEQUENCE: 13

Trp Gly Gln Gly Thr Leu Val Thr Val Ser Ser
1               5                   10

<210> SEQ ID NO 14
<211> LENGTH: 27
<212> TYPE: DNA
<213> ORGANISM: Homo Sapiens
<220> FEATURE:
<221> NAME/KEY: misc_feature
<223> OTHER INFORMATION: VHL-for [forward primer]

<400> SEQUENCE: 14
ccatggctgt cttggggctg ctcttct                                          27

<210> SEQ ID NO 15
<211> LENGTH: 17
<212> TYPE: DNA
<213> ORGANISM: Homo Sapiens
<220> FEATURE:
<221> NAME/KEY: misc_feature
<223> OTHER INFORMATION: HC-rev [reverse primer]

<400> SEQUENCE: 15
ggggccagtg gatagac                                                     17

<210> SEQ ID NO 16
<211> LENGTH: 28
<212> TYPE: DNA
<213> ORGANISM: Homo Sapiens
<220> FEATURE:
<221> NAME/KEY: misc_feature
<223> OTHER INFORMATION: VLL-for [forward primer]
```

<400> SEQUENCE: 16
ccatggattt tcaagtgcag attttcag                                              28

<210> SEQ ID NO 17
<211> LENGTH: 17
<212> TYPE: DNA
<213> ORGANISM: Homo Sapiens
<220> FEATURE:
<221> NAME/KEY: misc_feature
<223> OTHER INFORMATION: LCkappa-rev [reverse primer]

<400> SEQUENCE: 17
gttggtgcag catcagc                                                          17

<210> SEQ ID NO 18
<211> LENGTH: 318
<212> TYPE: DNA
<213> ORGANISM: Homo Sapiens
<220> FEATURE:
<221> NAME/KEY: misc_feature
<223> OTHER INFORMATION: TMC-2206 VL
<220> FEATURE:
<221> NAME/KEY: CDS
<222> LOCATION: (1)..(318)

<400> SEQUENCE: 18 caa ttt gtt ctc acc cag tct cca gca ttc ttg tct gct tct cca ggg     48
Gln Phe Val Leu Thr Gln Ser Pro Ala Phe Leu Ser Ala Ser Pro Gly
1               5                   10                  15 gag aag gtc acc atg acc tgc agt gcc aac tca agt gtg aat tac att     96
Glu Lys Val Thr Met Thr Cys Ser Ala Asn Ser Ser Val Asn Tyr Ile
            20                  25                  30 cac tgg tac cag cag aag tca ggc acc tcc ccc aaa aaa tgg att tat    144
His Trp Tyr Gln Gln Lys Ser Gly Thr Ser Pro Lys Lys Trp Ile Tyr
        35                  40                  45 gac act tcc aaa ctg gct tct gga gtc cct gtt cgc ttc agt ggc agt    192
Asp Thr Ser Lys Leu Ala Ser Gly Val Pro Val Arg Phe Ser Gly Ser
    50                  55                  60 gga tct ggg acc tct tac tct ctc aca atc agc agc atg gag act gag    240
Gly Ser Gly Thr Ser Tyr Ser Leu Thr Ile Ser Ser Met Glu Thr Glu
65                  70                  75                  80 gat gct gcc act tat tac tgc cag cag tgg act act aac cca ctc acg    288
Asp Ala Ala Thr Tyr Tyr Cys Gln Gln Trp Thr Thr Asn Pro Leu Thr
                85                  90                  95 ttc ggt gct ggg acc agg gtg gag ctg aaa                            318
Phe Gly Ala Gly Thr Arg Val Glu Leu Lys
            100                 105

<210> SEQ ID NO 19
<211> LENGTH: 106
<212> TYPE: PRT
<213> ORGANISM: Homo Sapiens

<400> SEQUENCE: 19

Gln Phe Val Leu Thr Gln Ser Pro Ala Phe Leu Ser Ala Ser Pro Gly
1               5                   10                  15

Glu Lys Val Thr Met Thr Cys Ser Ala Asn Ser Ser Val Asn Tyr Ile
            20                  25                  30

His Trp Tyr Gln Gln Lys Ser Gly Thr Ser Pro Lys Lys Trp Ile Tyr
        35                  40                  45

Asp Thr Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Thr Glu

```
                65                  70                  75                  80
Asp Ala Ala Thr Tyr Tyr Cys Gln Gln Trp Thr Thr Asn Pro Leu Thr
                        85                  90                  95

Phe Gly Ala Gly Thr Arg Val Glu Leu Lys
            100                 105

<210> SEQ ID NO 20
<211> LENGTH: 357
<212> TYPE: DNA
<213> ORGANISM: Homo sapiens
<220> FEATURE:
<221> NAME/KEY: CDS
<222> LOCATION: (1)..(357)
<220> FEATURE:
<221> NAME/KEY: misc_feature
<222> LOCATION: (1)..(357)
<223> OTHER INFORMATION: TMC-2206 VH

<400> SEQUENCE: 20 cag gtg cag ttg aag gag tca gga cct ggc ctg gtg gcg ccc tca cag        48
Gln Val Gln Leu Lys Glu Ser Gly Pro Gly Leu Val Ala Pro Ser Gln
1               5                   10                  15 agc ctg tcc atc act tgt act gtc tct gga ttt tca tta acc aac tat        96
Ser Leu Ser Ile Thr Cys Thr Val Ser Gly Phe Ser Leu Thr Asn Tyr
                20                  25                  30 ggt att cac tgg gtt cgc cag cct cca gga aag ggt ctg gag tgg ctg       144
Gly Ile His Trp Val Arg Gln Pro Pro Gly Lys Gly Leu Glu Trp Leu
            35                  40                  45 gga gtg ata tgg gct cgt gga ttc aca aat tat aat tcg gct ctc atg       192
Gly Val Ile Trp Ala Arg Gly Phe Thr Asn Tyr Asn Ser Ala Leu Met
        50                  55                  60 tcc aga ctg atc atc aca aaa gac aat tcc cag agt caa gtc ttc tta       240
Ser Arg Leu Ile Ile Thr Lys Asp Asn Ser Gln Ser Gln Val Phe Leu
65                  70                  75                  80 aaa atg aac agt cta caa cct gat gac tca gcc act tac ttc tgt gcc       288
Lys Met Asn Ser Leu Gln Pro Asp Asp Ser Ala Thr Tyr Phe Cys Ala
                85                  90                  95 aga gcg aac gac ggg gtc tat tat gct atg gac tac tgg ggt cag gga       336
Arg Ala Asn Asp Gly Val Tyr Tyr Ala Met Asp Tyr Trp Gly Gln Gly
            100                 105                 110 acc tca gtc acc gtc tcc tca                                           357
Thr Ser Val Thr Val Ser Ser
        115

<210> SEQ ID NO 21
<211> LENGTH: 119
<212> TYPE: PRT
<213> ORGANISM: Homo sapiens

<400> SEQUENCE: 21

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
                20                  25                  30

Gly Ile His Trp Val Arg Gln Pro Pro Gly Lys Gly Leu Glu Trp Leu
            35                  40                  45

Gly Val Ile Trp Ala Arg Gly Phe Thr Asn Tyr Asn Ser Ala Leu Met
        50                  55                  60

Ser Arg Leu Ile Ile Thr Lys Asp Asn Ser Gln Ser Gln Val Phe Leu
65                  70                  75                  80

Lys Met Asn Ser Leu Gln Pro Asp Asp Ser Ala Thr Tyr Phe Cys Ala
                85                  90                  95
```

Arg Ala Asn Asp Gly Val Tyr Tyr Ala Met Asp Tyr Trp Gly Gln Gly
            100                 105                 110

Thr Ser Val Thr Val Ser Ser
        115

<210> SEQ ID NO 22
<211> LENGTH: 31
<212> TYPE: DNA
<213> ORGANISM: Homo Sapiens
<220> FEATURE:
<221> NAME/KEY: misc_feature
<223> OTHER INFORMATION: TMC-2206-r5' [forward primer]

<400> SEQUENCE: 22
cccgaattca caggtgcagt tgaaggagtc a                              31

<210> SEQ ID NO 23
<211> LENGTH: 35
<212> TYPE: DNA
<213> ORGANISM: Homo Sapiens
<220> FEATURE:
<221> NAME/KEY: misc_feature
<223> OTHER INFORMATION: TMC-2206-r3' [reverse primer]

<400> SEQUENCE: 23
cgggatcctt aggatcattt accaggagag tggga                          35

<210> SEQ ID NO 24
<211> LENGTH: 31
<212> TYPE: DNA
<213> ORGANISM: Homo Sapiens
<220> FEATURE:
<221> NAME/KEY: misc_feature
<223> OTHER INFORMATION: TMC-2206-k5' [forward primer]

<400> SEQUENCE: 24
cccgaattca caatttgttc tcacccagtc t                              31

<210> SEQ ID NO 25
<211> LENGTH: 35
<212> TYPE: DNA
<213> ORGANISM: Homo Sapiens
<220> FEATURE:
<221> NAME/KEY: misc_feature
<223> OTHER INFORMATION: TMC-2206-k3' [reverse primer]

<400> SEQUENCE: 25
cgggatcctt atctctaaca ctcattcctg ttgaa                          35

<210> SEQ ID NO 26
<211> LENGTH: 22
<212> TYPE: PRT
<213> ORGANISM: Homo Sapiens
<220> FEATURE:
<221> NAME/KEY: MISC_FEATURE
<223> OTHER INFORMATION: Igkappa (Igk) leader sequence

<400> SEQUENCE: 26

Met Glu Thr Asp Thr Leu Leu Leu Trp Val Leu Leu Leu Trp Val Pro
1               5                   10                  15

Gly Gly Ser Thr Gly Asp
            20

<210> SEQ ID NO 27
<211> LENGTH: 76
<212> TYPE: DNA

```
<213> ORGANISM: Homo Sapiens
<220> FEATURE:
<221> NAME/KEY: misc_feature
<223> OTHER INFORMATION: Igkappa-S Oligonucleotides [Primer]

<400> SEQUENCE: 27
tcgagccacc atggagacag acacactcct gctatgggta ctgctgctct gggttccagg    60
ttccactgga gacgcg                                                    76

<210> SEQ ID NO 28
<211> LENGTH: 76
<212> TYPE: DNA
<213> ORGANISM: Homo Sapiens
<220> FEATURE:
<221> NAME/KEY: misc_feature
<223> OTHER INFORMATION: Igkappa-AS oligonucleotides [Primer]

<400> SEQUENCE: 28
aattcgcgtc tccagtggaa cctggaaccc agagcagcag tacccatagc aggagtgtgt    60
ctgtctccat ggtggc                                                    76

<210> SEQ ID NO 29
<211> LENGTH: 33
<212> TYPE: DNA
<213> ORGANISM: Homo Sapiens
<220> FEATURE:
<221> NAME/KEY: misc_feature
<223> OTHER INFORMATION: TMC2206VH-hIgG1/4Fc-SalI

<400> SEQUENCE: 29
cttggtcgac gctgaggaga cggtgactga ggt                                 33

<210> SEQ ID NO 30
<211> LENGTH: 30
<212> TYPE: DNA
<213> ORGANISM: Homo Sapiens
<220> FEATURE:
<221> NAME/KEY: misc_feature
<223> OTHER INFORMATION: hIgG1/4Fc-SalI-F [forward primer]

<400> SEQUENCE: 30
tcagcgtcga ccaagggccc atcsgtcttc                                     30

<210> SEQ ID NO 31
<211> LENGTH: 48
<212> TYPE: DNA
<213> ORGANISM: Homo Sapiens
<220> FEATURE:
<221> NAME/KEY: misc_feature
<223> OTHER INFORMATION: hIgG1/4Fc-NotI-R [reverse primer]

<400> SEQUENCE: 31
aagggaagcg gccgcttatc atttacccyg agacagggag aggctctt                 48

<210> SEQ ID NO 32
<211> LENGTH: 39
<212> TYPE: DNA
<213> ORGANISM: Homo Sapiens
<220> FEATURE:
<221> NAME/KEY: misc_feature
<223> OTHER INFORMATION: TMC2206VL-hKc-SalI [reverse primer]

<400> SEQUENCE: 32
tcgtttgatg tcgaccttgg tcccagcacc gaacgtgag                           39

<210> SEQ ID NO 33
```

```
<211> LENGTH: 35
<212> TYPE: DNA
<213> ORGANISM: Homo Sapiens
<220> FEATURE:
<221> NAME/KEY: misc_feature
<223> OTHER INFORMATION: hKc-SalI-F [forward primer]

<400> SEQUENCE: 33
accaaggtcg acatcaaacg aactgtggct gcacc                              35

<210> SEQ ID NO 34
<211> LENGTH: 45
<212> TYPE: DNA
<213> ORGANISM: Homo Sapiens
<220> FEATURE:
<221> NAME/KEY: misc_feature
<223> OTHER INFORMATION: hKc-NotI-R [reverse primer]

<400> SEQUENCE: 34
aagggaagcg gccgcttatc arcactctcc cctgttgaag ctctt                   45

<210> SEQ ID NO 35
<211> LENGTH: 29
<212> TYPE: DNA
<213> ORGANISM: Homo Sapiens
<220> FEATURE:
<221> NAME/KEY: misc_feature
<223> OTHER INFORMATION: TMC-2206VLwt-hKc-F [forward primer]

<400> SEQUENCE: 35
agggtggagc tgaaacgaac tgtggctgc                                     29

<210> SEQ ID NO 36
<211> LENGTH: 24
<212> TYPE: DNA
<213> ORGANISM: Homo Sapiens
<220> FEATURE:
<221> NAME/KEY: misc_feature
<223> OTHER INFORMATION: TMC-2206VLwt-hKc-R [reverse primer]

<400> SEQUENCE: 36
tcgtttcagc tccaccctgg tccc                                          24

<210> SEQ ID NO 37
<211> LENGTH: 107
<212> TYPE: PRT
<213> ORGANISM: Homo Sapiens
<220> FEATURE:
<221> NAME/KEY: MISC_FEATURE
<223> OTHER INFORMATION: A14 VL germline protein

<400> SEQUENCE: 37

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Trp Thr Thr Asn Pro Leu
                85                  90                  95

Thr Phe Gly Gln Gly Thr Lys Val Glu Ile Lys
            100                 105
```

<210> SEQ ID NO 38
<211> LENGTH: 10
<212> TYPE: PRT
<213> ORGANISM: Homo Sapiens
<220> FEATURE:
<221> NAME/KEY: MISC_FEATURE
<223> OTHER INFORMATION: FW 4 of mature kappa light chain

<400> SEQUENCE: 38

Phe Gly Gln Gly Thr Lys Val Glu Ile Lys
1               5                   10

<210> SEQ ID NO 39
<211> LENGTH: 121
<212> TYPE: PRT
<213> ORGANISM: Homo Sapiens
<220> FEATURE:
<221> NAME/KEY: MISC_FEATURE
<223> OTHER INFORMATION: 4-59 VH germline protein

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Asn Ser Ser Ser Trp Tyr Gly Arg Tyr Phe Asp Tyr Trp Gly
            100                 105                 110

Gln Gly Thr Leu Val Thr Val Ser Ser
        115                 120

<210> SEQ ID NO 40
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH1.0

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

```
Arg Ala Asn Asp Gly Val Tyr Tyr Ala Met Asp Tyr Trp Gly Gln Gly
            100                 105                 110

Thr Leu Val Thr Val Ser Ser
            115
```

<210> SEQ ID NO 41
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL1.0

<400> SEQUENCE: 41

```
Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Leu Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105
```

<210> SEQ ID NO 42
<211> LENGTH: 48
<212> TYPE: DNA
<213> ORGANISM: Homo Sapiens
<220> FEATURE:
<221> NAME/KEY: misc_feature
<223> OTHER INFORMATION: hVH3.0-F [forward primer]

<400> SEQUENCE: 42
agcgtggaca ccagcaagaa ccagttcagc ctgaagctga gcagcgtg                48

<210> SEQ ID NO 43
<211> LENGTH: 51
<212> TYPE: DNA
<213> ORGANISM: Homo Sapiens
<220> FEATURE:
<221> NAME/KEY: misc_feature
<223> OTHER INFORMATION: hVH3.0-R [reverse primer]

<400> SEQUENCE: 43
gttcttgctg gtgtccacgc tgatggtcac gcgggacatg agagcgctgt t            51

<210> SEQ ID NO 44
<211> LENGTH: 48
<212> TYPE: DNA
<213> ORGANISM: Homo Sapiens
<220> FEATURE:
<221> NAME/KEY: misc_feature
<223> OTHER INFORMATION: hVH4.0-F [forward primer]

<400> SEQUENCE: 44
cctccaggca agggcctgga gtggatcggc gtgatatggg ctcgcggc                48

<210> SEQ ID NO 45
<211> LENGTH: 51

<212> TYPE: DNA
<213> ORGANISM: Homo Sapiens
<220> FEATURE:
<221> NAME/KEY: misc_feature
<223> OTHER INFORMATION: hVH4.0-R [reverse primer]

<400> SEQUENCE: 45
ctccaggccc ttgcctggag gctggcgtat ccagtggatg ccatagttgg t          51

<210> SEQ ID NO 46
<211> LENGTH: 33
<212> TYPE: DNA
<213> ORGANISM: Homo Sapiens
<220> FEATURE:
<221> NAME/KEY: misc_feature
<223> OTHER INFORMATION: hVL3.0-F [forward primer]

<400> SEQUENCE: 46
cccaagctcc tgatctatga cacttccaag ctg                              33

<210> SEQ ID NO 47
<211> LENGTH: 42
<212> TYPE: DNA
<213> ORGANISM: Homo Sapiens
<220> FEATURE:
<221> NAME/KEY: misc_feature
<223> OTHER INFORMATION: hVL3.0-R [reverse primer]

<400> SEQUENCE: 47
agtgtcatag atcaggagct tgggggcctg gtcgggcttc tg                    42

<210> SEQ ID NO 48
<211> LENGTH: 45
<212> TYPE: DNA
<213> ORGANISM: Homo Sapiens
<220> FEATURE:
<221> NAME/KEY: misc_feature
<223> OTHER INFORMATION: hVL4.0-F [forward primer]

<400> SEQUENCE: 48
gacgcgaatt cagacgtggt gatgacccag tctccagcat cctg                  45

<210> SEQ ID NO 49
<211> LENGTH: 24
<212> TYPE: DNA
<213> ORGANISM: Homo Sapiens
<220> FEATURE:
<221> NAME/KEY: misc_feature
<223> OTHER INFORMATION: hVH2.0-F [forward primer]

<400> SEQUENCE: 49
gtgaccatca gcaaggacaa cagc                                        24

<210> SEQ ID NO 50
<211> LENGTH: 45
<212> TYPE: DNA
<213> ORGANISM: Homo Sapiens
<220> FEATURE:
<221> NAME/KEY: misc_feature
<223> OTHER INFORMATION: hVH2.0-R [reverse primer]

<400> SEQUENCE: 50
gctgttgtcc ttgctgatgg tcacgcggga catgagagcg ctgtt                 45

<210> SEQ ID NO 51
<211> LENGTH: 27
<212> TYPE: DNA
<213> ORGANISM: Homo Sapiens

```
<220> FEATURE:
<221> NAME/KEY: misc_feature
<223> OTHER INFORMATION: hVH5.0-F [forward primer]

<400> SEQUENCE: 51
atcggcgtga tatgggctcg cggcttc                                              27

<210> SEQ ID NO 52
<211> LENGTH: 45
<212> TYPE: DNA
<213> ORGANISM: Homo Sapiens
<220> FEATURE:
<221> NAME/KEY: misc_feature
<223> OTHER INFORMATION: hVH5.0-R [reverse primer]

<400> SEQUENCE: 52
gccgcgagcc catatcacgc cgatccactc caggcccttg cctgg                          45

<210> SEQ ID NO 53
<211> LENGTH: 24
<212> TYPE: DNA
<213> ORGANISM: Homo Sapiens
<220> FEATURE:
<221> NAME/KEY: misc_feature
<223> OTHER INFORMATION: hVH6.0-F [forward primer]

<400> SEQUENCE: 53
atatgggctc gcggcttcac aaac                                                 24

<210> SEQ ID NO 54
<211> LENGTH: 24
<212> TYPE: DNA
<213> ORGANISM: Homo Sapiens
<220> FEATURE:
<221> NAME/KEY: misc_feature
<223> OTHER INFORMATION: hVH6.0-R [reverse primer]

<400> SEQUENCE: 54
gtttgtgaag ccgcgagccc atat                                                 24

<210> SEQ ID NO 55
<211> LENGTH: 45
<212> TYPE: DNA
<213> ORGANISM: Homo Sapiens
<220> FEATURE:
<221> NAME/KEY: misc_feature
<223> OTHER INFORMATION: hVH7.0-F [forward primer]

<400> SEQUENCE: 55
gccgcggaca ccgccgtgta ctactgcgcc agagccaacg acggg                          45

<210> SEQ ID NO 56
<211> LENGTH: 27
<212> TYPE: DNA
<213> ORGANISM: Homo Sapiens
<220> FEATURE:
<221> NAME/KEY: misc_feature
<223> OTHER INFORMATION: hVH7.0-R [reverse primer]

<400> SEQUENCE: 56
gtagtacacg gcggtgtccg cggcggt                                              27

<210> SEQ ID NO 57
<211> LENGTH: 27
<212> TYPE: DNA
<213> ORGANISM: Homo Sapiens
<220> FEATURE:
<221> NAME/KEY: misc_feature
```

<223> OTHER INFORMATION: hVH8.0-F [forward primer]

<400> SEQUENCE: 57
atatccaact atggcatcca ctgggtt         27

<210> SEQ ID NO 58
<211> LENGTH: 48
<212> TYPE: DNA
<213> ORGANISM: Homo Sapiens
<220> FEATURE:
<221> NAME/KEY: misc_feature
<223> OTHER INFORMATION: hVH8.0-R [reverse primer]

<400> SEQUENCE: 58
ccagtggatg ccatagttgg atatgctaaa tccagagacg gtacaggt         48

<210> SEQ ID NO 59
<211> LENGTH: 45
<212> TYPE: DNA
<213> ORGANISM: Homo Sapiens
<220> FEATURE:
<221> NAME/KEY: misc_feature
<223> OTHER INFORMATION: hVL2.0-R [reverse primer]

<400> SEQUENCE: 59
cagcttggaa gtgtcataga tcaatttctt gggggcctgg tcggg         45

<210> SEQ ID NO 60
<211> LENGTH: 45
<212> TYPE: DNA
<213> ORGANISM: Homo Sapiens
<220> FEATURE:
<221> NAME/KEY: misc_feature
<223> OTHER INFORMATION: hVL5.0-F [forward primer]

<400> SEQUENCE: 60
gacgcgaatt cagacttcgt gctgacccag tctccagcat cctg         45

<210> SEQ ID NO 61
<211> LENGTH: 45
<212> TYPE: DNA
<213> ORGANISM: Homo Sapiens
<220> FEATURE:
<221> NAME/KEY: misc_feature
<223> OTHER INFORMATION: hVL6.0-F [forward primer]

<400> SEQUENCE: 61
gacgcgaatt cacagttcgt gatgacccag tctccagcat cctg         45

<210> SEQ ID NO 62
<211> LENGTH: 45
<212> TYPE: DNA
<213> ORGANISM: Homo Sapiens
<220> FEATURE:
<221> NAME/KEY: misc_feature
<223> OTHER INFORMATION: hVL7.0-F [forward primer]

<400> SEQUENCE: 62
gacgcgaatt cagacttcgt gatgacccag tctccagcat cctg         45

<210> SEQ ID NO 63
<211> LENGTH: 27
<212> TYPE: DNA
<213> ORGANISM: Homo Sapiens
<220> FEATURE:
<221> NAME/KEY: misc_feature
<223> OTHER INFORMATION: hVL8.0-F [forward primer]

<400> SEQUENCE: 63
ttcaccttca ccatcagcag cctggag                                             27

<210> SEQ ID NO 64
<211> LENGTH: 48
<212> TYPE: DNA
<213> ORGANISM: Homo Sapiens
<220> FEATURE:
<221> NAME/KEY: misc_feature
<223> OTHER INFORMATION: hVL8.0-R [reverse primer]

<400> SEQUENCE: 64
ctccaggctg ctgatggtga aggtgaagtc ggtgccgctg ccgctgcc                      48

<210> SEQ ID NO 65
<211> LENGTH: 28
<212> TYPE: DNA
<213> ORGANISM: Homo Sapiens
<220> FEATURE:
<221> NAME/KEY: misc_feature
<223> OTHER INFORMATION: hLCQ3-F [forward primer]

<400> SEQUENCE: 65
ccaatcaagc gtgaactaca ttcactgg                                            28

<210> SEQ ID NO 66
<211> LENGTH: 48
<212> TYPE: DNA
<213> ORGANISM: Homo Sapiens
<220> FEATURE:
<221> NAME/KEY: misc_feature
<223> OTHER INFORMATION: hLCQ3-R [reverse primer]

<400> SEQUENCE: 66
ccagtgaatg tagttcacgc ttgattgggc gctgcaggtg atggtcac                      48

<210> SEQ ID NO 67
<211> LENGTH: 23
<212> TYPE: DNA
<213> ORGANISM: Homo Sapiens
<220> FEATURE:
<221> NAME/KEY: misc_feature
<223> OTHER INFORMATION: Igk-For [forward primer]

<400> SEQUENCE: 67
actcctgcta tgggtactgc tgc                                                 23

<210> SEQ ID NO 68
<211> LENGTH: 22
<212> TYPE: DNA
<213> ORGANISM: Homo Sapiens
<220> FEATURE:
<221> NAME/KEY: misc_feature
<223> OTHER INFORMATION: hIgG1Fc-CH1-R [reverse primer]

<400> SEQUENCE: 68
gaagtagtcc ttgaccaggc ag                                                  22

<210> SEQ ID NO 69
<211> LENGTH: 22
<212> TYPE: DNA
<213> ORGANISM: Homo Sapiens
<220> FEATURE:
<221> NAME/KEY: misc_feature
<223> OTHER INFORMATION: CI-neo-msc3' [Primer]

<400> SEQUENCE: 69

```
tttcactgca ttctagttgt gg                                              22
```

<210> SEQ ID NO 70
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH2.0

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 71
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH3.0

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 72
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH4.0

```
<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 73
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH5.0

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 74
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH6.0

<400> SEQUENCE: 74

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
```

-continued

```
                35                  40                  45
Gly Val Ile Trp Ala Arg Gly Phe Thr Asn Tyr Asn Ser Ala Leu Met
 50                  55                  60

Ser Arg Val Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Phe Cys Ala
                 85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 75
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH7.0

<400> SEQUENCE: 75

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Asn Tyr
                 20                  25                  30

Gly Ile His Trp Val Arg Gln Pro Pro Gly Lys Gly Leu Glu Trp Leu
                 35                  40                  45

Gly Val Ile Trp Ala Arg Gly Phe Thr Asn Tyr Asn Ser Ala Leu Met
 50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Asn Asp Gly Val Tyr Tyr Ala Met Asp Tyr Trp Gly Gln Gly
                100                 105                 110

Thr Leu Val Thr Val Ser Ser
        115

<210> SEQ ID NO 76
<211> LENGTH: 119
<212> TYPE: PRT
<213> ORGANISM: Homo sapiens
<220> FEATURE:
<221> NAME/KEY: MISC_FEATURE
<223> OTHER INFORMATION: hVH8.0

<400> SEQUENCE: 76

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Ile Ser Asn Tyr
                 20                  25                  30

Gly Ile His Trp Val Arg Gln Pro Pro Gly Lys Gly Leu Glu Trp Leu
                 35                  40                  45

Gly Val Ile Trp Ala Arg Gly Phe Thr Asn Tyr Asn Ser Ala Leu Met
 50                  55                  60

Ser Arg Leu Thr Ile Ser Lys Asp Asn Ser Lys Asn Gln Phe Ser Leu
 65                  70                  75                  80

Lys Leu Ser Ser Val Thr Ala Ala Asp Thr Ala Val Tyr Phe Cys Ala
                 85                  90                  95
```

```
Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 77
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH9.0 Position 48 can be Leucine or Isoleucine

<400> SEQUENCE: 77

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Val Asp Asn Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 78
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH10.0

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 79
<211> LENGTH: 119
```

```
<212> TYPE: PRT
<213> ORGANISM: Homo Sapiens
<220> FEATURE:
<221> NAME/KEY: MISC_FEATURE
<223> OTHER INFORMATION: hVH11.0  Position 48 can be Leucine or
      Isoleucine

<400> SEQUENCE: 79
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

```
<210> SEQ ID NO 80
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL2.0

<400> SEQUENCE: 80
```

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

```
<210> SEQ ID NO 81
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL3.0

<400> SEQUENCE: 81
```

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile

```
                20                  25                  30
His Trp Tyr Gln Gln Lys Pro Asp Gln Ala Pro Lys Leu Leu Ile Tyr
             35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
                100                 105

<210> SEQ ID NO 82
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL4.0

<400> SEQUENCE: 82

Asp Val Val Met Thr Gln Ser Pro Ala Phe Leu Ser Val Thr Pro Gly
 1               5                  10                  15

Glu Lys Val Thr Ile Thr Cys Ser Ala Asn Ser Ser Val Asn Tyr Ile
                 20                  25                  30

His Trp Tyr Gln Gln Lys Pro Asp Gln Ala Pro Lys Lys Trp Ile Tyr
             35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
                100                 105

<210> SEQ ID NO 83
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL5.0

<400> SEQUENCE: 83

Asp Phe Val Leu Thr Gln Ser Pro Ala Phe Leu Ser Val Thr Pro Gly
 1               5                  10                  15

Glu Lys Val Thr Ile Thr Cys Ser Ala Asn Ser Ser Val Asn Tyr Ile
                 20                  25                  30

His Trp Tyr Gln Gln Lys Pro Asp Gln Ala Pro Lys Lys Trp Ile Tyr
             35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                 85                  90                  95

Phe Gly Gln Gly Thr Lys Val Glu Ile Lys
                100                 105
```

<210> SEQ ID NO 84
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL6.0

<400> SEQUENCE: 84

Gln Phe Val Met Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 85
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL7.0

<400> SEQUENCE: 85

Asp Phe Val Met Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 86
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL8.0

<400> SEQUENCE: 86

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile

```
                20                  25                  30
His Trp Tyr Gln Gln Lys Pro Asp Gln Ala Pro Lys Lys Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 87
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL9.0

<400> SEQUENCE: 87

Gln Phe Val Leu Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Lys
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 88
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL10.0

<400> SEQUENCE: 88

Asp Phe Val Met Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105
```

<210> SEQ ID NO 89
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL11.0

<400> SEQUENCE: 89

Asp Phe Val Met Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 90
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL1.0Q

<400> SEQUENCE: 90

Gln Phe Val Leu Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 91
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL10.0Q

<400> SEQUENCE: 91

Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile

```
                   20                  25                  30

His Trp Tyr Gln Gln Lys Pro Asp Gln Ala Pro Lys Lys Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 92
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL12.0Q

<400> SEQUENCE: 92

Asp Phe Val Met Thr Gln Ser Pro Ala Phe Leu Ser Val Thr Pro Gly
 1               5                  10                  15

Glu Lys Val Thr Ile Thr Cys Ser Ala Gln Ser Ser Val Asn Tyr Ile
                20                  25                  30

His Trp Tyr Gln Gln Lys Pro Asp Gln Ala Pro Lys Lys Leu Ile Tyr
            35                  40                  45

Asp Thr Ser Lys Leu Ala Ser Gly Val Pro Ser Arg Phe Ser Gly Ser
 50                  55                  60

Gly Ser Gly Thr Asp Phe Thr Phe Thr Ile Ser Ser Leu Glu Ala Glu
 65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 93
<211> LENGTH: 222
<212> TYPE: PRT
<213> ORGANISM: Rattus rattus
<220> FEATURE:
<221> NAME/KEY: MISC_FEATURE
<223> OTHER INFORMATION: Rat alpha2 integrin I domain protein

<400> SEQUENCE: 93

Ser Pro Asp Phe Gln Ser Leu Thr Ser Phe Ser Pro Ala Val Gln Asp
 1               5                  10                  15

Val Val Val Val Cys Asp Glu Ser Asn Ser Ile Tyr Pro Trp Glu Ala
                20                  25                  30

Val Lys Asn Phe Leu Glu Lys Phe Val Gln Gly Leu Asp Ile Gly Pro
            35                  40                  45

Lys Lys Thr Gln Val Ala Leu Ile Gln Tyr Ala Asn Asp Pro Arg Val
 50                  55                  60

Val Phe Asn Leu Thr Thr Tyr Lys Asn Lys Glu Asp Met Val Gln Ala
 65                  70                  75                  80

Thr Ser Glu Thr Arg Gln Tyr Gly Gly Asp Leu Thr Asn Thr Phe Lys
                85                  90                  95

Ala Ile Gln Phe Ala Arg Asp Ile Ala Tyr Leu Pro Glu Ser Gly Gly
            100                 105                 110
```

Arg Pro Gly Ala Thr Lys Val Met Val Val Thr Asp Gly Glu Ser
            115                 120                 125

His Asp Gly Ser Lys Leu Gln Thr Val Ile Gln Gln Cys Asn Asp Asp
130                 135                 140

Glu Ile Leu Arg Phe Gly Ile Ala Val Leu Gly Tyr Leu Asn Arg Asn
145                 150                 155                 160

Ala Leu Asp Thr Lys Asn Leu Ile Lys Glu Ile Lys Ala Ile Ala Ser
                165                 170                 175

Thr Pro Thr Glu Arg Tyr Phe Phe Asn Val Ala Asp Glu Ala Ala Leu
            180                 185                 190

Leu Glu Lys Ala Gly Thr Leu Gly Glu His Ile Phe Ser Ile Glu Gly
        195                 200                 205

Thr Val Gln Gly Gly Asp Asn Phe Gln Met Glu Met Ala Gln
    210                 215                 220

<210> SEQ ID NO 94
<211> LENGTH: 228
<212> TYPE: PRT
<213> ORGANISM: Mus musculus
<220> FEATURE:
<221> NAME/KEY: MISC_FEATURE
<223> OTHER INFORMATION: Mouse alpha2 integrin I domain protein

<400> SEQUENCE: 94

Ser Pro Asp Phe Gln Phe Leu Thr Ser Phe Ser Pro Ala Val Gln Ala
1               5                   10                  15

Cys Pro Ser Leu Val Asp Val Val Val Cys Asp Glu Ser Asn Ser
            20                  25                  30

Ile Tyr Pro Trp Glu Ala Val Lys Asn Phe Leu Val Lys Phe Val Thr
        35                  40                  45

Gly Leu Asp Ile Gly Pro Lys Lys Thr Gln Val Ala Leu Ile Gln Tyr
    50                  55                  60

Ala Asn Glu Pro Arg Ile Ile Phe Asn Leu Asn Asp Phe Glu Thr Lys
65                  70                  75                  80

Glu Asp Met Val Gln Ala Thr Ser Glu Thr Arg Gln His Gly Gly Asp
                85                  90                  95

Leu Thr Asn Thr Phe Arg Ala Ile Glu Phe Ala Arg Asp Tyr Ala Tyr
            100                 105                 110

Ser Gln Thr Ser Gly Gly Arg Pro Gly Ala Thr Lys Val Met Val Val
        115                 120                 125

Val Thr Asp Gly Glu Ser His Asp Gly Ser Lys Leu Lys Thr Val Ile
    130                 135                 140

Gln Gln Cys Asn Asp Asp Glu Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175

Ile Lys Ala Ile Ala Ser Thr Pro Thr Glu Arg Tyr Phe Phe Asn Val
            180                 185                 190

Ser Asp Glu Ala Ala Leu Leu Glu Lys Ala Gly Thr Leu Gly Glu Gln
        195                 200                 205

Ile Phe Ser Ile Glu Gly Thr Val Gln Gly Gly Asp Asn Phe Gln Met
    210                 215                 220

Glu Met Ser Gln
225

<210> SEQ ID NO 95

```
<211> LENGTH: 26
<212> TYPE: DNA
<213> ORGANISM: Homo Sapiens
<220> FEATURE:
<221> NAME/KEY: misc_feature
<223> OTHER INFORMATION: Kappa-F

<400> SEQUENCE: 95
cgaactgtgg ctgcaccatc tgtctt                                          26

<210> SEQ ID NO 96
<211> LENGTH: 41
<212> TYPE: DNA
<213> ORGANISM: Homo Sapiens
<220> FEATURE:
<221> NAME/KEY: misc_feature
<223> OTHER INFORMATION: Kappa-BamHI-R

<400> SEQUENCE: 96
aattcggatc cttactaaca ctctcccctg ttgaagctct t                         41

<210> SEQ ID NO 97
<211> LENGTH: 40
<212> TYPE: DNA
<213> ORGANISM: Homo Sapiens
<220> FEATURE:
<221> NAME/KEY: misc_feature
<223> OTHER INFORMATION: VH12.0-(K71V)-F

<400> SEQUENCE: 97
gcctgaccat cagcgtggac aacagcaaga accaggtgag                           40

<210> SEQ ID NO 98
<211> LENGTH: 40
<212> TYPE: DNA
<213> ORGANISM: Homo Sapiens
<220> FEATURE:
<221> NAME/KEY: misc_feature
<223> OTHER INFORMATION: VH12.0(K71V)-R

<400> SEQUENCE: 98
ctcacctggt tcttgctgtt gtccacgctg atggtcaggc                           40

<210> SEQ ID NO 99
<211> LENGTH: 40
<212> TYPE: DNA
<213> ORGANISM: Homo Sapiens
<220> FEATURE:
<221> NAME/KEY: misc_feature
<223> OTHER INFORMATION: VH13.0-(N73T)-F

<400> SEQUENCE: 99
ctgaccatca gcaaggacac cagcaagaac caggtgagcc                           40

<210> SEQ ID NO 100
<211> LENGTH: 40
<212> TYPE: DNA
<213> ORGANISM: Homo Sapiens
<220> FEATURE:
<221> NAME/KEY: misc_feature
<223> OTHER INFORMATION: VH13.0-(N73T)R

<400> SEQUENCE: 100
ggctcacctg gttcttgctg gtgtccttgc tgatggtcag                           40

<210> SEQ ID NO 101
<211> LENGTH: 41
<212> TYPE: DNA
```

```
<213> ORGANISM: Homo Sapiens
<220> FEATURE:
<221> NAME/KEY: misc_feature
<223> OTHER INFORMATION: VH14.0-(V78F)-F

<400> SEQUENCE: 101
gcaaggacaa cagcaagaac cagtttagcc tgaagctgag c                  41

<210> SEQ ID NO 102
<211> LENGTH: 41
<212> TYPE: DNA
<213> ORGANISM: Homo Sapiens
<220> FEATURE:
<221> NAME/KEY: misc_feature
<223> OTHER INFORMATION: VH14.0 (V78F)-R

<400> SEQUENCE: 102
gctcagcttc aggctaaact ggttcttgct gttgtccttg c                  41

<210> SEQ ID NO 103
<211> LENGTH: 648
<212> TYPE: DNA
<213> ORGANISM: Macaca fascicularis
<220> FEATURE:
<221> NAME/KEY: misc_feature
<223> OTHER INFORMATION: Cynomolgus alpha2 I domain

<400> SEQUENCE: 103
agtcctgatt ttcagctctc agccagcttc tcacctgcaa ctcagccctg cccttccctc    60
atagatgttg tggttgtgtg tgatgaatca aatagtattt atccttggga tgcagtagac   120
aattttttgg aaaaatttgt acaaggcctg gatataggcc ccacaaagac acaggtgggg   180
ttaattcagt atgccaataa tccaagagtt gtgtttaact tgaacacata taaaaccaaa   240
gaagaaatga ttgtagcaac atcccagaca tcccaatatg gtggggacct cacaaacaca   300
ttcggagcaa ttcaatatgc aagaaaatat gcctattcag cagcttctgg tgggcgacga   360
agtgctacga aagtaatggt agttgtaact gacggtgaat cacatgatgg ttcaatgttg   420
aaagctgtga ttgatcaatg caaccatgac aatatactga ggtttggcat agcagttctt   480
gggtacttaa acagaaacgc ccttgatact aaaaatttaa taaagaaat aaaagcgatc   540
gctagtattc aacagaaaag atacttttc aatgtgtctg atgaagcagc tctactagaa   600
aaggctggga cattaggaga acaaattttc agcattgaag gtactgtt             648

<210> SEQ ID NO 104
<211> LENGTH: 648
<212> TYPE: DNA
<213> ORGANISM: Macaca mulatta
<220> FEATURE:
<221> NAME/KEY: misc_feature
<223> OTHER INFORMATION: Rhesus alpha2 I domain

<400> SEQUENCE: 104
agtcctgatt ttcagctctc agccagcttc tcacctgcaa ctcagccctg cccttccctc    60
atagatgttg tggttgtgtg tgatgaatca aatagtattt atccttggga tgcagtaaag   120
aattttttgg aaaaatttgt acaaggcctg gatataggcc ccacaaagac acaggtgggg   180
ttaattcagt atgccaataa tccaagagtt gtgtttaact tgaacacata taaaaccaaa   240
gaagaaatga ttgtagcaac atcccagaca tcccaatatg gtggggacct cacaaacaca   300
ttcggagcaa ttcaatatgc aagaaaatat gcctattcag cagcttctgg tgggcgacga   360
agtgctacga aagtaatggt agttgtaact gacggtgaat cacatgatgg ttcaatgttg   420
```

```
aaagctgtga ttgatcaatg caaccatgac aatatactga ggtttggcat agcagttctt    480
gggtacttaa acagaaacgc ccttgatact aaaaatttaa taaaagaaat aaaagcgatc    540
gctagtattc caacagaaag atacttttc aatgtgtctg atgaagcagc tctactagaa     600
aaggctggga cattaggaga acaaattttc agcattgaag gtactgtt                648
```

<210> SEQ ID NO 105
<211> LENGTH: 997
<212> TYPE: DNA
<213> ORGANISM: Homo Sapiens
<220> FEATURE:
<221> NAME/KEY: misc_feature
<223> OTHER INFORMATION: IgG4 constant region
<220> FEATURE:
<221> NAME/KEY: CDS
<222> LOCATION: (1)..(978)

<400> SEQUENCE: 105

```
tcc acc aag ggc cca tcc gtc ttc ccc ctg gcg ccc tgc tcc agg agc     48
Ser Thr Lys Gly Pro Ser Val Phe Pro Leu Ala Pro Cys Ser Arg Ser
1               5                  10                  15 acc tcc gag agc aca gcc gcc ctg ggc tgc ctg gtc aag gac tac ttc     96
Thr Ser Glu Ser Thr Ala Ala Leu Gly Cys Leu Val Lys Asp Tyr Phe
            20                  25                  30 ccc gaa ccg gtg acg gtg tcg tgg aac tca ggc gcc ctg acc agc ggc    144
Pro Glu Pro Val Thr Val Ser Trp Asn Ser Gly Ala Leu Thr Ser Gly
        35                  40                  45 gtg cac acc ttc ccg gct gtc cta cag tcc tca gga ctc tac tcc ctc    192
Val His Thr Phe Pro Ala Val Leu Gln Ser Ser Gly Leu Tyr Ser Leu
    50                  55                  60 agc agc gtg gtg acc gtg ccc tcc agc agc ttg ggc acg aag acc tac    240
Ser Ser Val Val Thr Val Pro Ser Ser Ser Leu Gly Thr Lys Thr Tyr
65                  70                  75                  80 acc tgc aac gta gat cac aag ccc agc aac acc aag gtg gac aag aga    288
Thr Cys Asn Val Asp His Lys Pro Ser Asn Thr Lys Val Asp Lys Arg
                85                  90                  95 gtt gag tcc aaa tat ggt ccc cca tgc cca tca tgc cca gca cct gag    336
Val Glu Ser Lys Tyr Gly Pro Pro Cys Pro Ser Cys Pro Ala Pro Glu
            100                 105                 110 ttc ctg ggg gga cca tca gtc ttc ctg ttc ccc cca aaa ccc aag gac    384
Phe Leu Gly Gly Pro Ser Val Phe Leu Phe Pro Pro Lys Pro Lys Asp
        115                 120                 125 act ctc atg atc tcc cgg acc cct gag gtc acg tgc gtg gtg gtg gac    432
Thr Leu Met Ile Ser Arg Thr Pro Glu Val Thr Cys Val Val Val Asp
    130                 135                 140 gtg agc cag gaa gac ccc gag gtc cag ttc aac tgg tac gtg gat ggc    480
Val Ser Gln Glu Asp Pro Glu Val Gln Phe Asn Trp Tyr Val Asp Gly
145                 150                 155                 160 gtg gag gtg cat aat gcc aag aca aag ccg cgg gag gag cag ttc aac    528
Val Glu Val His Asn Ala Lys Thr Lys Pro Arg Glu Glu Gln Phe Asn
                165                 170                 175 agc acg tac cgt gtg gtc agc gtc ctc acc gtc ctg cac cag gac tgg    576
Ser Thr Tyr Arg Val Val Ser Val Leu Thr Val Leu His Gln Asp Trp
            180                 185                 190 ctg aac ggc aag gag tac aag tgc aag gtc tcc aac aaa ggc ctc ccg    624
Leu Asn Gly Lys Glu Tyr Lys Cys Lys Val Ser Asn Lys Gly Leu Pro
        195                 200                 205 tcc tcc atc gag aaa acc atc tcc aaa gcc aaa ggg cag ccc cga gag    672
Ser Ser Ile Glu Lys Thr Ile Ser Lys Ala Lys Gly Gln Pro Arg Glu
    210                 215                 220 cca cag gtg tac acc ctg ccc cca tcc cag gag gag atg acc aag aac    720
Pro Gln Val Tyr Thr Leu Pro Pro Ser Gln Glu Glu Met Thr Lys Asn
```

```
                225                 230                 235                 240
cag gtc agc ctg acc tgc ctg gtc aaa ggc ttc tac ccc agc gac atc       768
Gln Val Ser Leu Thr Cys Leu Val Lys Gly Phe Tyr Pro Ser Asp Ile
                245                 250                 255 gcc gtg gag tgg gag agc aat ggg cag ccg gag aac aac tac aag acc       816
Ala Val Glu Trp Glu Ser Asn Gly Gln Pro Glu Asn Asn Tyr Lys Thr
            260                 265                 270 acg cct ccc gtg ctg gac tcc gac ggc tcc ttc ttc ctc tac agc agg       864
Thr Pro Pro Val Leu Asp Ser Asp Gly Ser Phe Phe Leu Tyr Ser Arg
        275                 280                 285 cta acc gtg gac aag agc agg tgg cag gag ggg aat gtc ttc tca tgc       912
Leu Thr Val Asp Lys Ser Arg Trp Gln Glu Gly Asn Val Phe Ser Cys
    290                 295                 300 tcc gtg atg cat gag gct ctg cac aac cac tac aca cag aag agc ctc       960
Ser Val Met His Glu Ala Leu His Asn His Tyr Thr Gln Lys Ser Leu
305                 310                 315                 320 tcc ctg tct ctg ggt aaa tgataggatc gcgggccgc                          997
Ser Leu Ser Leu Gly Lys
                325

<210> SEQ ID NO 106
<211> LENGTH: 326
<212> TYPE: PRT
<213> ORGANISM: Homo Sapiens

<400> SEQUENCE: 106

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
```

```
                    245               250                255
Ala Val Glu Trp Glu Ser Asn Gly Gln Pro Glu Asn Asn Tyr Lys Thr
                260               265               270

Thr Pro Pro Val Leu Asp Ser Asp Gly Ser Phe Phe Leu Tyr Ser Arg
            275               280               285

Leu Thr Val Asp Lys Ser Arg Trp Gln Glu Gly Asn Val Phe Ser Cys
        290               295               300

Ser Val Met His Glu Ala Leu His Asn His Tyr Thr Gln Lys Ser Leu
305               310               315               320

Ser Leu Ser Leu Gly Lys
                325

<210> SEQ ID NO 107
<211> LENGTH: 648
<212> TYPE: DNA
<213> ORGANISM: HOMO SAPIENS
<220> FEATURE:
<221> NAME/KEY: misc_feature
<223> OTHER INFORMATION: Human alpha2 I Domain

<400> SEQUENCE: 107
agtcctgatt ttcagctctc agccagcttc tcacctgcaa ctcagccctg cccttccctc    60
atagatgttg tggtggtgtg tgatgaatca aatagtattt atccttggga tgcagtaaag   120 aatttttgg aaaaatttgt acaaggcctg gatataggcc ccacaaagac acaggtgggg    180
ttaattcagt atgccaataa tccaagagtt gtgtttaact tgaacacata taaaaccaaa   240
gaagaaatga ttgtagcaac atcccagaca tcccaatatg gtggggacct cacaaacaca   300
ttcggagcaa ttcaatatgc aagaaaatat gcctattcag cagcttctgg tgggcgacga   360
agtgctacga aagtaatggt agttgtaact gacggtgaat cacatgatgg ttcaatgttg   420
aaagctgtga ttgatcaatg caaccatgac aatatactga ggtttggcat agcagttctt   480
gggtacttaa acagaaacgc ccttgatact aaaaatttaa taaagaaat aaaagcgatc   540 gctagtattc aacagaaag atactttttc aatgtgtctg atgaagcagc tctactagaa   600
aaggctggga cattaggaga acaaattttc agcattgaag gtactgtt                648

<210> SEQ ID NO 108
<211> LENGTH: 106
<212> TYPE: PRT
<213> ORGANISM: Homo Sapiens
<220> FEATURE:
<221> NAME/KEY: MISC_FEATURE
<223> OTHER INFORMATION: hVL12.0

<400> SEQUENCE: 108

Asp Phe Val Met Thr Gln Ser Pro Ala Phe Leu Ser Val Thr Pro Gly
1               5                  10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
```

<210> SEQ ID NO 109
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH12.0  Position 48 can be Leucine or Isoleucine

<400> SEQUENCE: 109

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH13.0

<400> SEQUENCE: 110

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Val Arg Gln Pro Pro Gly Lys Gly Leu Glu Trp Ile
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Homo Sapiens
<220> FEATURE:
<221> NAME/KEY: MISC_FEATURE
<223> OTHER INFORMATION: hVH14.0 Position 48 can be Leucine or
      Isoleucine

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45

Gly Val Ile Trp Ala Arg Gly Phe Thr Asn Tyr Asn Ser Ala Leu Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
        115

<210> SEQ ID NO 112
<211> LENGTH: 10
<212> TYPE: PRT
<213> ORGANISM: Homo Sapiens
<220> FEATURE:
<221> NAME/KEY: MISC_FEATURE
<223> OTHER INFORMATION: LCDR1 [N26Q]

<400> SEQUENCE: 112

Ser Ala Gln Ser Ser Val Asn Tyr Ile His
1               5                   10

<210> SEQ ID NO 113
<211> LENGTH: 681
<212> TYPE: DNA
<213> ORGANISM: Rattus rattus
<220> FEATURE:
<221> NAME/KEY: misc_feature
<223> OTHER INFORMATION: Rat alpha 2 I domain

<400> SEQUENCE: 113
agtccagact ttcagtcgtt gacaagcttc tcacctgcag ttcaagcttg cccttccctc      60
gtagatgtcg tagttgtctg tgatgaatca aacagtattt atccctggga agcagtaaag    120
aattttttgg aaaagtttgt gcaaggcctg gatataggac ctaaaaagac acaggtggcg    180
ttaattcaat atgccaacga cccaagagtt gtctttaact tgaccactta caaaaacaaa    240
gaagatatgg ttcaggccac atccgagacg cgccagtatg gtggggacct cacaaacacc    300
ttcaaggcta tccaatttgc aagagacatt gcttatttac cggagtctgg cgggcgccca    360
ggtgctacaa aagtcatggt agttgtgact gatggggaat cccatgatgg gtcgaagctg    420
caaactgtga tccagcaatg caatgatgac gagatactga ggtttggcat agcggttctt    480
ggatatttaa acagaaatgc tcttgatact aaaaatctaa tcaaagaaat taagcaatc     540
gctagcactc caacggagag gtacttttc aatgtggccg atgaggcggc tcttctggag    600
aaagctggca ctctagggga gcacatattc agcattgaag gcactgttca aggaggagac    660
aacttccaga tggaaatggc a                                              681

<210> SEQ ID NO 114

```
<211> LENGTH: 648
<212> TYPE: DNA
<213> ORGANISM: Mus musculus
<220> FEATURE:
<221> NAME/KEY: misc_feature
<223> OTHER INFORMATION: Mouse alpha 2 I domain clone

<400> SEQUENCE: 114
agtccagact ttcagttctt gaccagcttt tcacctgcag ttcaggcttg cccttccctc      60
gtggatgttg tagttgtatg tgatgaatca aacagtattt atccttggga agcagtaaag     120
aacttttggg taaagtttgt gacaggcctg gatataggac ctaaaaagac acaggtggcg     180
ttaattcaat atgccaatga gccgagaatt atatttaact tgaacgattt cgaaaccaaa     240
gaggatatgg tccaggccac atctgagacg cgccaacatg gtggggacct cacaaacacc     300
ttcagagcta tcgaattcgc aagagactac gcttattcac agacttctgg cgggcgcccg     360
ggtgctacaa aagtcatggt agttgtgacc gatggcgagt cccatgatgg gtcgaagctg     420
aaaactgtga tccagcaatg caatgatgac gagatactga ggttcggcat agcagttctt     480
gggtatttaa acagaaatgc tcttgatact aaaaatttaa tcaaagaaat aaaagcaatt     540
gctagtactc caaccgagag atacttttc aatgtgccg acgaagcggc tcttctggag      600
aaggctggaa ctctagggga gcaaatattc agcattgaag gcactgtt               648

<210> SEQ ID NO 115
<211> LENGTH: 6
<212> TYPE: DNA
<213> ORGANISM: Homo sapiens
<220> FEATURE:
<221> NAME/KEY: misc_feature
<223> OTHER INFORMATION: Exemplary upstream sequence from the start of
      gene transcription
<220> FEATURE:
<221> NAME/KEY: misc_feature
<222> LOCATION: (2)..(2)
<223> OTHER INFORMATION: n is a, c, g, or t

<400> SEQUENCE: 115 cncaat                                                                 6

<210> SEQ ID NO 116
<211> LENGTH: 6
<212> TYPE: DNA
<213> ORGANISM: Homo sapiens
<220> FEATURE:
<221> NAME/KEY: misc_feature
<223> OTHER INFORMATION: Exemplary sequence at 3' end of gene

<400> SEQUENCE: 116 aataaa                                                                 6

<210> SEQ ID NO 117
<211> LENGTH: 31
<212> TYPE: DNA
<213> ORGANISM: Homo Sapiens
<220> FEATURE:
<221> NAME/KEY: misc_feature
<223> OTHER INFORMATION: halphaI F

<400> SEQUENCE: 117
ggggatccag tcctgaattt tcagctctca g                                    31

<210> SEQ ID NO 118
<211> LENGTH: 27
<212> TYPE: DNA
<213> ORGANISM: Homo Sapiens
```

```
<220> FEATURE:
<221> NAME/KEY: misc_feature
<223> OTHER INFORMATION: halphaI R

<400> SEQUENCE: 118
gggaattcaa cagtaccttc aatgctg                                              27

<210> SEQ ID NO 119
<211> LENGTH: 19
<212> TYPE: DNA
<213> ORGANISM: Homo sapiens
<220> FEATURE:
<221> NAME/KEY: misc_feature
<223> OTHER INFORMATION: Human I domain forward primer

<400> SEQUENCE: 119
ggggatccag tcctgattt                                                       19

<210> SEQ ID NO 120
<211> LENGTH: 18
<212> TYPE: DNA
<213> ORGANISM: Homo sapiens
<220> FEATURE:
<221> NAME/KEY: misc_feature
<223> OTHER INFORMATION: Human I domain reverse primer

<400> SEQUENCE: 120
ggaattcaac agtacctt                                                        18

<210> SEQ ID NO 121
<211> LENGTH: 29
<212> TYPE: DNA
<213> ORGANISM: Homo Sapiens
<220> FEATURE:
<221> NAME/KEY: misc_feature
<223> OTHER INFORMATION: malphaI F

<400> SEQUENCE: 121
ggggatccag tccagacttt cagttcttg                                            29

<210> SEQ ID NO 122
<211> LENGTH: 28
<212> TYPE: DNA
<213> ORGANISM: Homo Sapiens
<220> FEATURE:
<221> NAME/KEY: misc_feature
<223> OTHER INFORMATION: malphaI R

<400> SEQUENCE: 122
tgggaattca acagtgcctt caatgctg                                             28

<210> SEQ ID NO 123
<211> LENGTH: 31
<212> TYPE: DNA
<213> ORGANISM: Homo Sapiens
<220> FEATURE:
<221> NAME/KEY: misc_feature
<223> OTHER INFORMATION: ralphaI F

<400> SEQUENCE: 123
ggggatccag tccagacttt cagtcgttga c                                         31

<210> SEQ ID NO 124
<211> LENGTH: 31
<212> TYPE: DNA
<213> ORGANISM: Homo Sapiens
<220> FEATURE:
<221> NAME/KEY: misc_feature
```

<223> OTHER INFORMATION: ralphaI R

<400> SEQUENCE: 124
tgggaattct gccatttcca tctggaagtt g                                    31

<210> SEQ ID NO 125
<211> LENGTH: 34
<212> TYPE: DNA
<213> ORGANISM: Homo Sapiens
<220> FEATURE:
<221> NAME/KEY: misc_feature
<223> OTHER INFORMATION: halphaI I21V F

<400> SEQUENCE: 125
cagccctgcc cttccctcgt agatgttgtg gttg                                 34

<210> SEQ ID NO 126
<211> LENGTH: 34
<212> TYPE: DNA
<213> ORGANISM: Homo Sapiens
<220> FEATURE:
<221> NAME/KEY: misc_feature
<223> OTHER INFORMATION: halphaI I21V R

<400> SEQUENCE: 126
caaccacaac atctacgagg gaagggcagg gctg                                 34

<210> SEQ ID NO 127
<211> LENGTH: 33
<212> TYPE: DNA
<213> ORGANISM: Homo Sapiens
<220> FEATURE:
<221> NAME/KEY: misc_feature
<223> OTHER INFORMATION: halphaI E44V F

<400> SEQUENCE: 127
cagtaaagaa tttttggta aaatttgtca agg                                   33

<210> SEQ ID NO 128
<211> LENGTH: 33
<212> TYPE: DNA
<213> ORGANISM: Homo Sapiens
<220> FEATURE:
<221> NAME/KEY: misc_feature
<223> OTHER INFORMATION: halphaI E44V R

<400> SEQUENCE: 128
ccttgacaaa ttttaccaaa aaattcttta ctg                                  33

<210> SEQ ID NO 129
<211> LENGTH: 35
<212> TYPE: DNA
<213> ORGANISM: Homo Sapiens
<220> FEATURE:
<221> NAME/KEY: misc_feature
<223> OTHER INFORMATION: halphaI Q48T F

<400> SEQUENCE: 129
ttttggaaaa atttgtaaca ggcctggata taggc                                35

<210> SEQ ID NO 130
<211> LENGTH: 35
<212> TYPE: DNA
<213> ORGANISM: Homo Sapiens
<220> FEATURE:
<221> NAME/KEY: misc_feature
<223> OTHER INFORMATION: halphaI Q48T R

```
<400> SEQUENCE: 130
gcctatatcc aggcctgtta caaattttc cgggg                              35

<210> SEQ ID NO 131
<211> LENGTH: 33
<212> TYPE: DNA
<213> ORGANISM: Homo Sapiens
<220> FEATURE:
<221> NAME/KEY: misc_feature
<223> OTHER INFORMATION: halphaI N67E F

<400> SEQUENCE: 131
cagtatgcca atgagccaag agttgtgttt aac                               33

<210> SEQ ID NO 132
<211> LENGTH: 33
<212> TYPE: DNA
<213> ORGANISM: Homo Sapiens
<220> FEATURE:
<221> NAME/KEY: misc_feature
<223> OTHER INFORMATION: halphaI N67E R

<400> SEQUENCE: 132
gttaaacaca actcttggct cattggcata ctg                               33

<210> SEQ ID NO 133
<211> LENGTH: 34
<212> TYPE: DNA
<213> ORGANISM: homo Sapiens
<220> FEATURE:
<221> NAME/KEY: misc_feature
<223> OTHER INFORMATION: halphaI V70I F

<400> SEQUENCE: 133
tgccaataat ccaagaattg tgtttaactt gaac                              34

<210> SEQ ID NO 134
<211> LENGTH: 33
<212> TYPE: DNA
<213> ORGANISM: Homo Sapiens
<220> FEATURE:
<221> NAME/KEY: misc_feature
<223> OTHER INFORMATION: halphaI V70I R

<400> SEQUENCE: 134
gttcaagtta acacaattct tggattattg gca                               33

<210> SEQ ID NO 135
<211> LENGTH: 34
<212> TYPE: DNA
<213> ORGANISM: Homo Sapiens
<220> FEATURE:
<221> NAME/KEY: misc_feature
<223> OTHER INFORMATION: halphaI V71I F

<400> SEQUENCE: 135
ccaataatcc aagagttatc tttaacttga acac                              34

<210> SEQ ID NO 136
<211> LENGTH: 34
<212> TYPE: DNA
<213> ORGANISM: Homo Sapiens
<220> FEATURE:
<221> NAME/KEY: misc_feature
<223> OTHER INFORMATION: halphaI V71I R

<400> SEQUENCE: 136
```

```
gtgttcaagt taaagataac tcttggatta ttgg          34
```

<210> SEQ ID NO 137
<211> LENGTH: 33
<212> TYPE: DNA
<213> ORGANISM: Homo Sapiens
<220> FEATURE:
<221> NAME/KEY: misc_feature
<223> OTHER INFORMATION: halphaI T76D F

<400> SEQUENCE: 137

```
gtgtttaact tgaacgacta taaaaccaaa gaa          33
```

<210> SEQ ID NO 138
<211> LENGTH: 33
<212> TYPE: DNA
<213> ORGANISM: Homo Sapiens
<220> FEATURE:
<221> NAME/KEY: misc_feature
<223> OTHER INFORMATION: haplhaI T76D R

<400> SEQUENCE: 138

```
ttctttggtt ttatagtcgt tcaagttaaa cac          33
```

<210> SEQ ID NO 139
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y77F F

<400> SEQUENCE: 139

```
tttaacttga acacatttaa aaccaaagaa gaa          33
```

<210> SEQ ID NO 140
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y77F R

<400> SEQUENCE: 140

```
ttcttctttg gttttaaatg tgttcaagtt aaa          33
```

<210> SEQ ID NO 141
<211> LENGTH: 33
<212> TYPE: DNA
<213> ORGANISM: Homo Sapiens
<220> FEATURE:
<221> NAME/KEY: misc_feature
<223> OTHER INFORMATION: halphaI K78E F

<400> SEQUENCE: 141

```
aacttgaaca catatgaaac caagaagaa atg          33
```

<210> SEQ ID NO 142
<211> LENGTH: 33
<212> TYPE: DNA
<213> ORGANISM: Homo Sapiens
<220> FEATURE:
<221> NAME/KEY: misc_feature
<223> OTHER INFORMATION: halphaI K78E R

<400> SEQUENCE: 142

```
catttcttct ttggtttcat atgtgttcaa gtt          33
```

<210> SEQ ID NO 143
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y93H F

<400> SEQUENCE: 143
tcccagacat cccaacatgg tggggacctc aca                                    33

<210> SEQ ID NO 144
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Y93H R

<400> SEQUENCE: 144
tgtgaggtcc ccaccatgtt gggatgtctg gga                                    33

<210> SEQ ID NO 145
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Y93F F

<400> SEQUENCE: 145
acatgggaga catcccaatt tggtggggac ctcacaaac                              39

<210> SEQ ID NO 146
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Y93F R

<400> SEQUENCE: 146
gtttgtgagg tccccaccaa attgggatgt ctcccatgt                              39

<210> SEQ ID NO 147
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Q105E F

<400> SEQUENCE: 147
ttcggagcaa ttgaatatgc aagaaaatat gcc                                    33

<210> SEQ ID NO 148
<211> LENGTH: 33
<212> TYPE: DNA
<213> ORGANISM: Homo Sapiens
<220> FEATURE:
<221> NAME/KEY: misc_feature
<223> OTHER INFORMATION: halphaI Q105E R

<400> SEQUENCE: 148
ggcatatttt cttgcatatt caattgctcc gaa                                    33

<210> SEQ ID NO 149

```
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A114Q F

<400> SEQUENCE: 149
aaatatgcct attcacaagc ttctggtggg cgacgaagt                              39

<210> SEQ ID NO 150
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A114Q R

<400> SEQUENCE: 150
acttcgtcgc ccaccagaag cttgtgaata ggcatattt                              39

<210> SEQ ID NO 151
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115T F

<400> SEQUENCE: 151
aaatatgcct attcagcaac ttctggtggg cgacgaagt                              39

<210> SEQ ID NO 152
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115T R

<400> SEQUENCE: 152
acttcgtcgc ccaccagaag ttgctgaata ggcatattt                              39

<210> SEQ ID NO 153
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115Q F

<400> SEQUENCE: 153
aaatatgcct attcagcaca gtctggtggg cgacgaagt                              39

<210> SEQ ID NO 154
<211> LENGTH: 39
<212> TYPE: DNA
<213> ORGANISM: Homo Sapiens
<220> FEATURE:
<221> NAME/KEY: misc_feature
<223> OTHER INFORMATION: halphaI A115Q R

<400> SEQUENCE: 154
acttcgtcgc ccaccagact gtgctgaata ggcatattt                              39

<210> SEQ ID NO 155
<211> LENGTH: 39
<212> TYPE: DNA
```

```
<213> ORGANISM: Homo Sapiens
<220> FEATURE:
<221> NAME/KEY: misc_feature
<223> OTHER INFORMATION: halphaI R165D F

<400> SEQUENCE: 155
gttcttgggt acttaaacga caacgccctt gatactaaa                              39

<210> SEQ ID NO 156
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R165D R

<400> SEQUENCE: 156
tttagtatca agggcgttgt cgtttaagta cccaagaac                              39

<210> SEQ ID NO 157
<211> LENGTH: 39
<212> TYPE: DNA
<213> ORGANISM: Homo Sapiens
<220> FEATURE:
<221> NAME/KEY: misc_feature
<223> OTHER INFORMATION: halphaI N166D F

<400> SEQUENCE: 157
cttgggtact aaacaggga cgcccttgat actaaaaat                               39

<210> SEQ ID NO 158
<211> LENGTH: 39
<212> TYPE: DNA
<213> ORGANISM: Homo Sapiens
<220> FEATURE:
<221> NAME/KEY: misc_feature
<223> OTHER INFORMATION: halphaI N166D R

<400> SEQUENCE: 158 attttagta tcaagggcgt ccctgtttaa gtacccaag                               39

<210> SEQ ID NO 159
<211> LENGTH: 40
<212> TYPE: DNA
<213> ORGANISM: Homo Sapiens
<220> FEATURE:
<221> NAME/KEY: misc_feature
<223> OTHER INFORMATION: halphaI E195W F

<400> SEQUENCE: 159
ttcaatgtgt ctgattgggc agctctacta gaaaaggctg                             40

<210> SEQ ID NO 160
<211> LENGTH: 40
<212> TYPE: DNA
<213> ORGANISM: Homo Sapiens
<220> FEATURE:
<221> NAME/KEY: misc_feature
<223> OTHER INFORMATION: halphaI E195W R

<400> SEQUENCE: 160 cagcctttc tagtagagct gcccaatcag acacattgaa                              40

<210> SEQ ID NO 161
<211> LENGTH: 38
<212> TYPE: DNA
<213> ORGANISM: Homo Sapiens
<220> FEATURE:
```

<221> NAME/KEY: misc_feature
<223> OTHER INFORMATION: halphaI K40D F

<400> SEQUENCE: 161
atccttggga tgcagtagac aattttttgg aaaaattt                               38

<210> SEQ ID NO 162
<211> LENGTH: 38
<212> TYPE: DNA
<213> ORGANISM: Homo Sapiens
<220> FEATURE:
<221> NAME/KEY: misc_feature
<223> OTHER INFORMATION: halphaI K40D R

<400> SEQUENCE: 162 aaattttttcc aaaaaattgt ctactgcatc ccaaggat                              38

<210> SEQ ID NO 163
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R69D F

<400> SEQUENCE: 163
cagtatgcca ataatccaga cgttgtgttt aacttgaac                              39

<210> SEQ ID NO 164
<211> LENGTH: 39
<212> TYPE: DNA
<213> ORGANISM: Homo Sapiens
<220> FEATURE:
<221> NAME/KEY: misc_feature
<223> OTHER INFORMATION: halphaI R69D R

<400> SEQUENCE: 164
gttcaagtta aacacaacgt ctggattatt ggcatactg                              39

<210> SEQ ID NO 165
<211> LENGTH: 36
<212> TYPE: DNA
<213> ORGANISM: Homo Sapiens
<220> FEATURE:
<221> NAME/KEY: misc_feature
<223> OTHER INFORMATION: halphaI N73D F

<400> SEQUENCE: 165
aatccaagag ttgtgtttga cttgaacaca tataaa                                 36

<210> SEQ ID NO 166
<211> LENGTH: 36
<212> TYPE: DNA
<213> ORGANISM: Homo Sapiens
<220> FEATURE:
<221> NAME/KEY: misc_feature
<223> OTHER INFORMATION: halphaI N73D R

<400> SEQUENCE: 166
tttatatgtg ttcaagtcaa acacaactct tggatt                                 36

<210> SEQ ID NO 167
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Q89H F

<400> SEQUENCE: 167
atgattgtag caacatccca cacatcccaa tatggtggg    39

<210> SEQ ID NO 168
<211> LENGTH: 39
<212> TYPE: DNA
<213> ORGANISM: Homo Sapiens
<220> FEATURE:
<221> NAME/KEY: misc_feature
<223> OTHER INFORMATION: halphaI Q89H R

<400> SEQUENCE: 168
atgattgtag caacatccca cacatcccaa tatggtggg    39

<210> SEQ ID NO 169
<211> LENGTH: 40
<212> TYPE: DNA
<213> ORGANISM: Homo Sapiens
<220> FEATURE:
<221> NAME/KEY: misc_feature
<223> OTHER INFORMATION: malphaI H93Y F

<400> SEQUENCE: 169
cacatctgag acgcgccaat atggtgggga cctcacaaac    40

<210> SEQ ID NO 170
<211> LENGTH: 40
<212> TYPE: DNA
<213> ORGANISM: Homo Sapiens
<220> FEATURE:
<221> NAME/KEY: misc_feature
<223> OTHER INFORMATION: malphaI H93Y R

<400> SEQUENCE: 170
gtttgtgagg tccccaccat attggcgcgt ctcagatgtg    40

<210> SEQ ID NO 171
<211> LENGTH: 216
<212> TYPE: PRT
<213> ORGANISM: Macaca fascicularis
<220> FEATURE:
<221> NAME/KEY: MISC_FEATURE
<223> OTHER INFORMATION: Cynomologus

<400> SEQUENCE: 171

```
Ser Pro Asp Phe Gln Leu Ser Ala Ser Phe Ser Pro Ala Thr Gln Pro
1               5                   10                  15

Cys Pro Ser Leu Ile Asp Val Val Val Cys Asp Glu Ser Asn Ser
            20                  25                  30

Ile Tyr Pro Trp Asp Ala Val Asp Asn Phe Leu Glu Lys Phe Val Gln
        35                  40                  45

Gly Leu Asp Ile Gly Pro Thr Lys Thr Gln Val Gly Leu Ile Gln Tyr
    50                  55                  60

Ala Asn Asn Pro Arg Val Val Phe Asn Leu Asn Thr Tyr Lys Thr Lys
65                  70                  75                  80

Glu Glu Met Ile Val Ala Thr Ser Gln Thr Ser Gln Tyr Gly Gly Asp
                85                  90                  95

Leu Thr Asn Thr Phe Gly Ala Ile Gln Tyr Ala Arg Lys Tyr Ala Tyr
            100                 105                 110

Ser Ala Ala Ser Gly Gly Arg Arg Ser Ala Thr Lys Val Met Val Val
        115                 120                 125

Val Thr Asp Gly Glu Ser His Asp Gly Ser Met Leu Lys Ala Val Ile
```

```
                130                 135                 140
Asp Gln Cys Asn His Asp Asn Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175

Ile Lys Ala Ile Ala Ser Ile Pro Thr Glu Arg Tyr Phe Phe Asn Val
                180                 185                 190

Ser Asp Glu Ala Ala Leu Leu Glu Lys Ala Gly Thr Leu Gly Glu Gln
                195                 200                 205

Ile Phe Ser Ile Glu Gly Thr Val
                210                 215

<210> SEQ ID NO 172
<211> LENGTH: 216
<212> TYPE: PRT
<213> ORGANISM: Macaca mulatta
<220> FEATURE:
<221> NAME/KEY: MISC_FEATURE
<223> OTHER INFORMATION: Rhesus

<400> SEQUENCE: 172

Ser Pro Asp Phe Gln Leu Ser Ala Ser Phe Ser Pro Ala Thr Gln Pro
1               5                   10                  15

Cys Pro Ser Leu Ile Asp Val Val Val Val Cys Asp Glu Ser Asn Ser
                20                  25                  30

Ile Tyr Pro Trp Asp Ala Val Lys Asn Phe Leu Glu Lys Phe Val Gln
                35                  40                  45

Gly Leu Asp Ile Gly Pro Thr Lys Thr Gln Val Gly Leu Ile Gln Tyr
50                  55                  60

Ala Asn Asn Pro Arg Val Val Phe Asn Leu Asn Thr Tyr Lys Thr Lys
65                  70                  75                  80

Glu Glu Met Ile Val Ala Thr Ser Gln Thr Ser Gln Tyr Gly Gly Asp
                85                  90                  95

Leu Thr Asn Thr Phe Gly Ala Ile Gln Tyr Ala Arg Lys Tyr Ala Tyr
                100                 105                 110

Ser Ala Ala Ser Gly Gly Arg Arg Ser Ala Thr Lys Val Met Val Val
                115                 120                 125

Val Thr Asp Gly Glu Ser His Asp Gly Ser Met Leu Lys Ala Val Ile
                130                 135                 140

Asp Gln Cys Asn His Asp Asn Ile Leu Arg Phe Gly Ile Ala Val Leu
145                 150                 155                 160

Gly Tyr Leu Asn Arg Asn Ala Leu Asp Thr Lys Asn Leu Ile Lys Glu
                165                 170                 175

Ile Lys Ala Ile Ala Ser Ile Pro Thr Glu Arg Tyr Phe Phe Asn Val
                180                 185                 190

Ser Asp Glu Ala Ala Leu Leu Glu Lys Ala Gly Thr Leu Gly Glu Gln
                195                 200                 205

Ile Phe Ser Ile Glu Gly Thr Val
                210                 215

<210> SEQ ID NO 173
<211> LENGTH: 1435
<212> TYPE: DNA
<213> ORGANISM: Homo Sapiens
<220> FEATURE:
<221> NAME/KEY: misc_feature
<223> OTHER INFORMATION: hvH14.0 IgG4 Heavy Chain
<220> FEATURE:
<221> NAME/KEY: CDS
```

<222> LOCATION: (22)..(1416)

<400> SEQUENCE: 173

| | | | | | | | | | | |
|---|---|---|---|---|---|---|---|---|---|---|
| tctcgagaag cttccaccat g gag aca gac aca ctc ctg cta tgg gta ctg | | | | | | | | | | 51 |
| | Glu Thr Asp Thr Leu Leu Leu Trp Val Leu | | | | | | | | | |
| | 1 | | | 5 | | | | | 10 | |

| | | | | | | | | | | |
|---|---|---|---|---|---|---|---|---|---|---|
| ctg ctc tgg gtt cca ggt tcc act gga cag gtg cag ttg cag gag tca | | | | | | | | | | 99 |
| Leu Leu Trp Val Pro Gly Ser Thr Gly Gln Val Gln Leu Gln Glu Ser | | | | | | | | | | |
| | | | 15 | | | 20 | | | 25 | |

| | | | | | | | | | | |
|---|---|---|---|---|---|---|---|---|---|---|
| ggc cct ggc ctg gtg aag ccc agc gag acc ctg agc ctg acc tgt acc | | | | | | | | | | 147 |
| Gly Pro Gly Leu Val Lys Pro Ser Glu Thr Leu Ser Leu Thr Cys Thr | | | | | | | | | | |
| | | 30 | | | | 35 | | | 40 | |

| | | | | | | | | | | |
|---|---|---|---|---|---|---|---|---|---|---|
| gtc tct gga ttt agc tta acc aac tat ggc atc cac tgg ata cgc cag | | | | | | | | | | 195 |
| Val Ser Gly Phe Ser Leu Thr Asn Tyr Gly Ile His Trp Ile Arg Gln | | | | | | | | | | |
| | | 45 | | | | 50 | | | 55 | |

| | | | | | | | | | | |
|---|---|---|---|---|---|---|---|---|---|---|
| cct cca ggc aag ggc ctg gag tgg ctg ggc gtg ata tgg gct cgc ggc | | | | | | | | | | 243 |
| Pro Pro Gly Lys Gly Leu Glu Trp Leu Gly Val Ile Trp Ala Arg Gly | | | | | | | | | | |
| | 60 | | | | 65 | | | 70 | | |

| | | | | | | | | | | |
|---|---|---|---|---|---|---|---|---|---|---|
| ttc aca aac tat aac agc gct ctc atg tcc cgc gtg acc atc agc aag | | | | | | | | | | 291 |
| Phe Thr Asn Tyr Asn Ser Ala Leu Met Ser Arg Val Thr Ile Ser Lys | | | | | | | | | | |
| 75 | | | | 80 | | | 85 | | | 90 |

| | | | | | | | | | | |
|---|---|---|---|---|---|---|---|---|---|---|
| gac aac agc aag aac cag gtg agc ctg aag ctg agc agc gtg acc gcc | | | | | | | | | | 339 |
| Asp Asn Ser Lys Asn Gln Val Ser Leu Lys Leu Ser Ser Val Thr Ala | | | | | | | | | | |
| | | | 95 | | | 100 | | | 105 | |

| | | | | | | | | | | |
|---|---|---|---|---|---|---|---|---|---|---|
| gcg gac acc gcc gtg tac tac tgc gcc aga gcc aac gac ggg gtc tac | | | | | | | | | | 387 |
| Ala Asp Thr Ala Val Tyr Tyr Cys Ala Arg Ala Asn Asp Gly Val Tyr | | | | | | | | | | |
| | | 110 | | | | 115 | | | 120 | |

| | | | | | | | | | | |
|---|---|---|---|---|---|---|---|---|---|---|
| tat gcc atg gac tac tgg ggc cag gga acc ctg gtc acc gtc agc tca | | | | | | | | | | 435 |
| Tyr Ala Met Asp Tyr Trp Gly Gln Gly Thr Leu Val Thr Val Ser Ser | | | | | | | | | | |
| | | 125 | | | | 130 | | | 135 | |

| | | | | | | | | | | |
|---|---|---|---|---|---|---|---|---|---|---|
| gcg tcc acc aag ggc cca tcc gtc ttc ccc ctg gcg ccc tgc tcc agg | | | | | | | | | | 483 |
| Ala Ser Thr Lys Gly Pro Ser Val Phe Pro Leu Ala Pro Cys Ser Arg | | | | | | | | | | |
| | 140 | | | | 145 | | | 150 | | |

| | | | | | | | | | | |
|---|---|---|---|---|---|---|---|---|---|---|
| agc acc tcc gag agc aca gcc gcc ctg ggc tgc ctg gtc aag gac tac | | | | | | | | | | 531 |
| Ser Thr Ser Glu Ser Thr Ala Ala Leu Gly Cys Leu Val Lys Asp Tyr | | | | | | | | | | |
| 155 | | | | 160 | | | 165 | | | 170 |

| | | | | | | | | | | |
|---|---|---|---|---|---|---|---|---|---|---|
| ttc ccc gaa ccg gtg acg gtg tcg tgg aac tca ggc gcc ctg acc agc | | | | | | | | | | 579 |
| Phe Pro Glu Pro Val Thr Val Ser Trp Asn Ser Gly Ala Leu Thr Ser | | | | | | | | | | |
| | | | 175 | | | 180 | | | 185 | |

| | | | | | | | | | | |
|---|---|---|---|---|---|---|---|---|---|---|
| ggc gtg cac acc ttc ccg gct gtc cta cag tcc tca gga ctc tac tcc | | | | | | | | | | 627 |
| Gly Val His Thr Phe Pro Ala Val Leu Gln Ser Ser Gly Leu Tyr Ser | | | | | | | | | | |
| | | 190 | | | | 195 | | | 200 | |

| | | | | | | | | | | |
|---|---|---|---|---|---|---|---|---|---|---|
| ctc agc agc gtg gtg acc gtg ccc tcc agc agc ttg ggc acg aag acc | | | | | | | | | | 675 |
| Leu Ser Ser Val Val Thr Val Pro Ser Ser Ser Leu Gly Thr Lys Thr | | | | | | | | | | |
| | 205 | | | | 210 | | | 215 | | |

| | | | | | | | | | | |
|---|---|---|---|---|---|---|---|---|---|---|
| tac acc tgc aac gta gat cac aag ccc agc aac acc aag gtg gac aag | | | | | | | | | | 723 |
| Tyr Thr Cys Asn Val Asp His Lys Pro Ser Asn Thr Lys Val Asp Lys | | | | | | | | | | |
| | 220 | | | | 225 | | | 230 | | |

| | | | | | | | | | | |
|---|---|---|---|---|---|---|---|---|---|---|
| aga gtt gag tcc aaa tat ggt ccc cca tgc cca tca tgc cca gca cct | | | | | | | | | | 771 |
| Arg Val Glu Ser Lys Tyr Gly Pro Pro Cys Pro Ser Cys Pro Ala Pro | | | | | | | | | | |
| 235 | | | | 240 | | | 245 | | | 250 |

| | | | | | | | | | | |
|---|---|---|---|---|---|---|---|---|---|---|
| gag ttc ctg ggg gga cca tca gtc ttc ctg ttc ccc cca aaa ccc aag | | | | | | | | | | 819 |
| Glu Phe Leu Gly Gly Pro Ser Val Phe Leu Phe Pro Pro Lys Pro Lys | | | | | | | | | | |
| | | | 255 | | | 260 | | | 265 | |

| | | | | | | | | | | |
|---|---|---|---|---|---|---|---|---|---|---|
| gac act ctc atg atc tcc cgg acc cct gag gtc acg tgc gtg gtg gtg | | | | | | | | | | 867 |
| Asp Thr Leu Met Ile Ser Arg Thr Pro Glu Val Thr Cys Val Val Val | | | | | | | | | | |
| | | 270 | | | | 275 | | | 280 | |

| | | | | | | | | | | |
|---|---|---|---|---|---|---|---|---|---|---|
| gac gtg agc cag gaa gac ccc gag gtc cag ttc aac tgg tac gtg gat | | | | | | | | | | 915 |
| Asp Val Ser Gln Glu Asp Pro Glu Val Gln Phe Asn Trp Tyr Val Asp | | | | | | | | | | |
| | | 285 | | | | 290 | | | 295 | |

```
ggc gtg gag gtg cat aat gcc aag aca aag ccg cgg gag gag cag ttc    963
Gly Val Glu Val His Asn Ala Lys Thr Lys Pro Arg Glu Glu Gln Phe
300                 305                 310 aac agc acg tac cgt gtg gtc agc gtc ctc acc gtc ctg cac cag gac   1011
Asn Ser Thr Tyr Arg Val Val Ser Val Leu Thr Val Leu His Gln Asp
315                 320                 325                 330 tgg ctg aac ggc aag gag tac aag tgc aag gtc tcc aac aaa ggc ctc   1059
Trp Leu Asn Gly Lys Glu Tyr Lys Cys Lys Val Ser Asn Lys Gly Leu
                335                 340                 345 ccg tcc tcc atc gag aaa acc atc tcc aaa gcc aaa ggg cag ccc cga   1107
Pro Ser Ser Ile Glu Lys Thr Ile Ser Lys Ala Lys Gly Gln Pro Arg
            350                 355                 360 gag cca cag gtg tac acc ctg ccc cca tcc cag gag gag atg acc aag   1155
Glu Pro Gln Val Tyr Thr Leu Pro Pro Ser Gln Glu Glu Met Thr Lys
        365                 370                 375 aac cag gtc agc ctg acc tgc ctg gtc aaa ggc ttc tac ccc agc gac   1203
Asn Gln Val Ser Leu Thr Cys Leu Val Lys Gly Phe Tyr Pro Ser Asp
380                 385                 390 atc gcc gtg gag tgg gag agc aat ggg cag ccg gag aac aac tac aag   1251
Ile Ala Val Glu Trp Glu Ser Asn Gly Gln Pro Glu Asn Asn Tyr Lys
395                 400                 405                 410 acc acg cct ccc gtg ctg gac tcc gac ggc tcc ttc ttc ctc tac agc   1299
Thr Thr Pro Pro Val Leu Asp Ser Asp Gly Ser Phe Phe Leu Tyr Ser
                415                 420                 425 agg cta acc gtg gac aag agc agg tgg cag gag ggg aat gtc ttc tca   1347
Arg Leu Thr Val Asp Lys Ser Arg Trp Gln Glu Gly Asn Val Phe Ser
            430                 435                 440 tgc tcc gtg atg cat gag gct ctg cac aac cac tac aca cag aag agc   1395
Cys Ser Val Met His Glu Ala Leu His Asn His Tyr Thr Gln Lys Ser
        445                 450                 455 ctc tcc ctg tct ctg ggt aaa tgataggatc cgcggccgc                  1435
Leu Ser Leu Ser Leu Gly Lys
        460                 465

<210> SEQ ID NO 174
<211> LENGTH: 465
<212> TYPE: PRT
<213> ORGANISM: Homo Sapiens

<400> SEQUENCE: 174

Glu Thr Asp Thr Leu Leu Leu Trp Val Leu Leu Leu Trp Val Pro Gly
1               5                   10                  15

Ser Thr Gly Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Asn Tyr Gly Ile His Trp Ile Arg Gln Pro Pro Gly Lys Gly Leu
    50                  55                  60

Glu Trp Leu Gly Val Ile Trp Ala Arg Gly Phe Thr Asn Tyr Asn Ser
65                  70                  75                  80

Ala Leu Met Ser Arg Val Thr Ile Ser Lys Asp Asn Ser Lys Asn Gln
                85                  90                  95

Val Ser Leu Lys Leu Ser Ser Val Thr Ala Ala Asp Thr Ala Val Tyr
            100                 105                 110

Tyr Cys Ala Arg Ala Asn Asp Gly Val Tyr Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
```

```
                145                 150                 155                 160
Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
        180                 185                 190

Ala Val Leu Gln Ser Ser Gly Leu Tyr Ser Leu Ser Ser Val Val Thr
    195                 200                 205

Val Pro Ser Ser Ser Leu Gly Thr Lys Thr Tyr Thr Cys Asn Val Asp
210                 215                 220

His Lys Pro Ser Asn Thr Lys Val Asp Lys Arg Val Glu Ser Lys Tyr
225                 230                 235                 240

Gly Pro Pro Cys Pro Ser Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465

<210> SEQ ID NO 175
<211> LENGTH: 1435
<212> TYPE: DNA
<213> ORGANISM: Homo Sapiens
<220> FEATURE:
<221> NAME/KEY: misc_feature
<223> OTHER INFORMATION: hvH12.0 IgG4 Heavy Chain
<220> FEATURE:
<221> NAME/KEY: CDS
<222> LOCATION: (22)..(1416)

<400> SEQUENCE: 175
tctcgagaag cttccaccat g gag aca gac aca ctc ctg cta tgg gta ctg       51
                       Glu Thr Asp Thr Leu Leu Leu Trp Val Leu
                        1               5                  10
```

```
ctg ctc tgg gtt cca ggt tcc act gga cag gtg cag ttg cag gag tca    99
Leu Leu Trp Val Pro Gly Ser Thr Gly Gln Val Gln Leu Gln Glu Ser
         15                  20                  25 ggc cct ggc ctg gtg aag ccc agc gag acc ctg agc ctg acc tgt acc   147
Gly Pro Gly Leu Val Lys Pro Ser Glu Thr Leu Ser Leu Thr Cys Thr
 30                  35                  40 gtc tct gga ttt agc tta acc aac tat ggc atc cac tgg ata cgc cag   195
Val Ser Gly Phe Ser Leu Thr Asn Tyr Gly Ile His Trp Ile Arg Gln
         45                  50                  55 cct cca ggc aag ggc ctg gag tgg ctg ggc gtg ata tgg gct cgc ggc   243
Pro Pro Gly Lys Gly Leu Glu Trp Leu Gly Val Ile Trp Ala Arg Gly
 60                  65                  70 ttc aca aac tat aac agc gct ctc atg tcc cgc ctg acc atc agc aag   291
Phe Thr Asn Tyr Asn Ser Ala Leu Met Ser Arg Leu Thr Ile Ser Lys
75                  80                  85                  90 gac aac agc aag aac cag gtg agc ctg aag ctg agc agc gtg acc gcc   339
Asp Asn Ser Lys Asn Gln Val Ser Leu Lys Leu Ser Ser Val Thr Ala
         95                 100                 105 gcg gac acc gcc gtg tac tac tgc gcc aga gcc aac gac ggg gtc tac   387
Ala Asp Thr Ala Val Tyr Tyr Cys Ala Arg Ala Asn Asp Gly Val Tyr
         110                 115                 120 tat gcc atg gac tac tgg ggc cag gga acc ctg gtc acc gtc agc tca   435
Tyr Ala Met Asp Tyr Trp Gly Gln Gly Thr Leu Val Thr Val Ser Ser
         125                 130                 135 gcg tcc acc aag ggc cca tcc gtc ttc ccc ctg gcg ccc tgc tcc agg   483
Ala Ser Thr Lys Gly Pro Ser Val Phe Pro Leu Ala Pro Cys Ser Arg
 140                 145                 150 agc acc tcc gag agc aca gcc gcc ctg ggc tgc ctg gtc aag gac tac   531
Ser Thr Ser Glu Ser Thr Ala Ala Leu Gly Cys Leu Val Lys Asp Tyr
155                 160                 165                 170 ttc ccc gaa ccg gtg acg gtg tcg tgg aac tca ggc gcc ctg acc agc   579
Phe Pro Glu Pro Val Thr Val Ser Trp Asn Ser Gly Ala Leu Thr Ser
             175                 180                 185 ggc gtg cac acc ttc ccg gct gtc cta cag tcc tca gga ctc tac tcc   627
Gly Val His Thr Phe Pro Ala Val Leu Gln Ser Ser Gly Leu Tyr Ser
             190                 195                 200 ctc agc agc gtg gtg acc gtg ccc tcc agc agc ttg ggc acg aag acc   675
Leu Ser Ser Val Val Thr Val Pro Ser Ser Ser Leu Gly Thr Lys Thr
         205                 210                 215 tac acc tgc aac gta gat cac aag ccc agc aac acc aag gtg gac aag   723
Tyr Thr Cys Asn Val Asp His Lys Pro Ser Asn Thr Lys Val Asp Lys
 220                 225                 230 aga gtt gag tcc aaa tat ggt ccc cca tgc cca tca tgc cca gca cct   771
Arg Val Glu Ser Lys Tyr Gly Pro Pro Cys Pro Ser Cys Pro Ala Pro
235                 240                 245                 250 gag ttc ctg ggg gga cca tca gtc ttc ctg ttc ccc cca aaa ccc aag   819
Glu Phe Leu Gly Gly Pro Ser Val Phe Leu Phe Pro Pro Lys Pro Lys
             255                 260                 265 gac act ctc atg atc tcc cgg acc cct gag gtc acg tgc gtg gtg gtg   867
Asp Thr Leu Met Ile Ser Arg Thr Pro Glu Val Thr Cys Val Val Val
             270                 275                 280 gac gtg agc cag gaa gac ccc gag gtc cag ttc aac tgg tac gtg gat   915
Asp Val Ser Gln Glu Asp Pro Glu Val Gln Phe Asn Trp Tyr Val Asp
         285                 290                 295 ggc gtg gag gtg cat aat gcc aag aca aag ccg cgg gag gag cag ttc   963
Gly Val Glu Val His Asn Ala Lys Thr Lys Pro Arg Glu Glu Gln Phe
 300                 305                 310 aac agc acg tac cgt gtg gtc agc gtc ctc acc gtc ctg cac cag gac  1011
Asn Ser Thr Tyr Arg Val Val Ser Val Leu Thr Val Leu His Gln Asp
315                 320                 325                 330
```

```
tgg ctg aac ggc aag gag tac aag tgc aag gtc tcc aac aaa ggc ctc    1059
Trp Leu Asn Gly Lys Glu Tyr Lys Cys Lys Val Ser Asn Lys Gly Leu
            335                 340                 345 ccg tcc tcc atc gag aaa acc atc tcc aaa gcc aaa ggg cag ccc cga    1107
Pro Ser Ser Ile Glu Lys Thr Ile Ser Lys Ala Lys Gly Gln Pro Arg
        350                 355                 360 gag cca cag gtg tac acc ctg ccc cca tcc cag gag gag atg acc aag    1155
Glu Pro Gln Val Tyr Thr Leu Pro Pro Ser Gln Glu Glu Met Thr Lys
    365                 370                 375 aac cag gtc agc ctg acc tgc ctg gtc aaa ggc ttc tac ccc agc gac    1203
Asn Gln Val Ser Leu Thr Cys Leu Val Lys Gly Phe Tyr Pro Ser Asp
380                 385                 390 atc gcc gtg gag tgg gag agc aat ggg cag ccg gag aac aac tac aag    1251
Ile Ala Val Glu Trp Glu Ser Asn Gly Gln Pro Glu Asn Asn Tyr Lys
395                 400                 405                 410 acc acg cct ccc gtg ctg gac tcc gac ggc tcc ttc ttc ctc tac agc    1299
Thr Thr Pro Pro Val Leu Asp Ser Asp Gly Ser Phe Phe Leu Tyr Ser
            415                 420                 425 agg cta acc gtg gac aag agc agg tgg cag gag ggg aat gtc ttc tca    1347
Arg Leu Thr Val Asp Lys Ser Arg Trp Gln Glu Gly Asn Val Phe Ser
        430                 435                 440 tgc tcc gtg atg cat gag gct ctg cac aac cac tac aca cag aag agc    1395
Cys Ser Val Met His Glu Ala Leu His Asn His Tyr Thr Gln Lys Ser
    445                 450                 455 ctc tcc ctg tct ctg ggt aaa tgataggatc cgcggccgc                   1435
Leu Ser Leu Ser Leu Gly Lys
    460                 465
```

<210> SEQ ID NO 176
<211> LENGTH: 465
<212> TYPE: PRT
<213> ORGANISM: Homo Sapiens

<400> SEQUENCE: 176

```
Glu Thr Asp Thr Leu Leu Leu Trp Val Leu Leu Leu Trp Val Pro Gly
1               5                   10                  15

Ser Thr Gly Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Asn Tyr Gly Ile His Trp Ile Arg Gln Pro Pro Gly Lys Gly Leu
    50                  55                  60

Glu Trp Leu Gly Val Ile Trp Ala Arg Gly Phe Thr Asn Tyr Asn Ser
65                  70                  75                  80

Ala Leu Met Ser Arg Leu Thr Ile Ser Lys Asp Asn Ser Lys Asn Gln
                85                  90                  95

Val Ser Leu Lys Leu Ser Ser Val Thr Ala Ala Asp Thr Ala Val Tyr
            100                 105                 110

Tyr Cys Ala Arg Ala Asn Asp Gly Val Tyr Tyr Ala Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190
```

```
Ala Val Leu Gln Ser Ser Gly Leu Tyr Ser Leu Ser Ser Val Val Thr
        195                 200                 205
Val Pro Ser Ser Leu Gly Thr Lys Thr Tyr Thr Cys Asn Val Asp
    210                 215                 220
His Lys Pro Ser Asn Thr Lys Val Asp Lys Arg Val Glu Ser Lys Tyr
225                 230                 235                 240
Gly Pro Pro Cys Pro Ser Cys Pro Ala Pro Glu Phe Leu Gly Gly Pro
                245                 250                 255
Ser Val Phe Leu Phe Pro Pro Lys Pro Lys Asp Thr Leu Met Ile Ser
                260                 265                 270
Arg Thr Pro Glu Val Thr Cys Val Val Val Asp Val Ser Gln Glu Asp
                275                 280                 285
Pro Glu Val Gln Phe Asn Trp Tyr Val Asp Gly Val Glu Val His Asn
            290                 295                 300
Ala Lys Thr Lys Pro Arg Glu Glu Gln Phe Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Gly Leu Pro Ser Ser Ile Glu Lys
                340                 345                 350
Thr Ile Ser Lys Ala Lys Gly Gln Pro Arg Glu Pro Gln Val Tyr Thr
                355                 360                 365
Leu Pro Pro Ser Gln Glu Glu Met Thr Lys Asn Gln Val Ser Leu Thr
            370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Arg Leu Thr Val Asp Lys
                420                 425                 430
Ser Arg Trp Gln Glu Gly Asn Val Phe Ser Cys Ser Val Met His Glu
            435                 440                 445
Ala Leu His Asn His Tyr Thr Gln Lys Ser Leu Ser Leu Ser Leu Gly
        450                 455                 460
Lys
465

<210> SEQ ID NO 177
<211> LENGTH: 744
<212> TYPE: DNA
<213> ORGANISM: Homo Sapeins
<220> FEATURE:
<221> NAME/KEY: misc_feature
<223> OTHER INFORMATION: VL10.0Q light chain
<220> FEATURE:
<221> NAME/KEY: CDS
<222> LOCATION: (22)..(720)

<400> SEQUENCE: 177
ctatctcgag aagcttccac c atg gag aca gac aca ctc ctg cta tgg gta         51
                        Met Glu Thr Asp Thr Leu Leu Leu Trp Val
                         1               5                   10 ctg ctg ctc tgg gtt cca ggt tcc act gga gac ttc gtg atg acc cag         99
Leu Leu Leu Trp Val Pro Gly Ser Thr Gly Asp Phe Val Met Thr Gln
                15                  20                  25 tct cca gca ttc ctg agc gtg acc ccc ggc gag aag gtg acc atc acc        147
Ser Pro Ala Phe Leu Ser Val Thr Pro Gly Glu Lys Val Thr Ile Thr
            30                  35                  40
```

```
tgc agc gcc caa tca agc gtg aac tac att cac tgg tac cag cag aag    195
Cys Ser Ala Gln Ser Ser Val Asn Tyr Ile His Trp Tyr Gln Gln Lys
         45                  50                  55 ccc gac cag gcc ccc aag aaa ttg atc tat gac act tcc aag ctg gcc    243
Pro Asp Gln Ala Pro Lys Lys Leu Ile Tyr Asp Thr Ser Lys Leu Ala
    60                  65                  70 agc ggc gtg ccc agc cgc ttc agc ggc agc ggc agc ggc acc gac tac    291
Ser Gly Val Pro Ser Arg Phe Ser Gly Ser Gly Ser Gly Thr Asp Tyr
75                  80                  85                  90 acc ttc acc atc agc agc ctg gag gcc gag gac gct gcc acc tat tac    339
Thr Phe Thr Ile Ser Ser Leu Glu Ala Glu Asp Ala Ala Thr Tyr Tyr
                95                 100                 105 tgc cag cag tgg acc act aac cca ctg acc ttc ggc cag ggc acc aag    387
Cys Gln Gln Trp Thr Thr Asn Pro Leu Thr Phe Gly Gln Gly Thr Lys
        110                 115                 120 gtc gaa atc aaa cga act gtg gct gca cca tct gtc ttc atc ttc ccg    435
Val Glu Ile Lys Arg Thr Val Ala Ala Pro Ser Val Phe Ile Phe Pro
    125                 130                 135 cca tct gat gag cag ttg aaa tct gga act gcc tct gtt gtg tgc ctg    483
Pro Ser Asp Glu Gln Leu Lys Ser Gly Thr Ala Ser Val Val Cys Leu
140                 145                 150 ctg aat aac ttc tat ccc aga gag gcc aaa gta cag tgg aag gtg gat    531
Leu Asn Asn Phe Tyr Pro Arg Glu Ala Lys Val Gln Trp Lys Val Asp
155                 160                 165                 170 aac gcc ctc caa tcg ggt aac tcc cag gag agt gtc aca gag cag gac    579
Asn Ala Leu Gln Ser Gly Asn Ser Gln Glu Ser Val Thr Glu Gln Asp
            175                 180                 185 agc aag gac agc acc tac agc ctc agc agc acc ctg acg ctg agc aaa    627
Ser Lys Asp Ser Thr Tyr Ser Leu Ser Ser Thr Leu Thr Leu Ser Lys
        190                 195                 200 gca gac tac gag aaa cac aaa gtc tac gcc tgc gaa gtc acc cat cag    675
Ala Asp Tyr Glu Lys His Lys Val Tyr Ala Cys Glu Val Thr His Gln
    205                 210                 215 ggc ctg agc tcg ccc gtc aca aag agc ttc aac agg gga gag tgt        720
Gly Leu Ser Ser Pro Val Thr Lys Ser Phe Asn Arg Gly Glu Cys
220                 225                 230 tgataggatc cgcggccgca tagg                                         744
```

<210> SEQ ID NO 178
<211> LENGTH: 233
<212> TYPE: PRT
<213> ORGANISM: Homo Sapeins

<400> SEQUENCE: 178

```
Met Glu Thr Asp Thr Leu Leu Leu Trp Val Leu Leu Leu Trp Val Pro
1               5                   10                  15

Gly Ser Thr Gly Asp Phe Val Met Thr Gln Ser Pro Ala Phe Leu Ser
            20                  25                  30

Val Thr Pro Gly Glu Lys Val Thr Ile Thr Cys Ser Ala Gln Ser Ser
        35                  40                  45

Val Asn Tyr Ile His Trp Tyr Gln Gln Lys Pro Asp Gln Ala Pro Lys
    50                  55                  60

Lys Leu Ile Tyr Asp Thr Ser Lys Leu Ala Ser Gly Val Pro Ser Arg
65                  70                  75                  80

Phe Ser Gly Ser Gly Ser Gly Thr Asp Tyr Thr Phe Thr Ile Ser Ser
                85                  90                  95

Leu Glu Ala Glu Asp Ala Ala Thr Tyr Tyr Cys Gln Gln Trp Thr Thr
            100                 105                 110

Asn Pro Leu Thr Phe Gly Gln Gly Thr Lys Val Glu Ile Lys Arg Thr
```

```
                    115                 120                125
Val Ala Ala Pro Ser Val Phe Ile Phe Pro Ser Asp Glu Gln Leu
130                 135                140

Lys Ser Gly Thr Ala Ser Val Val Cys Leu Leu Asn Asn Phe Tyr Pro
145                 150                 155                160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230

<210> SEQ ID NO 179
<211> LENGTH: 1460
<212> TYPE: DNA
<213> ORGANISM: Homo Sapiens
<220> FEATURE:
<221> NAME/KEY: misc_feature
<223> OTHER INFORMATION: h2206-VH14 IgG1 Heavy Chain (DANS); Positions
      -24 to -5 is the leader sequence; Position -4 to -1 are extra
      amino acids; DANS at positions -4 to -1 is preferably deleted
<220> FEATURE:
<221> NAME/KEY: CDS
<222> LOCATION: (22)..(1440)
<220> FEATURE:
<221> NAME/KEY: mat_peptide
<222> LOCATION: (94)..(1440)

<400> SEQUENCE: 179
ataggctagc ctcgagccac c atg gag aca gac aca ctc ctg cta tgg gta         51
                         Met Glu Thr Asp Thr Leu Leu Leu Trp Val
                             -20                 -15 ctg ctg ctc tgg gtt cca ggt tcc act gga gac gcg aat tca cag gtg         99
Leu Leu Leu Trp Val Pro Gly Ser Thr Gly Asp Ala Asn Ser Gln Val
        -10                  -5                  -1  1 cag ttg cag gag tca ggc cct ggc ctg gtg aag ccc agc gag acc ctg        147
Gln Leu Gln Glu Ser Gly Pro Gly Leu Val Lys Pro Ser Glu Thr Leu
         5                  10                  15 agc ctg acc tgt acc gtc tct gga ttt agc tta acc aac tat ggc atc        195
Ser Leu Thr Cys Thr Val Ser Gly Phe Ser Leu Thr Asn Tyr Gly Ile
 20                  25                  30 cac tgg ata cgc cag cct cca ggc aag ggc ctg gag tgg ctg ggc gtg        243
His Trp Ile Arg Gln Pro Pro Gly Lys Gly Leu Glu Trp Leu Gly Val
 35                  40                  45                  50 ata tgg gct cgc ggc ttc aca aac tat aac agc gct ctc atg tcc cgc        291
Ile Trp Ala Arg Gly Phe Thr Asn Tyr Asn Ser Ala Leu Met Ser Arg
                 55                  60                  65 gtg acc atc agc aag gac aac agc aag aac cag gtg agc ctg aag ctg        339
Val Thr Ile Ser Lys Asp Asn Ser Lys Asn Gln Val Ser Leu Lys Leu
                 70                  75                  80 agc agc gtg acc gcc gcg gac acc gcc gtg tac tac tgc gcc aga gcc        387
Ser Ser Val Thr Ala Ala Asp Thr Ala Val Tyr Tyr Cys Ala Arg Ala
                 85                  90                  95 aac gac ggg gtc tac tat gcc atg gac tac tgg ggc cag gga acc ctg        435
Asn Asp Gly Val Tyr Tyr Ala Met Asp Tyr Trp Gly Gln Gly Thr Leu
                100                 105                 110 gtc acc gtc agc tca gcg tcg acc aag ggc cca tcg gtc ttc ccc ctg        483
Val Thr Val Ser Ser Ala Ser Thr Lys Gly Pro Ser Val Phe Pro Leu
```

```
            115                 120                 125                 130
gca ccc tcc tcc aag agc acc tct ggg ggc aca gcg gcc ctg ggc tgc       531
Ala Pro Ser Ser Lys Ser Thr Ser Gly Gly Thr Ala Ala Leu Gly Cys
                    135                 140                 145 ctg gtc aag gac tac ttc ccc gaa ccg gtg acg gtg tca tgg aac tca       579
Leu Val Lys Asp Tyr Phe Pro Glu Pro Val Thr Val Ser Trp Asn Ser
            150                 155                 160 ggc gcc ctg acc agc ggc gtg cac acc ttc ccg gct gtc cta cag tcc       627
Gly Ala Leu Thr Ser Gly Val His Thr Phe Pro Ala Val Leu Gln Ser
        165                 170                 175 tca gga ctc tac tcc ctc agc agc gtg gtg acc gtg ccc tcc agc agc       675
Ser Gly Leu Tyr Ser Leu Ser Ser Val Val Thr Val Pro Ser Ser Ser
    180                 185                 190 ttg ggc acc cag acc tac atc tgc aac gtg aat cac aag ccc agc aac       723
Leu Gly Thr Gln Thr Tyr Ile Cys Asn Val Asn His Lys Pro Ser Asn
195                 200                 205                 210 acc aag gtg gac aag aaa gtt gag ccc aaa tct tgt gac aaa act cac       771
Thr Lys Val Asp Lys Lys Val Glu Pro Lys Ser Cys Asp Lys Thr His
            215                 220                 225 aca tgc cca ccg tgc cca gca cct gaa ctc ctg ggg gga ccg tca gtc       819
Thr Cys Pro Pro Cys Pro Ala Pro Glu Leu Leu Gly Gly Pro Ser Val
        230                 235                 240 ttc ctc ttc ccc cca aaa ccc aag gac acc ctc atg atc tcc cgg acc       867
Phe Leu Phe Pro Pro Lys Pro Lys Asp Thr Leu Met Ile Ser Arg Thr
    245                 250                 255 cct gag gtc aca tgc gtg gtg gtg gac gtg agc cac gaa gac cct gag       915
Pro Glu Val Thr Cys Val Val Val Asp Val Ser His Glu Asp Pro Glu
260                 265                 270 gtc aag ttc aac tgg tac gtg gac ggc gtg gag gtg cat aat gcc aag       963
Val Lys Phe Asn Trp Tyr Val Asp Gly Val Glu Val His Asn Ala Lys
275                 280                 285                 290 aca aag ccg cgg gag gag cag tac aac agc acg tac cgt gtg gtc agc      1011
Thr Lys Pro Arg Glu Glu Gln Tyr Asn Ser Thr Tyr Arg Val Val Ser
            295                 300                 305 gtc ctc acc gtc ctg cac cag gac tgg ctg aat ggc aag gag tac aag      1059
Val Leu Thr Val Leu His Gln Asp Trp Leu Asn Gly Lys Glu Tyr Lys
        310                 315                 320 tgc aag gtc tcc aac aaa gcc ctc cca gcc ccc atc gag aaa acc atc      1107
Cys Lys Val Ser Asn Lys Ala Leu Pro Ala Pro Ile Glu Lys Thr Ile
    325                 330                 335 tcc aaa gcc aaa ggg cag ccc cga gaa cca cag gtg tac acc ctg ccc      1155
Ser Lys Ala Lys Gly Gln Pro Arg Glu Pro Gln Val Tyr Thr Leu Pro
340                 345                 350 cca tcc cgg gat gag ctg acc aag aac cag gtc agc ctg acc tgc ctg      1203
Pro Ser Arg Asp Glu Leu Thr Lys Asn Gln Val Ser Leu Thr Cys Leu
355                 360                 365                 370 gtc aaa ggc ttc tat ccc agc gac atc gcc gtg gag tgg gag agc aat      1251
Val Lys Gly Phe Tyr Pro Ser Asp Ile Ala Val Glu Trp Glu Ser Asn
            375                 380                 385 ggg cag ccg gag aac aac tac aag acc acg cct ccc gtg ctg gac tcc      1299
Gly Gln Pro Glu Asn Asn Tyr Lys Thr Thr Pro Pro Val Leu Asp Ser
        390                 395                 400 gac ggc tcc ttc ttc ctc tac agc aag ctc acc gtg gac aag agc agg      1347
Asp Gly Ser Phe Phe Leu Tyr Ser Lys Leu Thr Val Asp Lys Ser Arg
    405                 410                 415 tgg cag cag ggg aac gtc ttc tca tgc tcc gtg atg cat gag gct ctg      1395
Trp Gln Gln Gly Asn Val Phe Ser Cys Ser Val Met His Glu Ala Leu
420                 425                 430 cac aac cac tac acg cag aag agc ctc tcc ctg tct ccg ggt aaa          1440
His Asn His Tyr Thr Gln Lys Ser Leu Ser Leu Ser Pro Gly Lys
```

```
                435         440         445
tgataagcgg ccgcttccct                                           1460
```

<210> SEQ ID NO 180
<211> LENGTH: 473
<212> TYPE: PRT
<213> ORGANISM: Homo Sapiens

<400> SEQUENCE: 180

Met Glu Thr Asp Thr Leu Leu Leu Trp Val Leu Leu Leu Trp Val Pro
              -20                 -15                 -10

Gly Ser Thr Gly Asp Ala Asn Ser Gln Val Gln Leu Gln Glu Ser Gly
         -5              -1   1                   5

Pro Gly Leu Val Lys Pro Ser Glu Thr Leu Ser Leu Thr Cys Thr Val
         10                  15                  20

Ser Gly Phe Ser Leu Thr Asn Tyr Gly Ile His Trp Ile Arg Gln Pro
 25              30                  35                      40

Pro Gly Lys Gly Leu Glu Trp Leu Gly Val Ile Trp Ala Arg Gly Phe
             45                  50                  55

Thr Asn Tyr Asn Ser Ala Leu Met Ser Arg Val Thr Ile Ser Lys Asp
             60                  65                  70

Asn Ser Lys Asn Gln Val Ser Leu Lys Leu Ser Ser Val Thr Ala Ala
         75                  80                  85

Asp Thr Ala Val Tyr Tyr Cys Ala Arg Ala Asn Asp Gly Val Tyr Tyr
     90                  95                 100

Ala Met Asp Tyr Trp Gly Gln Gly Thr Leu Val Thr Val Ser Ser Ala
105                 110                 115                 120

Ser Thr Lys Gly Pro Ser Val Phe Pro Leu Ala Pro Ser Ser Lys Ser
                125                 130                 135

Thr Ser Gly Gly Thr Ala Ala Leu Gly Cys Leu Val Lys Asp Tyr Phe
             140                 145                 150

Pro Glu Pro Val Thr Val Ser Trp Asn Ser Gly Ala Leu Thr Ser Gly
         155                 160                 165

Val His Thr Phe Pro Ala Val Leu Gln Ser Ser Gly Leu Tyr Ser Leu
     170                 175                 180

Ser Ser Val Val Thr Val Pro Ser Ser Ser Leu Gly Thr Gln Thr Tyr
185                 190                 195                 200

Ile Cys Asn Val Asn His Lys Pro Ser Asn Thr Lys Val Asp Lys Lys
                205                 210                 215

Val Glu Pro Lys Ser Cys Asp Lys Thr His Thr Cys Pro Pro Cys Pro
             220                 225                 230

Ala Pro Glu Leu Leu Gly Gly Pro Ser Val Phe Leu Phe Pro Pro Lys
         235                 240                 245

Pro Lys Asp Thr Leu Met Ile Ser Arg Thr Pro Glu Val Thr Cys Val
     250                 255                 260

Val Val Asp Val Ser His Glu Asp Pro Glu Val Lys Phe Asn Trp Tyr
265                 270                 275                 280

Val Asp Gly Val Glu Val His Asn Ala Lys Thr Lys Pro Arg Glu Glu
                285                 290                 295

Gln Tyr Asn Ser Thr Tyr Arg Val Val Ser Val Leu Thr Val Leu His
             300                 305                 310

Gln Asp Trp Leu Asn Gly Lys Glu Tyr Lys Cys Lys Val Ser Asn Lys
         315                 320                 325

Ala Leu Pro Ala Pro Ile Glu Lys Thr Ile Ser Lys Ala Lys Gly Gln
     330                 335                 340

```
Pro Arg Glu Pro Gln Val Tyr Thr Leu Pro Pro Ser Arg Asp Glu Leu
345                 350                 355                 360

Thr Lys Asn Gln Val Ser Leu Thr Cys Leu Val Lys Gly Phe Tyr Pro
            365                 370                 375

Ser Asp Ile Ala Val Glu Trp Glu Ser Asn Gly Gln Pro Glu Asn Asn
        380                 385                 390

Tyr Lys Thr Thr Pro Pro Val Leu Asp Ser Asp Gly Ser Phe Phe Leu
    395                 400                 405

Tyr Ser Lys Leu Thr Val Asp Lys Ser Arg Trp Gln Gln Gly Asn Val
        410                 415                 420

Phe Ser Cys Ser Val Met His Glu Ala Leu His Asn His Tyr Thr Gln
425                 430                 435                 440

Lys Ser Leu Ser Leu Ser Pro Gly Lys
                445

<210> SEQ ID NO 181
<211> LENGTH: 469
<212> TYPE: PRT
<213> ORGANISM: Homo Sapiens
<220> FEATURE:
<221> NAME/KEY: MISC_FEATURE
<223> OTHER INFORMATION: hVH14.0 IgG1 Heavy Chain [DANS-Deleted]

<400> SEQUENCE: 181

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Glu Thr Leu Ser Leu Thr Cys Thr Val Ser Gly Phe Ser
        35                  40                  45

Leu Thr Asn Tyr Gly Ile His Trp Ile Arg Gln Pro Pro Gly Lys Gly
    50                  55                  60

Leu Glu Trp Leu Gly Val Ile Trp Ala Arg Gly Phe Thr Asn Tyr Asn
65                  70                  75                  80

Ser Ala Leu Met Ser Arg Val Thr Ile Ser Lys Asp Asn Ser Lys Asn
                85                  90                  95

Gln Val Ser Leu Lys Leu Ser Ser Val Thr Ala Ala Asp Thr Ala Val
            100                 105                 110

Tyr Tyr Cys Ala Arg Ala Asn Asp Gly Val Tyr Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255
```

```
Leu Gly Gly Pro Ser Val Phe Leu Phe Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
        420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 182
<211> LENGTH: 469
<212> TYPE: PRT
<213> ORGANISM: Homo Sapeins
<220> FEATURE:
<221> NAME/KEY: MISC_FEATURE
<223> OTHER INFORMATION: hVH12.0 IgG1 Heavy Chain [DANS-deleted]

<400> SEQUENCE: 182

Met Glu Thr Asp Thr Leu Leu Leu Trp Val Leu Leu Leu Trp Val Pro
1               5                   10                  15

Gly Ser Thr Gly Gln Val Gln Leu Gln Glu Ser Gly Pro Gly Leu Val
            20                  25                  30

Lys Pro Ser Glu Thr Leu Ser Leu Thr Cys Thr Val Ser Gly Phe Ser
        35                  40                  45

Leu Thr Asn Tyr Gly Ile His Trp Ile Arg Gln Pro Pro Gly Lys Gly
    50                  55                  60

Leu Glu Trp Leu Gly Val Ile Trp Ala Arg Gly Phe Thr Asn Tyr Asn
65                  70                  75                  80

Ser Ala Leu Met Ser Arg Leu Thr Ile Ser Lys Asp Asn Ser Lys Asn
                85                  90                  95

Gln Val Ser Leu Lys Leu Ser Ser Val Thr Ala Ala Asp Thr Ala Val
            100                 105                 110

Tyr Tyr Cys Ala Arg Ala Asn Asp Gly Val Tyr Tyr Ala Met Asp Tyr
        115                 120                 125

Trp Gly Gln Gly Thr Leu Val Thr Val Ser Ser Ala Ser Thr Lys Gly
    130                 135                 140
```

-continued

```
Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
        180                 185                 190

Pro Ala Val Leu Gln Ser Ser Gly Leu Tyr Ser Leu Ser Ser Val Val
    195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 183
<211> LENGTH: 24
<212> TYPE: PRT
<213> ORGANISM: Homo sapiens

<400> SEQUENCE: 183

His Asn Ser Ser Ser Trp Tyr Gly Arg Tyr Phe Asp Tyr Trp Gly Gln
1               5                   10                  15

Gly Thr Leu Val Thr Val Ser Ser
            20

<210> SEQ ID NO 184
```

```
<211> LENGTH: 19
<212> TYPE: PRT
<213> ORGANISM: Homo sapiens

<400> SEQUENCE: 184

Glu Glu Gly Asn Thr Leu Pro Trp Thr Phe Gly Gln Gly Thr Lys Val
1               5                   10                  15

Glu Ile Lys

<210> SEQ ID NO 185
<211> LENGTH: 119
<212> TYPE: PRT
<213> ORGANISM: Artificial sequence
<220> FEATURE:
<223> OTHER INFORMATION: humanized VH region
<220> FEATURE:
<221> NAME/KEY: VARIANT
<222> LOCATION: (30)..(30)
<223> OTHER INFORMATION: Xaa at position 30 can be Thr or Ile
<220> FEATURE:
<221> NAME/KEY: VARIANT
<222> LOCATION: (31)..(31)
<223> OTHER INFORMATION: Xaa at position 31 can be Asn or Ser
<220> FEATURE:
<221> NAME/KEY: VARIANT
<222> LOCATION: (37)..(37)
<223> OTHER INFORMATION: Xaa at position 37 can be Val or Ile
<220> FEATURE:
<221> NAME/KEY: VARIANT
<222> LOCATION: (48)..(48)
<223> OTHER INFORMATION: Xaa at position 48 can be Leu or Ile
<220> FEATURE:
<221> NAME/KEY: VARIANT
<222> LOCATION: (67)..(67)
<223> OTHER INFORMATION: Xaa at position 67 can be Val or Leu
<220> FEATURE:
<221> NAME/KEY: VARIANT
<222> LOCATION: (71)..(71)
<223> OTHER INFORMATION: Xaa at position 71 can be Lys or Val
<220> FEATURE:
<221> NAME/KEY: VARIANT
<222> LOCATION: (73)..(73)
<223> OTHER INFORMATION: Xaa at position 73 can be Asn or Thr
<220> FEATURE:
<221> NAME/KEY: VARIANT
<222> LOCATION: (78)..(78)
<223> OTHER INFORMATION: Xaa at position 78 can be Val or Phe
<220> FEATURE:
<221> NAME/KEY: VARIANT
<222> LOCATION: (94)..(94)
<223> OTHER INFORMATION: Xaa at position 94 can be Phe or Tyr

<400> SEQUENCE: 185

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Xaa Xaa Tyr
            20                  25                  30

Gly Ile His Trp Xaa Arg Gln Pro Pro Gly Lys Gly Leu Glu Trp Xaa
        35                  40                  45

Gly Val Ile Trp Ala Arg Gly Phe Thr Asn Tyr Asn Ser Ala Leu Met
    50                  55                  60

Ser Arg Xaa Thr Ile Ser Xaa Asp Xaa Ser Lys Asn Gln Xaa Ser Leu
65                  70                  75                  80

Lys Leu Ser Ser Val Thr Ala Ala Asp Thr Ala Val Tyr Xaa Cys Ala
                85                  90                  95

Arg Ala Asn Asp Gly Val Tyr Tyr Ala Met Asp Tyr Trp Gly Gln Gly
            100                 105                 110

Thr Leu Val Thr Val Ser Ser
            115
```

```
<210> SEQ ID NO 186
<211> LENGTH: 106
<212> TYPE: PRT
<213> ORGANISM: Artificial sequence
<220> FEATURE:
<223> OTHER INFORMATION: humanized VL region
<220> FEATURE:
<221> NAME/KEY: VARIANT
<222> LOCATION: (1)..(1)
<223> OTHER INFORMATION: Xaa at position 1 can be Gln or Asp
<220> FEATURE:
<221> NAME/KEY: VARIANT
<222> LOCATION: (2)..(2)
<223> OTHER INFORMATION: Xaa at position 2 can be Phe or Val
<220> FEATURE:
<221> NAME/KEY: VARIANT
<222> LOCATION: (4)..(4)
<223> OTHER INFORMATION: Xaa at position 4 can be Leu or Met
<220> FEATURE:
<221> NAME/KEY: VARIANT
<222> LOCATION: (45)..(45)
<223> OTHER INFORMATION: Xaa at position 48 can be Lys or Leu
<220> FEATURE:
<221> NAME/KEY: VARIANT
<222> LOCATION: (46)..(46)
<223> OTHER INFORMATION: Xaa at position 46 can be Trp or Leu
<220> FEATURE:
<221> NAME/KEY: VARIANT
<222> LOCATION: (48)..(48)
<223> OTHER INFORMATION: Xaa at position 48 can be Tyr or Lys
<220> FEATURE:
<221> NAME/KEY: VARIANT
<222> LOCATION: (70)..(70)
<223> OTHER INFORMATION: Xaa at position 70 can be Tyr or Phe

<400> SEQUENCE: 186

Xaa Xaa Val Xaa Thr Gln Ser Pro Ala Phe Leu Ser Val Thr Pro Gly
1               5                   10                  15

Glu Lys Val Thr Ile Thr Cys Ser Ala Asn Ser Ser Val Asn Tyr Ile
            20                  25                  30

His Trp Tyr Gln Gln Lys Pro Asp Gln Ala Pro Lys Xaa Xaa Ile Xaa
        35                  40                  45

Asp Thr Ser Lys Leu Ala Ser Gly Val Pro Ser Arg Phe Ser Gly Ser
    50                  55                  60

Gly Ser Gly Thr Asp Xaa Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys
            100                 105

<210> SEQ ID NO 187
<211> LENGTH: 446
<212> TYPE: PRT
<213> ORGANISM: artificial
<220> FEATURE:
<223> OTHER INFORMATION: anti-human alpha2 integrin GBR500
      (heavy chain)

<400> SEQUENCE: 187

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Ile His Trp Ile Arg Gln Pro Pro Gly Lys Gly Leu Glu Trp Leu
        35                  40                  45
```

```
Gly Val Ile Trp Ala Arg Gly Phe Thr Asn Tyr Asn Ser Ala Leu Met
 50                  55                  60

Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Asn Asp Gly Val Tyr Tyr Ala Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 188
<211> LENGTH: 213
<212> TYPE: PRT
<213> ORGANISM: artificial
```

<220> FEATURE:
<223> OTHER INFORMATION: anti-human alpha2 integrin GBR500
      (light chain)

<400> SEQUENCE: 188

```
Asp Phe Val Met Thr Gln Ser Pro Ala Phe Leu Ser Val Thr Pro Gly
1               5                   10                  15

Glu Lys Val Thr Ile Thr Cys Ser Ala Gln Ser Ser Val Asn Tyr Ile
            20                  25                  30

His Trp Tyr Gln Gln Lys Pro Asp Gln Ala Pro Lys Lys Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Glu Ala Glu
65                  70                  75                  80

Asp Ala Ala Thr Tyr Tyr Cys Gln Gln Trp Thr Thr Asn Pro Leu Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 189
<211> LENGTH: 1338
<212> TYPE: DNA
<213> ORGANISM: artificial
<220> FEATURE:
<223> OTHER INFORMATION: anti-human alpha2 integrin GBR500 (heavy chain
      nucleo.)

<400> SEQUENCE: 189

```
caggtgcagt tgcaggagtc aggccctggc ctggtgaagc ccagcgagac cctgagcctg      60
acctgtaccg tctctggatt tagcttaacc aactatggca tccactggat acgccagcct    120
ccaggcaagg gcctggagtg gctgggcgtg atatgggctc gcggcttcac aaactataac    180
agcgctctca tgtcccgcct gaccatcagc aaggacaaca gcaagaacca ggtgagcctg    240
aagctgagca gcgtgaccgc cgcggacacc gccgtgtact actgcgccag agccaacgac    300
ggggtctact atgccatgga ctactggggc cagggaaccc tggtcaccgt cagctcagcg    360
tccaccaagg gcccatccgt cttccccctg gcgccctgct ccaggagcac ctccgagagc    420
acagccgccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac gaagacctac    600
acctgcaacg tagatcacaa gcccagcaac accaaggtgg acaagagagt tgagtccaaa    660
```

```
tatggtcccc catgcccatc atgcccagca cctgagttcc tggggggacc atcagtcttc    720
ctgttccccc caaaacccaa ggacactctc atgatctccc ggacccctga ggtcacgtgc    780
gtggtggtgg acgtgagcca ggaagacccc gaggtccagt tcaactggta cgtggatggc    840
gtggaggtgc ataatgccaa gacaaagccg cgggaggagc agttcaacag cacgtaccgt    900
gtggtcagcg tcctcaccgt cctgcaccag gactggctga acggcaagga gtacaagtgc    960
aaggtctcca acaaaggcct cccgtcctcc atcgagaaaa ccatctccaa agccaaaggg   1020
cagccccgag agccacaggt gtacaccctg cccccatccc aggaggagat gaccaagaac   1080
caggtcagcc tgacctgcct ggtcaaaggc ttctacccca gcgacatcgc cgtggagtgg   1140
gagagcaatg ggcagccgga gaacaactac aagaccacgc ctcccgtgct ggactccgac   1200
ggctccttct tcctctacag caggctaacc gtggacaaga gcaggtggca ggaggggaat   1260
gtcttctcat gctccgtgat gcatgaggct ctgcacaacc actacacaca gaagagcctc   1320
tccctgtctc tgggtaaa                                                 1338

<210> SEQ ID NO 190
<211> LENGTH: 639
<212> TYPE: DNA
<213> ORGANISM: artificial
<220> FEATURE:
<223> OTHER INFORMATION: anti-human alpha2 integrin GBR500 (light chain
      nucleo.)

<400> SEQUENCE: 190
gacttcgtga tgacccagtc tccagcattc ctgagcgtga cccccggcga gaaggtgacc     60
atcacctgca gcgcccaatc aagcgtgaac tacattcact ggtaccagca gaagcccgac    120
caggccccca agaaattgat ctatgacact tccaagctgg ccagcggcgt gcccagccgc    180
ttcagcggca gcggcagcgg caccgactac accttcacca tcagcagcct ggaggccgag    240
gacgctgcca cctattactg ccagcagtgg accactaacc cactgacctt cggccagggc    300
accaaggtcg aaatcaaacg aactgtggct gcaccatctg tcttcatctt cccgccatct    360
gatgagcagt tgaaatctgg aactgcctct gttgtgtgcc tgctgaataa cttctatccc    420
agagaggcca aagtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639
```

The invention claimed is:

1. A method of treating cancer selected from the group consisting of non-small cell lung cancer, pancreatic cancer, glioblastoma, cervical cancer, ovarian cancer, liver cancer, breast cancer, colon cancer, colorectal cancer, kidney cancer, prostate cancer, mesothelioma, fibrosarcoma, osteosarcoma, epidermoid carcinoma, metastatic colorectal, metastatic prostate and metastatic breast cancer, comprising administering to a subject a therapeutically effective amount of a humanized anti-α2 integrin antibody comprising:
   (i) a heavy chain variable region comprising the amino acid sequence of (a) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (b) SEQ ID NO:40; and
   (ii) a light chain variable region comprising the amino acid sequence of (a) an LCDR1 selected from SANSSV-NYIH (SEQ ID NO:4) or SAQSSVNYIH (SEQ ID NO:112), (b) LCDR2 (DTSKLAS; SEQ ID NO:5) and (c) LCDR3 (QQWTTNPLT, SEQ ID NO:6).

2. The method of claim 1, wherein the heavy chain variable region comprises the amino acid sequence of SEQ ID NO:185.

3. The method of claim 2, wherein the heavy chain variable region comprises the amino acid sequence of SEQ ID NO:185 in which position 30 is Thr and/or position 31 is Asn.

4. The method of claim 2, wherein the heavy chain variable region comprises the amino acid sequence of SEQ ID NO:185 in which (a) position 71 is Lys, (b) position 73 is Asn, (c) position 78 is Val, or (d) any combination of (a)-(c).

5. The method of claim 1, wherein the heavy chain variable region comprises an amino acid sequence selected from SEQ ID NOs:70-79 and SEQ ID NOs:109-111.

6. The method of claim 1, wherein the heavy chain variable region comprises an amino acid sequence selected from SEQ ID NOs:70-75, SEQ ID NOs:77-79 and SEQ ID NOs:109-111.

7. The method of claim 1, wherein the heavy chain variable region further comprises a FW4 region comprising the amino acid sequence WGQGTLVTVSS (SEQ ID NO:13).

8. The method of claim 1, wherein the heavy chain variable region comprises the amino acid sequence of HCDR1 (SEQ ID NO:1), HCDR2 (SEQ ID NO:2) and HCDR3 (SEQ ID NO:3).

9. The method of claim 1, wherein the humanized anti-α2 integrin antibody comprises a heavy chain comprising SEQ ID NO:187.

10. The method of claim 1, wherein the light chain variable region comprises the amino acid sequence of SEQ ID NO:186.

11. The method of claim 10, wherein the light chain variable region comprises the amino acid sequence of SEQ ID NO:186 in which the asparagine (N) at amino acid position 26 is replaced by glutamine (Q).

12. The method of claim 10, wherein the light chain variable region comprises the amino acid sequence of SEQ ID NO:186 in which (a) position 2 is Phe, (b) position 45 is Lys, (c) position 48 is Tyr, or (d) any combination of (a)-(c).

13. The method of claim 1, wherein the light chain variable region comprises an amino acid sequence selected from SEQ ID NO:41, SEQ ID NOs:80-92 and SEQ ID NO:108.

14. The method of claim 1, wherein the light chain variable region comprises an amino acid sequence selected from SEQ ID NOs:90-92.

15. The method of claim 1, wherein the light chain variable region further comprises a FW4 region comprising the amino acids sequence FGQGTKVEIK of SEQ ID NO:38.

16. The method of claim 1, wherein the light chain variable region comprises the amino acid sequence of LCDR1 (SEQ ID NO:4), LCDR2 (SEQ ID NO:5) and LCDR3 (SEQ ID NO:6).

17. The method of claim 1, wherein the light chain variable region comprises the amino acid sequence of LCDR1 (SEQ ID NO:112), LCDR2 (SEQ ID NO:5) and LCDR3 (SEQ ID NO:6).

18. The method of claim 1, wherein the humanized anti-α2 integrin antibody comprises a light chain comprising SEQ ID NO:188.

19. The method of claim 1, wherein the humanized anti-α2 integrin antibody comprises:
(i) a heavy chain variable region comprising the amino acid sequence of HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3); and
(ii) a light chain variable region comprising the amino acid sequence of LCDR1 (SAQSSVNYIH, SEQ ID NO:112), LCDR2 (DTSKLAS; SEQ ID NO:5) and LCDR3 (QQWTTNPLT, SEQ ID NO:6).

20. The method of claim 1, wherein (a) the heavy chain variable region comprises the amino acid sequence of SEQ ID NO:185, (b) the light chain variable region comprises the amino acid sequence of SEQ ID NO:186, or (c) both (a) and (b).

21. The method of claim 1, wherein (a) the heavy chain variable region comprises the amino acid sequence of SEQ ID NO:185 in which position 30 is Thr and/or position 31 is Asn; (b) the light chain variable region comprises the amino acid sequence of SEQ ID NO:186 in which the asparagine (N) at amino acid position 26 is replaced by glutamine (Q); or (c) both (a) and (b).

22. The method of claim 1, wherein (i) the heavy chain variable region comprises the amino acid sequence of SEQ ID NO:185 in which (a) position 71 is Lys, (b) position 73 is Asn, (c) position 78 is Val, or (d) any combination of (a)-(c); (ii) the light chain variable region comprises the amino acid sequence of SEQ ID NO:186 in which (a) position 2 is Phe, (b) position 45 is Lys, (c) position 48 is Tyr, or (d) any combination of (a)-(c); or (iii) both (i) and (ii).

23. The method of claim 1, wherein (a) the heavy chain variable region comprises an amino acid sequence selected from SEQ ID NOs:70-79 and SEQ ID NOs:109-111; (b) the light chain variable region comprises an amino acid sequence selected from SEQ ID NO:41, SEQ ID NOs:80-92 and SEQ ID NO:108; or (c) both (a) and (b).

24. The method of claim 1, wherein (a) the heavy chain variable region comprises an amino acid sequence selected from SEQ ID NOs:70-75, SEQ ID NOs:77-79 and SEQ ID NOs:109-111; (b) the light chain variable region comprises an amino acid sequence selected from SEQ ID NOs:90-92; or (c) both (a) and (b).

25. The method of claim 1, wherein the humanized anti-α2 integrin antibody comprises a heavy chain comprising SEQ ID NO:187 and a light chain comprising SEQ ID NO:188.

26. The method of claim 1, wherein the humanized anti-α2 integrin antibody comprises a heavy chain comprising SEQ ID NO:174 or SEQ ID NO:176 and a light chain comprising SEQ ID NO:178.

27. The method of claim 1, wherein the humanized anti-α2 integrin antibody recognizes the I domain of human α2 integrin.

28. The method of claim 27, wherein the α2β1 integrin ligand is selected from collagen, laminin, Echovirus-1, decorin, E-cadherin, matrix metalloproteinase I (MMP-I), endorepellin, collectin and C1q complement protein.

29. The method of claim 1, wherein the humanized anti-α2 integrin antibody binds α2β1 integrin.

30. The method of claim 1, wherein the humanized anti-α2 integrin antibody inhibits binding of α2 or α2β1 integrin to an α2β1 integrin ligand.

31. The method of claim 1, wherein the humanized anti-α2 integrin antibody binds an epitope of α2 integrin, the epitope comprising:
(a) a Lys residue corresponding to position 192 of the α2 integrin amino acid sequence set forth in SEQ ID NO:8 or position 40 of the α2 integrin I domain amino acid sequence set forth in SEQ ID NO:11;
(b) an Asn residue corresponding to position 225 of the α2 integrin amino acid sequence set forth in SEQ ID NO:8 or position 73 of the α2 integrin I domain amino acid sequence set forth in SEQ ID NO:11;
(c) a Gln residue corresponding to position 241 of the α2 integrin amino acid sequence set forth in SEQ ID NO:8 or position 89 of the α2 integrin I domain amino acid sequence set forth in SEQ ID NO:11;
(d) a Tyr residue corresponding to position 245 of the α2 integrin amino acid sequence set forth in SEQ ID NO:8 or position 93 of the α2 integrin I domain amino acid sequence set forth in SEQ ID NO:11;
(e) an Arg residue corresponding to position 317 of the α2 integrin amino acid sequence set forth in SEQ ID NO:8 or position 165 of the α2 integrin I domain amino acid sequence set forth in SEQ ID NO:11;
(f) an Asn residue corresponding to position 318 of the α2 integrin amino acid sequence set forth in SEQ ID NO:8 or position 166 of the α2 integrin I domain amino acid sequence set forth in SEQ ID NO:11; or
(g) any combination of (a) to (f).

32. The method of claim 1, wherein the humanized anti-α2 integrin antibody is a full length antibody.

33. The method of claim 1, wherein the humanized anti-α2 integrin antibody is an antigen binding fragment.

34. The method of claim 1, wherein the cancer is selected from the group consisting of pancreatic cancer, breast cancer, colon cancer, colorectal cancer, non-small cell lung cancer, fibrosarcoma, metastatic colorectal, and metastatic breast cancer.

35. The method of claim 1, wherein the cancer is selected from the group consisting of pancreatic cancer, breast cancer, colon cancer, colorectal cancer, non-small cell lung cancer, and fibrosarcoma.

36. The method of claim 1, wherein the cancer is pancreatic cancer, breast cancer or metastatic breast cancer.

37. The method of claim 26, wherein the co-administered one or more cancer medications comprise another antibody, chemo-therapeutic agent, cytotoxic agent, anti-angiogenic agent, immunosuppressive agent, prodrug, cytokine, cytokine antagonist, cytotoxic radiotherapy, corticosteroid, anti-emetic cancer vaccine, analgesic, anti-vascular agent, or growth-inhibitory agent.

38. The method of claim 1, wherein the antibody or the composition is administered by intravenous infusion or intravenous bolus.

39. The method of claim 1, wherein the therapeutically effective amount ranges from about 0.1 to about 100 mg/kg.

40. The method of claim 1, wherein the antibody or the composition is administered once every two weeks.

41. The method of claim 1, wherein the method is not associated with (a) platelet activation, (b) platelet aggregation, (c) a decrease in circulating platelet count, (d) bleeding complications, or (e) any combination of (a) to (d).

42. The method of claim 1, wherein the antibody or the composition is co-administered with one or more cancer medications.

43. A method of treating cancer selected from the group consisting of non-small cell lung cancer, pancreatic cancer, glioblastoma, cervical cancer, ovarian cancer, liver cancer, breast cancer, colon cancer, colorectal cancer, kidney cancer, prostate cancer, mesothelioma, fibrosarcoma, osteosarcoma, epidermoid carcinoma, metastatic colorectal, metastatic prostate and metastatic breast cancer, comprising administering to a subject a composition comprising a therapeutically effective amount of a humanized anti-α2 integrin antibody comprising:
  (i) a heavy chain variable region comprising the amino acid sequence of (a) HCDR1 (GFSLTNYGIH, SEQ ID NO:1), HCDR2 (VIWARGFTNYNSALMS, SEQ ID NO:2) and HCDR3 (ANDGVYYAMDY, SEQ ID NO:3), or (b) SEQ ID NO:40; and
  (ii) a light chain variable region comprising the amino acid sequence of (a) an LCDR1 selected from SANSSVNYIH (SEQ ID NO:4) or SAQSSVNYIH (SEQ ID NO:112), (b) LCDR2 (DTSKLAS: SEQ ID NO:5) and (c) LCDR3 (QQWTTNPLT, SEQ ID NO:6) and a pharmaceutically acceptable carrier.

* * * * *